ically ant

(12) United States Patent
Png et al.

(10) Patent No.: US 10,550,183 B2
(45) Date of Patent: Feb. 4, 2020

(54) BLOCKADE OF CD7 EXPRESSION AND CHIMERIC ANTIGEN RECEPTORS FOR IMMUNOTHERAPY OF T-CELL MALIGNANCIES

(71) Applicant: National University of Singapore, Singapore (SG)

(72) Inventors: Yi Tian Png, Singapore (SG); Natasha Vinanica, Singapore (SG); Takahiro Kamiya, Tokyo (JP); Dario Campana, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 15/821,170

(22) Filed: Nov. 22, 2017

(65) Prior Publication Data

US 2018/0148506 A1    May 31, 2018

Related U.S. Application Data

(60) Provisional application No. 62/425,398, filed on Nov. 22, 2016, provisional application No. 62/543,696, filed on Aug. 10, 2017.

(51) Int. Cl.
*C07K 16/28*    (2006.01)
*A61P 35/02*    (2006.01)
(Continued)

(52) U.S. Cl.
CPC .......... *C07K 16/2803* (2013.01); *A61K 35/17* (2013.01); *A61P 35/02* (2018.01);
(Continued)

(58) Field of Classification Search
CPC .......... A61K 2039/505; A61K 2300/00; A61K 39/3955; A61K 45/06; A61K 39/39558; A61K 47/6851; A61K 47/6803; A61K 2039/572; A61K 47/6849; A61K 51/1096; A61K 31/551; A61K 31/5517; A61K 47/6857; A61K 47/48569; A61K 47/6869; A61K 31/337; A61K 39/395; A61K 47/6843; A61K 47/6889; A61K 2039/507; A61K 31/7068; A61K 47/6809; A61K 47/6825; A61K 47/6891; A61K 35/17; A61K 47/48384; A61K 47/6855; A61K 31/47; A61K 33/24; A61K 47/6859; A61K 31/4745; A61K 31/519; A61K 47/6811; A61K 31/282; A61K 47/48415; A61K 47/48561; A61K 31/55; A61K 35/15; A61K 47/48592; A61K 47/6845; A61K 47/6867; A61K 2032/124; A61K 2039/545; A61K 31/138; A61K 31/166; A61K 31/403; A61K 31/4045; A61K 31/4168; A61K 31/4178; A61K 31/473; A61K 31/513; A61K 31/706; A61K 41/0028; A61K 47/48; A61K 47/48538; A61K 47/6813; A61K 47/6817; A61K 47/6861; A61K 48/00; A61K 49/0058; A61K 2039/5158; A61K 2039/54; A61K 2039/575; A61K 31/00; A61K 31/165; A61K 31/357; A61K 31/401; A61K 31/4184; A61K 31/436; A61K 31/4418; A61K 31/4706; A61K 31/495; A61K 31/497; A61K 31/506; A61K 31/525; A61K 31/5377; A61K 31/5513; A61K 31/565; A61K 35/13; A61K 35/28; A61K 35/42; A61K 38/02; A61K 38/18; A61K 38/482; A61K 39/0005; A61K 39/0011; A61K 39/39591; A61K 45/00; A61K 47/481; A61K 47/48407; A61K 47/48469; A61K 47/48623; A61K 47/48638; A61K 47/48715; A61K 47/48723; A61K 47/6829; A61K 47/6863; A61K 47/6865; A61K 47/6879; A61K 47/6881; A61K 47/6923; A61K 47/6929; A61K 49/225; A61K 51/1018; A61K 51/1021; A61K 51/1036; A61K 51/1045; A61K 51/1051; A61K 51/109; A61K 9/50; C07K 2317/76; C07K 16/28; C07K 2317/565; C07K 2317/92;
(Continued)

(56) References Cited

U.S. PATENT DOCUMENTS

2006/0034834 A1    2/2006  Marasco et al.
2007/0036773 A1    2/2007  Cooper et al.
(Continued)

FOREIGN PATENT DOCUMENTS

CA       2 937 157 A1    1/2018
WO    WO2003051926 A2 *  6/2003    ............. C07K 16/00
(Continued)

OTHER PUBLICATIONS

Böldicke, Thomas, "Blocking translocation of cell surface molecules from the ER to the cell surface by intracellular antibodies targeted to the ER", J. Cell. Mol. Med., vol. 11, No. 1, 2007, pp. 54-70.

(Continued)

*Primary Examiner* — Janet L Epps-Smith
(74) *Attorney, Agent, or Firm* — Morgan, Lewis & Bockius LLP

(57) ABSTRACT

The present invention provides compositions comprising an anti-CD7 chimeric activating receptor (CAR) and an anti-CD7 protein expression blocker, and methods of using such compositions in cancer therapy.

6 Claims, 23 Drawing Sheets

Specification includes a Sequence Listing.

(51) Int. Cl.
　　　*A61K 35/17*　　(2015.01)
　　　*C07K 14/725*　　(2006.01)
　　　*C07K 14/705*　　(2006.01)
　　　*C07K 16/30*　　(2006.01)
　　　*A61K 38/00*　　(2006.01)

(52) U.S. Cl.
　　　CPC .... *C07K 14/7051* (2013.01); *C07K 14/70517* (2013.01); *C07K 14/70578* (2013.01); *C07K 16/3061* (2013.01); *A61K 38/00* (2013.01); *C07K 2317/56* (2013.01); *C07K 2317/622* (2013.01); *C07K 2317/76* (2013.01); *C07K 2319/02* (2013.01); *C07K 2319/03* (2013.01); *C07K 2319/04* (2013.01); *C07K 2319/05* (2013.01); *C07K 2319/74* (2013.01)

(58) Field of Classification Search
CPC ............ C07K 2317/56; C07K 2317/24; C07K 2317/21; C07K 16/18; C07K 16/30; C07K 2317/73; C07K 2317/34; C07K 2317/31; C07K 2317/33; C07K 2317/622; C07K 2317/55; C07K 2317/732; C07K 2319/30; C07K 16/3023; C07K 2317/20; C07K 2317/77; C07K 2317/35; C07K 16/3069; C07K 2317/53; C07K 2317/54; C07K 16/2809; C07K 2317/626; C07K 2317/70; C07K 16/22; C07K 16/2863; C07K 2317/94; C07K 16/32; C07K 2317/52; C07K 14/705; C07K 16/2896; C07K 16/00; C07K 16/303; C07K 16/2866; C07K 16/3055; C07K 16/3046; C07K 2317/515; C07K 2317/567; C07K 2317/734; C07K 16/2803; C07K 2317/14; C07K 2317/51; C07K 2317/569; C07K 16/3053; C07K 16/468; C07K 2317/526; C07K 2319/00; C07K 2319/50; C07K 2319/74; C07K 16/241; C07K 16/2875; C07K 16/2887; C07K 2317/22; C07K 2317/30; C07K 2317/64; C07K 2319/03; C07K 2319/60; C07K 7/06; C07K 7/08; C07K 14/001; C07K 14/47; C07K 14/7051; C07K 14/70578; C07K 14/715; C07K 16/2818; C07K 16/2845; C07K 16/40; C07K 2317/40; C07K 2317/41; C07K 2317/524; C07K 2317/75; C07K 2319/21; C07K 2319/31; C07K 2319/32; C07K 2319/42; C07K 14/70514; C07K 14/70521; C07K 14/71; C07K 16/10; C07K 16/1282; C07K 16/24; C07K 16/2812; C07K 16/2815; C07K 16/2827; C07K 16/2869; C07K 16/2878; C07K 16/2884; C07K 16/289; C07K 16/3007; C07K 16/3061; C07K 16/3092; C07K 1/16; C07K 2299/00; C07K 2317/32; C07K 2317/66; C07K 2317/71; C07K 2317/72; C07K 2317/74; C07K 2317/80; C07K 2317/90; C07K 2319/02; C07K 2319/33; C07K 2319/95; C12N 15/09; C12N 15/63; C12N 15/86; C12N 2501/415; C12N 2501/42; C12N 2510/00; C12N 5/0638; C12N 5/0647; C12N 5/0695; C12N 5/10; C12N 5/12; C12N 9/14; C12N 15/00; C12N 15/1037; C12N 15/1058; C12N 15/907; C12N 2330/50; C12N 2501/113; C12N 2501/115; C12N 2501/117; C12N 2501/119; C12N 2501/125; C12N 2501/13; C12N 2501/145; C12N 2501/15; C12N 2501/155; C12N 2501/17; C12N 2501/2303; C12N 2501/2306; C12N 2501/26; C12N 2501/599; C12N 2501/727; C12N 2501/19; C12N 2501/998; C12N 2501/999; C12N 2502/27; C12N 2740/15043; C12N 2740/16041; C12N 2810/6081; C12N 5/00; C12N 5/0631; C12N 5/0636; C12N 5/0689; C12N 5/0693; C12N 5/0697; C12N 5/16; C12N 9/22; C12N 9/6467; C12Y 301/03001; C12Y 301/00; C12Y 304/21079; A61B 5/0095; A61B 5/4848
USPC .................. 435/320.1, 325, 375; 514/255.05
See application file for complete search history.

(56) References Cited

U.S. PATENT DOCUMENTS

| | | | |
|---|---|---|---|
| 2013/0287748 A1* | 10/2013 | June ...................... | A61K 35/17 424/93.21 |
| 2014/0120622 A1 | 5/2014 | Gregory | |
| 2014/0186387 A1 | 7/2014 | Lauer | |
| 2016/0256488 A1 | 9/2016 | Wu | |
| 2016/0312182 A1 | 10/2016 | Sentman | |

FOREIGN PATENT DOCUMENTS

| | | | | |
|---|---|---|---|---|
| WO | WO 2012/079000 A1 | 6/2012 | | |
| WO | WO 2014/124143 A1 | 8/2014 | | |
| WO | WO 2015/075468 A1 | 5/2015 | | |
| WO | WO 2015/150771 A1 | 10/2015 | | |
| WO | WO 2016/055551 A1 | 4/2016 | | |
| WO | WO 2016/102965 A1 | 6/2016 | | |
| WO | WO 2016/126213 A1 | 8/2016 | | |
| WO | WO-2016126213 A1 * | 8/2016 | ......... | C07K 16/2809 |
| WO | WO 2017/213979 A1 | 12/2017 | | |
| WO | WO 2018/027036 A1 | 2/2018 | | |

OTHER PUBLICATIONS

Clift, Dean, et al "A Method for the Acute and Rapid Degradation of Endogenous Proteins", Elsevier Inc., Cell 172, Dec. 14, 2017, pp. 1692-1706.
Marschall, Andrea LJ, et al "Specific in vivo knockdown of protein function by intrabodies", Taylor & Francis Group, LLC, Nov./Dec. 2015, vol. 7, Issue 6, pp. 1010-1035.
XP-002784541 "A simple protein-based method for generation of 'off the shelf' allogeneic chimeric antigen receptor T-cells", Journal Conference Abstract, Molecular Therapy, May 1, 2018, vol. 26, No. 5, pp. 296-297.
Hegde, M. et al., "Combinational targeting offsets antigen escape and enhances effector functions of adoptively transferred T cells in glioblastoma", Molecular Therapy, 2013, vol. 21, pp. 2087-2101.
Kamiya, et al., A novel method to generate T-cell receptor-deficient antigen receptor T cells, Blood Advances, vol. 2, No. 5, Mar. 13, 2018, pp. 517-528.
Kloss, C.C. et al., "Combinatorial antigen recognition with balanced signaling promotes selective tumor eradication by engineered T cells", Nature Biotechnology, 2013, vol. 31, pp. 71-75.
Kudo, K. et al., "T lymphocytes expressing a CD16 signaling receptor exert antibody dependent cancer cell killing". Cancer Research, 2014, vol. 74, pp. 93-103.
Lantis, E. et al., "Chimeric antigen receptor T Cells with dissociated signaling domains exhibit focused antitumor activity with reduced potential for toxicity in vivo", Cancer Immunology Research, 2013, vol. 1, pp. 43-53.
Lo, A.S.Y. et al., "Harnessing the tumour-derived cytokine, CSF-1, to co-stimulate Tcell growth and activation", Molecular Immunology, 2008, vol. 45, pp. 1276-1287.

(56) References Cited

OTHER PUBLICATIONS

Imamura. M. et al., "Autonomous growth and increased cytotoxicity of natural killer cells expressing membrane-bound interleukin-15", Blood, 2014, vol. 124, pp. 1081-1088.
Rossig, C. et al., "Genetic modification of T lymphocytes for adoptive immunotherapy", Molecular Therapy, 2004, vol. 10, pp. 5-18.
Rowley, J. et al., "Expression of IL-15RA or an IL-15/IL-15RA fusion on CD8+ T cells modifies adoptively transferred T-cell function in cis", European Journal of Immunology, 2009, vol. 39, pp. 491-506.
Sanz, L. et al., "Antibodies and gene therapy: teaching old 'magic bullets' new tricks", Trends in Immunology, 2004, vol. 25, pp. 85-91.
Zhou, P. et al., "Cells transfected with a non-neutralizing antibody gene are resistant to HIV infection: targeting the endoplasmic reticulum and *trans-Golgi* network", The Journal of Immunology, 1998, vol. 160, pp. 1489-1496.
Png, Yi Tian, et al., "Blockade of CD7 expression in T cells for effective chimeric antigen receptor targeting of T-cell malignancies", 2017, Blood Advances, vol. 1, pp. 2348-2360.
Arase, Hisashi, et al. "Recognition of virus infected cells by NK cells", Department of Immunochemistry, Research Institute for Microbial Diseases, Osaka University, vol. 54, No. 2, pp. 153-160.
Milone, Michael C., et al. "Chimeric Receptors Containing CD137 Signal Transduction Domains Mediate Enhanced Survival of T Cells and Increased Antileukemic Efficacy *In Vivo*," Mol. Ther., 2009, vol. 17, No. 8, pp. 1453-1464.

\* cited by examiner

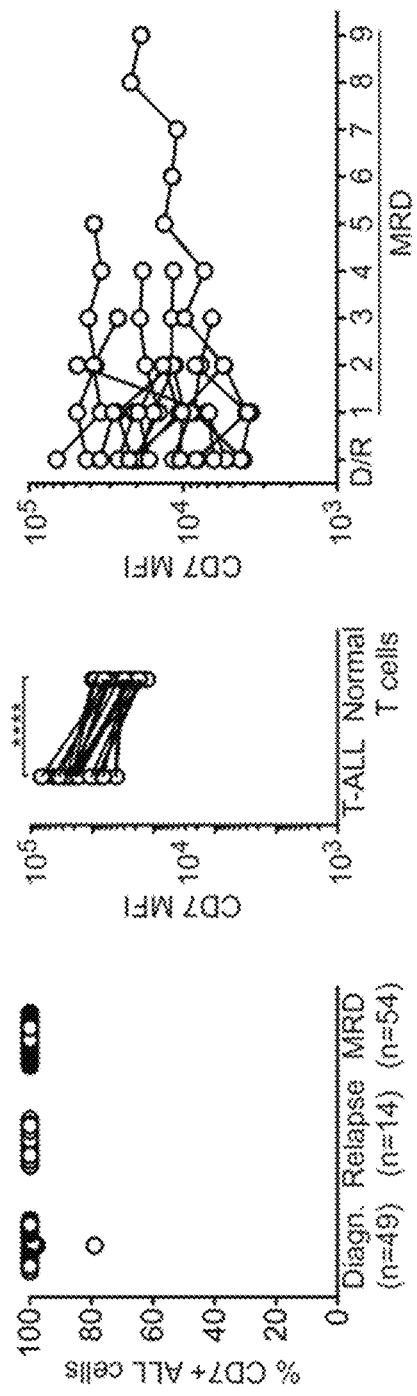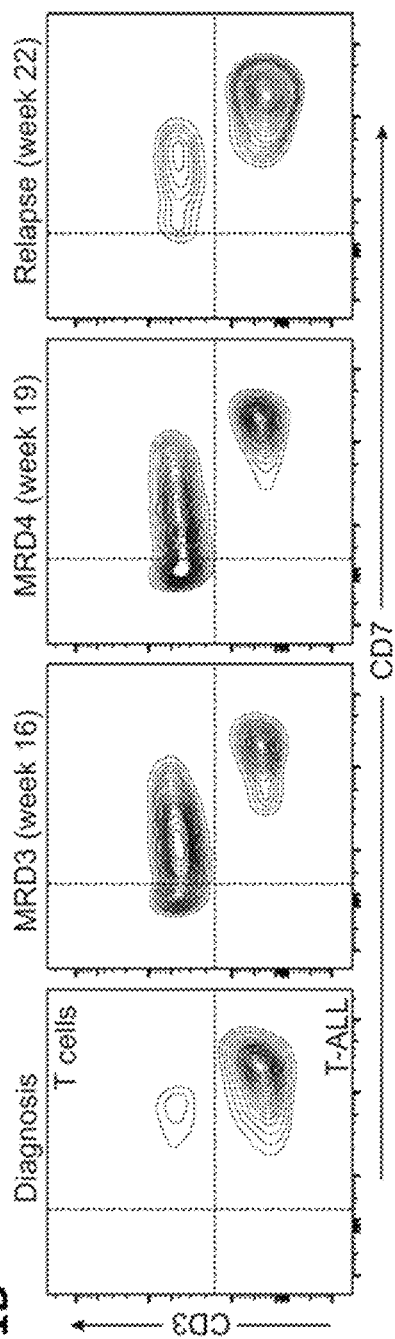
FIG. 1A
FIG. 1B
FIG. 1C
FIG. 1D

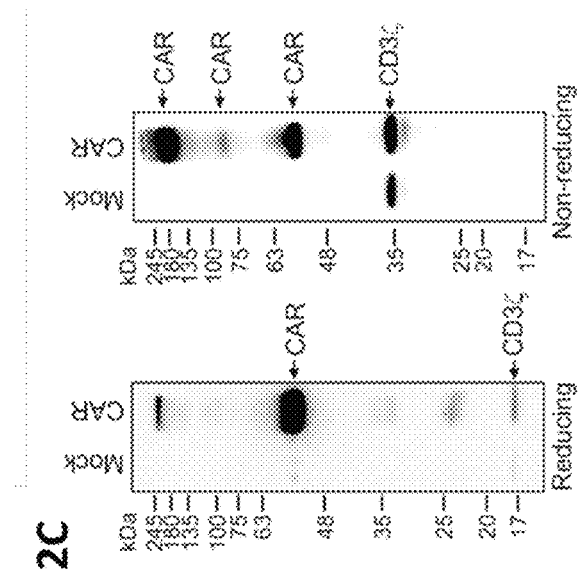
FIG. 2A
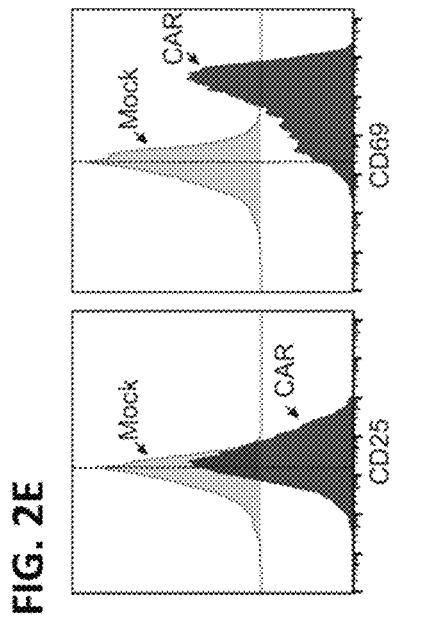
FIG. 2C
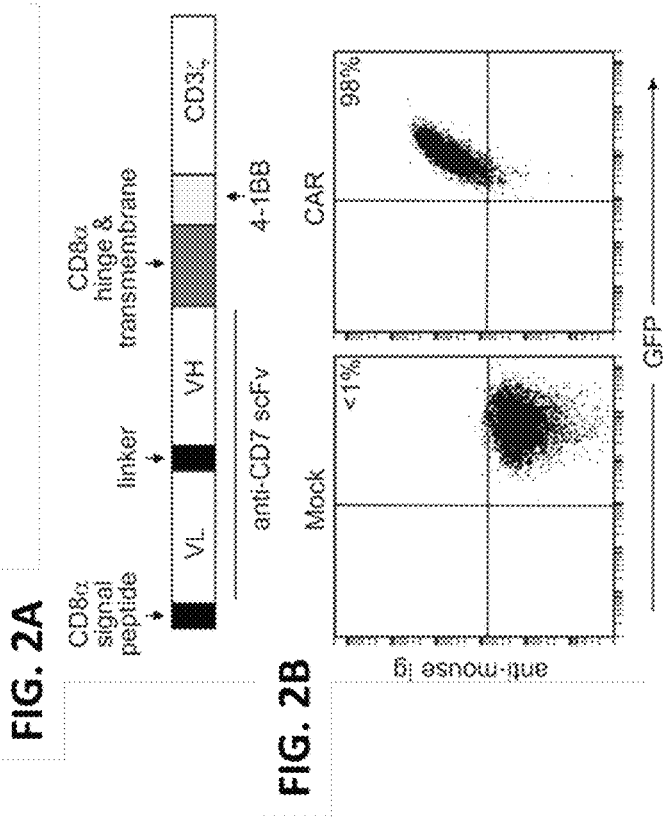
FIG. 2B
FIG. 2E
FIG. 2D

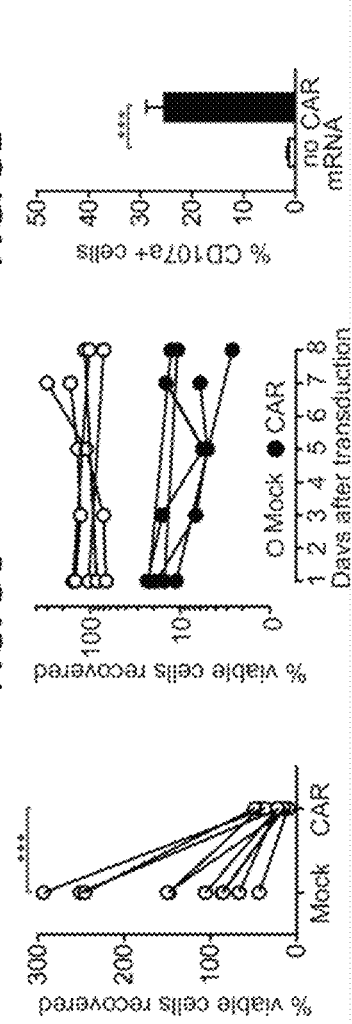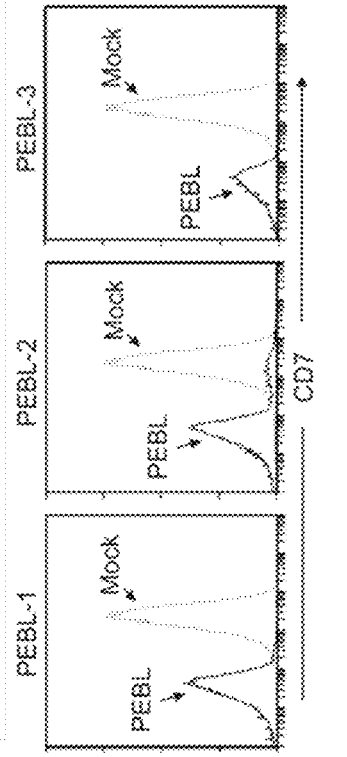
FIG. 3A FIG. 3B FIG. 3C FIG. 3D
FIG. 3E
anti-CD7 PEBL
PEBL-1: EQKLISEEDLKDEL
PEBL-2: CD8α hinge & transmembrane + LYKYKSRRSFIDEKKMP
PEBL-3: (GGGGS)₄AEKDEL
FIG. 3F

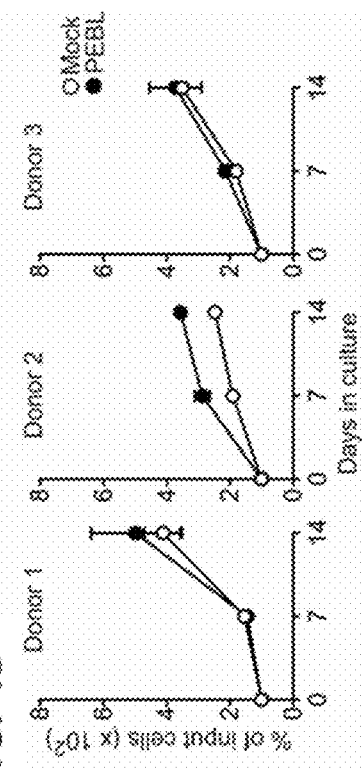
FIG. 4A
FIG. 4B
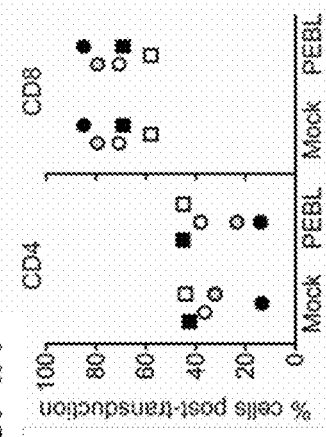
FIG. 4C
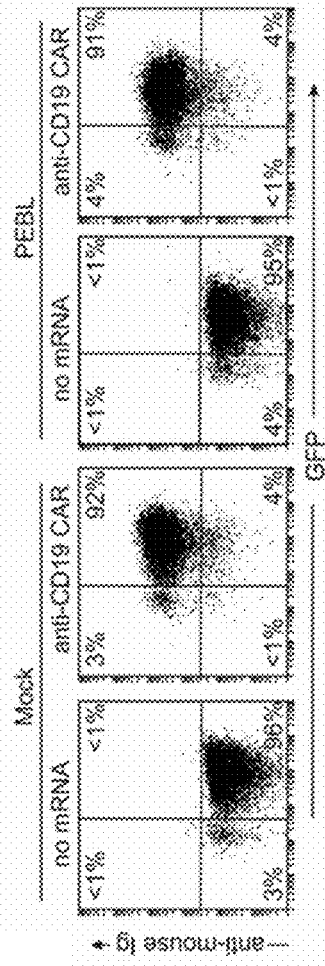

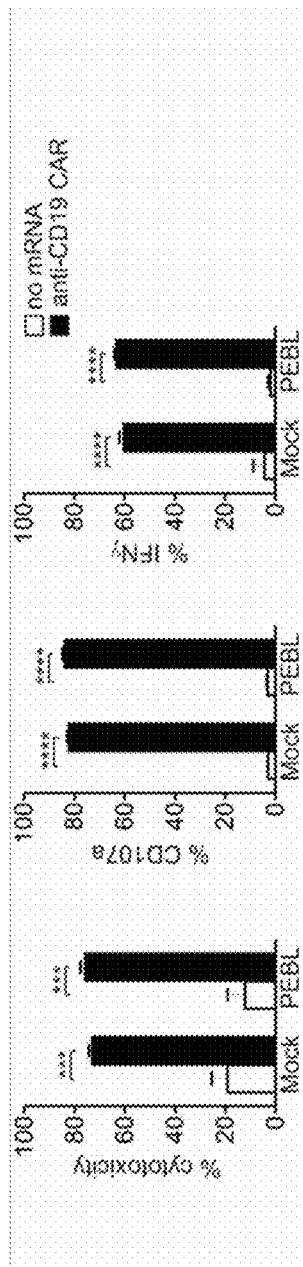

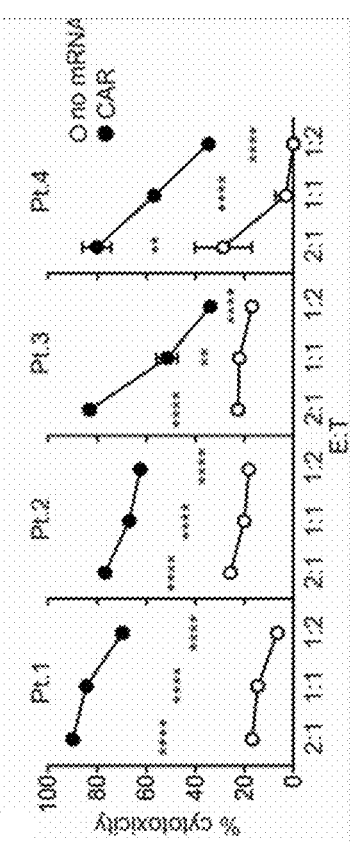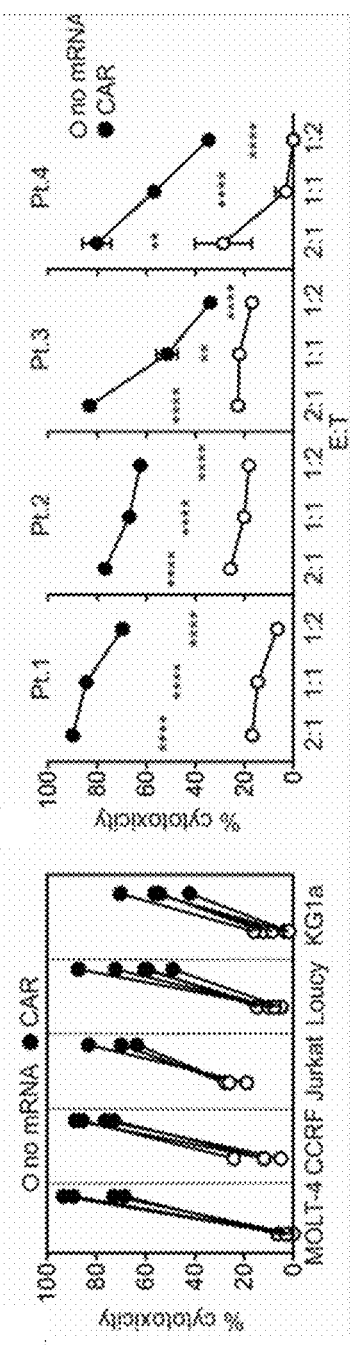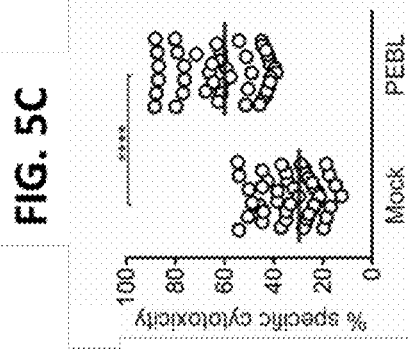
FIG. 5A  FIG. 5B  FIG. 5C  FIG. 5D

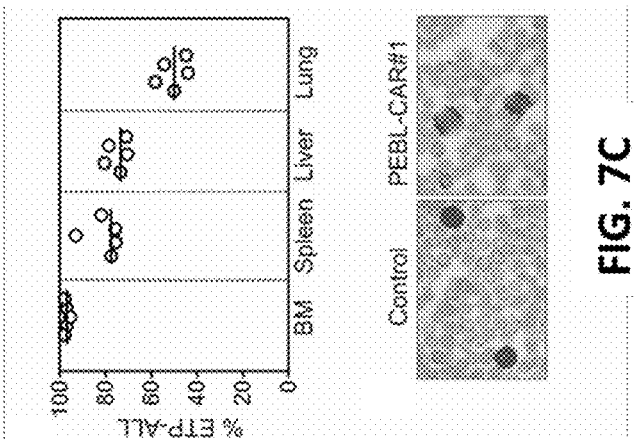
FIG. 7B
FIG. 7C
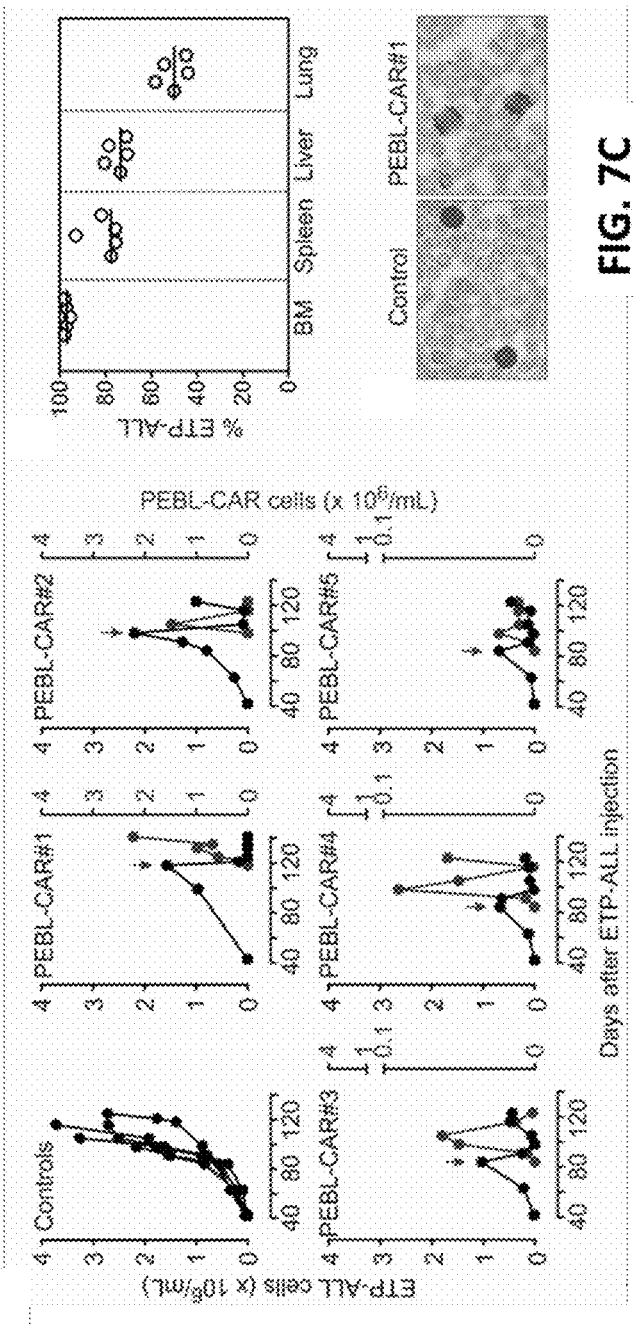
FIG. 7A

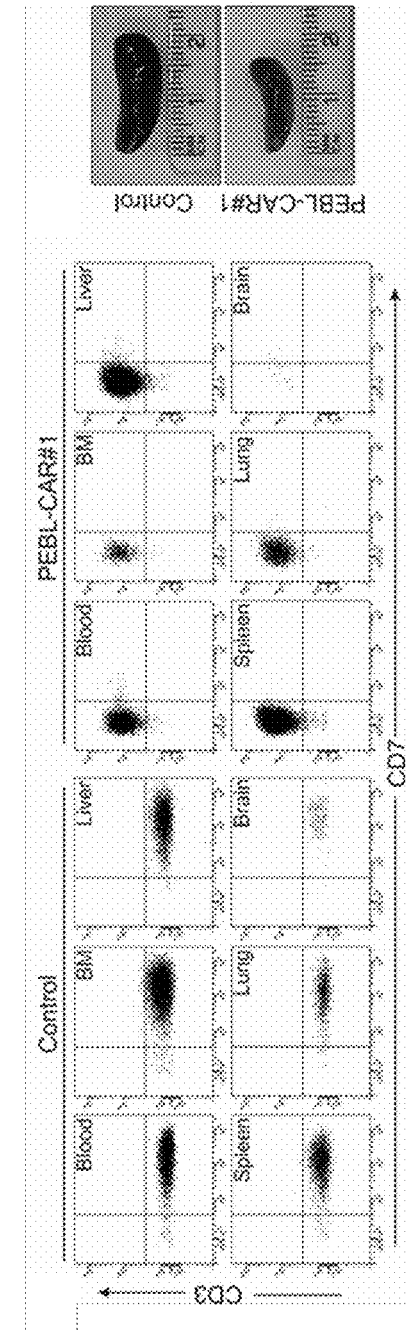

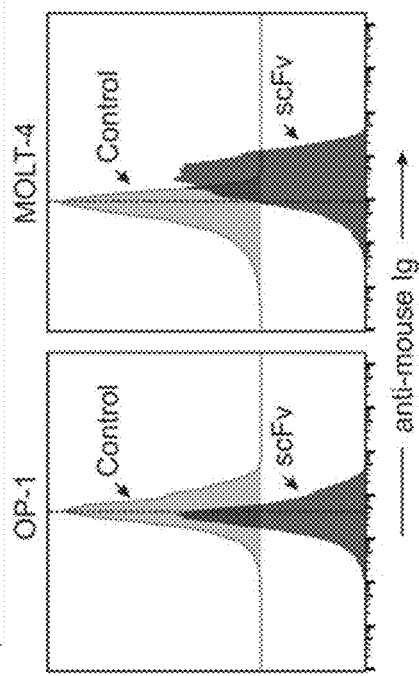
FIG. 8A
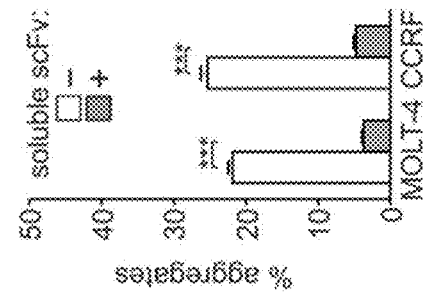
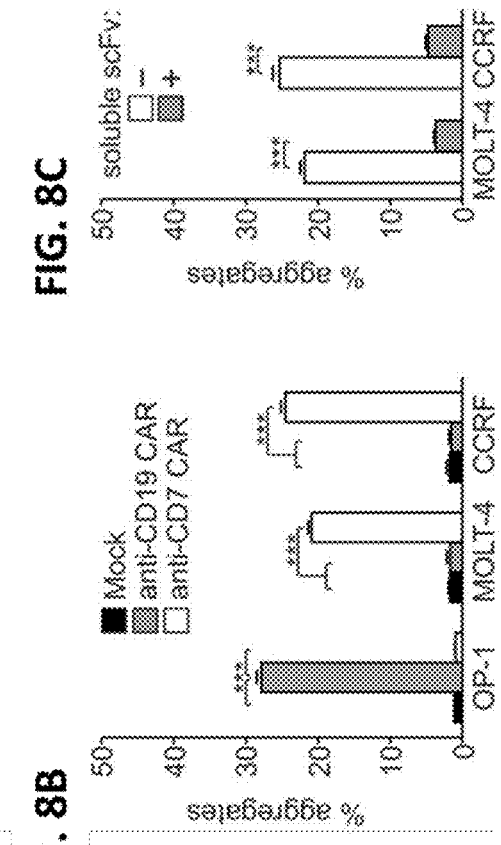
FIG. 8B
FIG. 8C

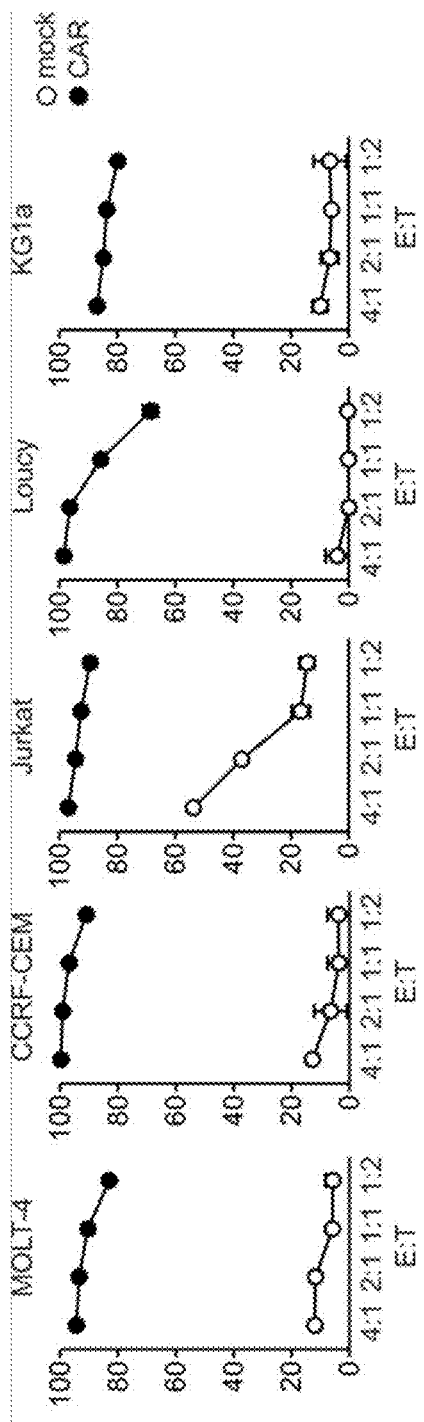

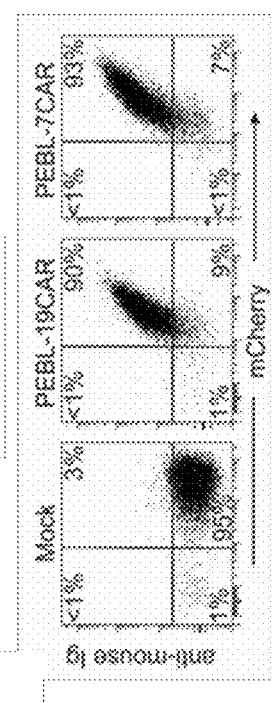
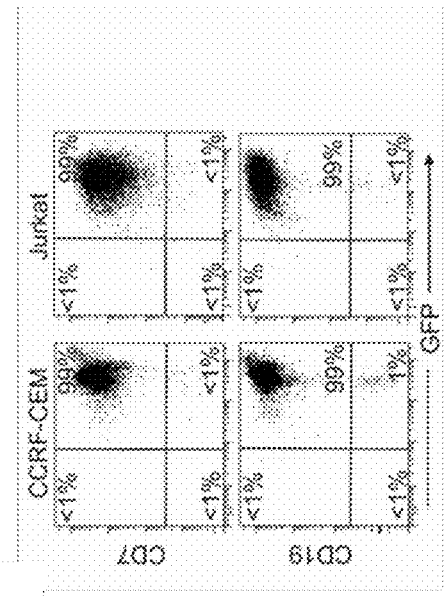
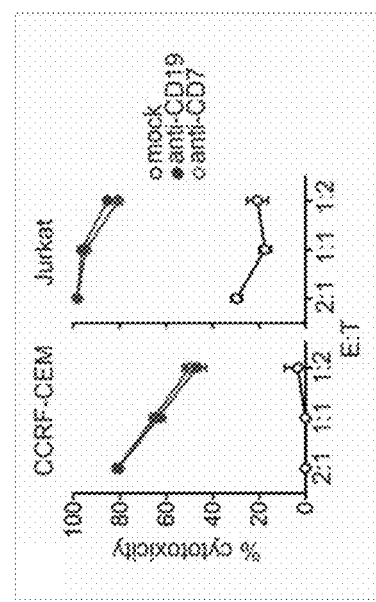
FIG. 13A
FIG. 13B
FIG. 13C

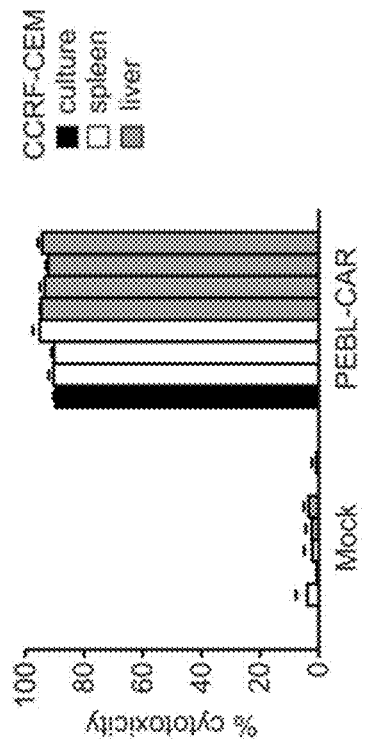
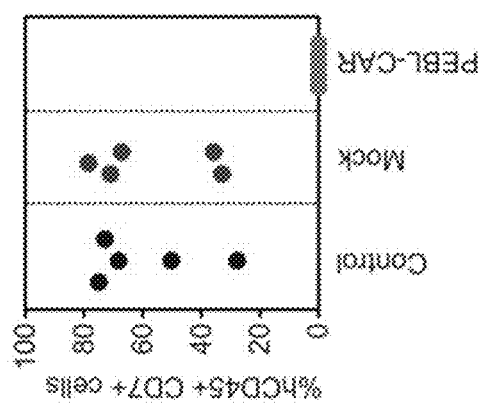

SEQUENCE LISTING

<160> NUMBER OF SEQ ID NOS: 40

<210> SEQ ID NO 1
<211> LENGTH: 117
<212> TYPE: PRT
<213> ORGANISM: Artificial Sequence
<220> FEATURE:
<223> OTHER INFORMATION: VH domain of TH69 antibody (anti-CD7 scFv)

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Leu Thr Phe Ser Ser Tyr
            20                  25                  30

Ala Met Ser Trp Val Arg Gln Thr Pro Glu Lys Arg Leu Glu Trp Val
            35                  40                  45

Ala Ser Ile Ser Ser Gly Gly Phe Thr Tyr Tyr Pro Asp Ser Val Lys
        50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Asp Glu Val Arg Gly Tyr Leu Asp Val Trp Gly Ala Gly Thr Thr
            100                 105                 110

Val Thr Val Ser Ser
            115

<210> SEQ ID NO 2
<211> LENGTH: 112
<212> TYPE: PRT
<213> ORGANISM: Artificial Sequence
<220> FEATURE:
<223> OTHER INFORMATION: VL domain of TH69 antibody (anti-CD7 scFv)

<400> SEQUENCE: 2

Ala Ala Tyr Lys Asp Ile Gln Met Thr Gln Thr Thr Ser Ser Leu Ser
1               5                   10                  15

Ala Ser Leu Gly Asp Arg Val Thr Ile Ser Cys Ser Ala Ser Gln Gly
            20                  25                  30

Ile Ser Asn Tyr Leu Asn Trp Tyr Gln Gln Lys Pro Asp Gly Thr Val
            35                  40                  45

Lys Leu Leu Ile Tyr Tyr Thr Ser Ser Leu His Ser Gly Val Pro Ser
        50                  55                  60

Arg Phe Ser Gly Ser Gly Ser Gly Thr Asp Tyr Ser Leu Thr Ile Ser
65                  70                  75                  80

Asn Leu Glu Pro Glu Asp Ile Ala Thr Tyr Tyr Cys Gln Gln Tyr Ser
                85                  90                  95

Lys Leu Pro Tyr Thr Phe Gly Gly Gly Thr Lys Leu Glu Ile Lys Arg
            100                 105                 110

<210> SEQ ID NO 3
<211> LENGTH: 42
<212> TYPE: PRT
<213> ORGANISM: Artificial Sequence
<220> FEATURE:
<223> OTHER INFORMATION: intracellular signaling domain of 4-1BB

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 4
<211> LENGTH: 112
<212> TYPE: PRT
<213> ORGANISM: Artificial Sequence
<220> FEATURE:
<223> OTHER INFORMATION: intracellular signaling domain of CD3zeta

```
<400> SEQUENCE: 4

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65              70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 45
<212> TYPE: PRT
<213> ORGANISM: Artificial Sequence
<220> FEATURE:
<223> OTHER INFORMATION: Hinge region of anti-CD7 CAR

<400> SEQUENCE: 5

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 6
<211> LENGTH: 24
<212> TYPE: PRT
<213> ORGANISM: Artificial Sequence
<220> FEATURE:
<223> OTHER INFORMATION: transmembrane region of anti-CD7 CAR

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 7
<211> LENGTH: 21
<212> TYPE: PRT
<213> ORGANISM: Artificial Sequence
<220> FEATURE:
<223> OTHER INFORMATION: CD8a signal peptide of anti-CD7 CAR

<400> SEQUENCE: 7

Met Ala Leu Pro Val Thr Ala Leu Leu Leu Pro Leu Ala Leu Leu Leu
1               5                   10                  15

His Ala Ala Arg Pro
                20

<210> SEQ ID NO 8
<211> LENGTH: 14
<212> TYPE: PRT
<213> ORGANISM: Artificial Sequence
```

```
<220> FEATURE:
<223> OTHER INFORMATION: Localization domain

<400> SEQUENCE: 8

Glu Gln Lys Leu Ile Ser Glu Glu Asp Leu Lys Asp Glu Leu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Localizing domain

<400> SEQUENCE: 9

Gly Gly Gly Gly Ser Ala Glu Lys Asp Glu Leu
1               5                   10

<210> SEQ ID NO 10
<211> LENGTH: 68
<212> TYPE: PRT
<213> ORGANISM: Artificial Sequence
<220> FEATURE:
<223> OTHER INFORMATION: Localizing domain

<400> SEQUENCE: 10

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr
65

<210> SEQ ID NO 11
<211> LENGTH: 15
<212> TYPE: PRT
<213> ORGANISM: Artificial Sequence
<220> FEATURE:
<223> OTHER INFORMATION: Localizing domain

<400> SEQUENCE: 11

Lys Tyr Lys Ser Arg Arg Ser Phe Ile Asp Glu Lys Lys Met Pro
1               5                   10                  15

<210> SEQ ID NO 12
<211> LENGTH: 20
<212> TYPE: PRT
<213> ORGANISM: Artificial Sequence
<220> FEATURE:
<223> OTHER INFORMATION: Linker

<400> SEQUENCE: 12

Gly Gly Gly Gly Ser Gly Gly Gly Ser Gly Gly Gly Ser Gly
1               5                   10                  15

Gly Gly Gly Ser
            20
```

<210> SEQ ID NO 13
<211> LENGTH: 83
<212> TYPE: PRT
<213> ORGANISM: Artificial Sequence
<220> FEATURE:
<223> OTHER INFORMATION: Localizing domain

<400> SEQUENCE: 13

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Lys Tyr Lys Ser Arg Arg Ser Phe Ile Asp Glu Lys
65                  70                  75                  80

Lys Met Pro

<210> SEQ ID NO 14
<211> LENGTH: 123
<212> TYPE: PRT
<213> ORGANISM: Artificial Sequence
<220> FEATURE:
<223> OTHER INFORMATION: VH domain of 3alf antibody (anti-CD7 scFv)

<400> SEQUENCE: 14

Gln Val Gln Leu Gln Glu Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Lys Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Val Tyr Tyr Asp Leu Tyr Tyr Ala Leu Asp Tyr
            100                 105                 110

Trp Gly Gln Gly Thr Thr Val Thr Val Ser Ser
        115                 120

<210> SEQ ID NO 15
<211> LENGTH: 108
<212> TYPE: PRT
<213> ORGANISM: Artificial Sequence
<220> FEATURE:
<223> OTHER INFORMATION: VL domain of 3alf antibody (anti-CD7 scFv)

<400> SEQUENCE: 15

Asp Ile Glu Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

```
Lys Ser Ala Ser Gln Ser Ile Ser Gly Ile Pro Ser Arg Phe Ser Gly
         50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Tyr
                 85                  90                  95

Thr Phe Gly Gly Gly Thr Lys Leu Glu Ile Lys Arg
                100                 105
```

```
<210> SEQ ID NO 16
<211> LENGTH: 120
<212> TYPE: PRT
<213> ORGANISM: Artificial Sequence
<220> FEATURE:
<223> OTHER INFORMATION: VH domain of T3-3A1 antibody (anti-CD7 scFv)

<400> SEQUENCE: 16

Asp Val Gln Leu Val Glu Ser Gly Gly Gly Leu Val Gln Pro Gly Gly
 1               5                  10                  15

Ser Arg Lys Leu Ser Cys Ala Ala Ser Gly Phe Thr Phe Ser Ser Phe
                 20                  25                  30

Gly Met His Trp Val Arg Gln Ala Pro Glu Lys Gly Leu Glu Trp Val
             35                  40                  45

Ala Tyr Ile Ser Ser Gly Ser Ser Thr Leu His Tyr Ala Asp Thr Val
 50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Trp Gly Asn Tyr Pro His Tyr Ala Met Asp Tyr Trp Gly Gln
                100                 105                 110

Gly Thr Ser Val Thr Val Ser Ser
            115                 120
```

```
<210> SEQ ID NO 17
<211> LENGTH: 111
<212> TYPE: PRT
<213> ORGANISM: Artificial Sequence
<220> FEATURE:
<223> OTHER INFORMATION: VL domain of T3-3A1 antibody (anti-CD7 scFv)

<400> SEQUENCE: 17

Asp Ile Val Met Thr Gln Ser Pro Ala Ser Leu Ala Val Ser Leu Gly
 1               5                  10                  15

Gln Arg Ala Thr Ile Ser Cys Arg Ala Ser Lys Ser Val Ser Ala Ser
                 20                  25                  30

Gly Tyr Ser Tyr Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Val Thr Tyr Tyr Cys Gln His Ser Arg
                 85                  90                  95

Glu Leu Pro Tyr Thr Phe Gly Gly Gly Thr Lys Leu Glu Ile Lys
                100                 105                 110
```

```
<210> SEQ ID NO 18
<211> LENGTH: 4
<212> TYPE: PRT
<213> ORGANISM: Artificial Sequence
<220> FEATURE:
<223> OTHER INFORMATION: Localizing sequence

<400> SEQUENCE: 18

Lys Asp Glu Leu
1

<210> SEQ ID NO 19
<211> LENGTH: 4
<212> TYPE: PRT
<213> ORGANISM: Artificial Sequence
<220> FEATURE:
<223> OTHER INFORMATION: Localizing sequence
<220> FEATURE:
<221> NAME/KEY: misc_feature
<222> LOCATION: (3)..(4)
<223> OTHER INFORMATION: Xaa can be any naturally occurring amino acid

<400> SEQUENCE: 19

Lys Lys Xaa Xaa
1

<210> SEQ ID NO 20
<211> LENGTH: 3
<212> TYPE: PRT
<213> ORGANISM: Artificial Sequence
<220> FEATURE:
<223> OTHER INFORMATION: Localizing sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be Asp or Glu

<400> SEQUENCE: 20

Lys Xaa Xaa
1

<210> SEQ ID NO 21
<211> LENGTH: 4
<212> TYPE: PRT
<213> ORGANISM: Artificial Sequence
<220> FEATURE:
<223> OTHER INFORMATION: Localizing sequence

<400> SEQUENCE: 21

Tyr Gln Arg Leu
1

<210> SEQ ID NO 22
<211> LENGTH: 4
<212> TYPE: PRT
<213> ORGANISM: Artificial Sequence
<220> FEATURE:
<223> OTHER INFORMATION: Proteasome localizing sequence

<400> SEQUENCE: 22

Pro Glu Ser Thr
1
```

<210> SEQ ID NO 23
<211> LENGTH: 351
<212> TYPE: DNA
<213> ORGANISM: Artificial Sequence
<220> FEATURE:
<223> OTHER INFORMATION: VH domain of TH69 antibody (anti-CD7 scFv)

<400> SEQUENCE: 23

```
gaggtgcagc tggtcgaatc tggaggagga ctggtgaagc caggaggatc tctgaaactg      60
agttgtgccg cttcaggcct gaccttctca agctacgcca tgagctgggt gcgacagaca     120
cctgagaagc ggctggaatg ggtcgctagc atctcctctg gcgggttcac atactatcca     180
gactccgtga aaggcagatt tactatctct cgggataacg caagaaatat tctgtacctg     240
cagatgagtt cactgaggag cgaggacacc gcaatgtact attgtgccag ggacgaagtg     300
cgcggctatc tggatgtctg gggagctggc actaccgtca ccgtctccag c              351
```

<210> SEQ ID NO 24
<211> LENGTH: 351
<212> TYPE: DNA
<213> ORGANISM: Artificial Sequence
<220> FEATURE:
<223> OTHER INFORMATION: VL domain of TH69 antibody (anti-CD7 scFv)

<400> SEQUENCE: 24

```
gaggtgcagc tggtcgaatc tggaggagga ctggtgaagc caggaggatc tctgaaactg      60
agttgtgccg cttcaggcct gaccttctca agctacgcca tgagctgggt gcgacagaca     120
cctgagaagc ggctggaatg ggtcgctagc atctcctctg gcgggttcac atactatcca     180
gactccgtga aaggcagatt tactatctct cgggataacg caagaaatat tctgtacctg     240
cagatgagtt cactgaggag cgaggacacc gcaatgtact attgtgccag ggacgaagtg     300
cgcggctatc tggatgtctg gggagctggc actaccgtca ccgtctccag c              351
```

<210> SEQ ID NO 25
<211> LENGTH: 369
<212> TYPE: DNA
<213> ORGANISM: Artificial Sequence
<220> FEATURE:
<223> OTHER INFORMATION: VH domain of 3alf antibody (anti-CD7 scFv)

<400> SEQUENCE: 25

```
caggtccagc tgcaggagtc aggagctgag ctggtgaagc caggggcaag cgtcaaactg      60
tcctgcaagg cctctggata tacattcact agctactgga tgcactgggt gaaacagaga     120
cccggacagg gcctggagtg gatcggaaag attaacccta gcaatggcag gaccaactac     180
aacgaaaagt ttaaatccaa ggcaaccctg acagtggaca gagctcctc tacagcctac     240 atgcagctga gttcactgac ttcagaggat agcgcagtgt actattgcgc cagaggcggg     300
gtctactatg acctgtacta ttacgccctg gattattggg gcagggaac cacagtgact     360 gtcagctcc                                                             369
```

<210> SEQ ID NO 26
<211> LENGTH: 324
<212> TYPE: DNA
<213> ORGANISM: Artificial Sequence
<220> FEATURE:
<223> OTHER INFORMATION: VL domain of 3alf antibody (anti-CD7 scFv)

<400> SEQUENCE: 26

```
gacatcgagc tgacccagag tcctgctaca ctgagcgtga ctccaggcga ttctgtcagt    60
ctgtcatgtc gggcaagcca gtccatctct aacaatctgc actggtacca gcagaaatcc   120
catgaatctc cacgactgct gattaagagt gcctcacaga gcatctccgg cattccctcc   180
cggttctctg gcagtgggtc aggaactgac tttaccctga gtattaactc agtggagaca   240
gaagatttcg gcatgtattt ttgccagcag agcaattcct ggccctacac tttcggaggc   300
gggaccaaac tggagatcaa gcgg                                          324
```

<210> SEQ ID NO 27
<211> LENGTH: 360
<212> TYPE: DNA
<213> ORGANISM: Artificial Sequence
<220> FEATURE:
<223> OTHER INFORMATION: VH domain of T3-4A1 antibody (anti-CD7 scFv)

<400> SEQUENCE: 27

```
gatgtgcagc tggtggagtc tgggggaggc ttagtgcagc ctggagggtc ccggaaactc    60
tcctgtgcag cctctggatt cactttcagt agctttggaa tgcactgggt tcgtcaggct   120
ccagagaagg ggctggagtg ggtcgcatac attagtagtg gcagtagtac cctccactat   180
gcagacacag tgaagggccg attcaccatc tccagagaca atcccaagaa caccctgttc   240
ctgcaaatga ccagtctaag gtctgaggac acggccatgt attactgtgc aagatggggt   300
aactacccct actatgctat ggactactgg ggtcaaggaa cctcagtcac cgtctcctca   360
```

<210> SEQ ID NO 28
<211> LENGTH: 333
<212> TYPE: DNA
<213> ORGANISM: Artificial Sequence
<220> FEATURE:
<223> OTHER INFORMATION: VL domain of T3-4A1 antibody (anti-CD7 scFv)

<400> SEQUENCE: 28

```
gacattgtga tgacccagtc tcctgcttcc ttagctgtat ctctggggca gagggccacc    60
atctcatgca gggccagcaa aagtgtcagt gcatctggct atagttatat gcactggtac   120
caacagaaac caggacagcc acccaaactc ctcatctatc ttgcatccaa cctagaatct   180
ggggtccctg ccaggttcag tggcagtggg tctgggacag acttcaccct caacatccat   240
cctgtggagg aggaggatgc tgtaacctat tactgtcagc acagtaggga gcttccgtac   300
acgttcggag gggggaccaa gctggaaata aaa                                333
```

<210> SEQ ID NO 29
<211> LENGTH: 5
<212> TYPE: PRT
<213> ORGANISM: Artificial Sequence
<220> FEATURE:
<223> OTHER INFORMATION: Polypeptide linker

<400> SEQUENCE: 29

Gly Gly Gly Gly Ser
1               5

<210> SEQ ID NO 30
<211> LENGTH: 63
<212> TYPE: DNA
<213> ORGANISM: Artificial Sequence
<220> FEATURE:
<223> OTHER INFORMATION: CD8alpha signal peptide

```
<400> SEQUENCE: 30
atggctctgc ctgtgaccgc actgctgctg cccctggctc tgctgctgca cgccgcaaga    60
cct                                                                  63

<210> SEQ ID NO 31
<211> LENGTH: 60
<212> TYPE: DNA
<213> ORGANISM: Artificial Sequence
<220> FEATURE:
<223> OTHER INFORMATION: VH-VL Linker

<400> SEQUENCE: 31
ggaggaggag gaagcggagg aggaggatcc ggaggcgggg gatctggagg aggaggaagt    60

<210> SEQ ID NO 32
<211> LENGTH: 42
<212> TYPE: DNA
<213> ORGANISM: Artificial Sequence
<220> FEATURE:
<223> OTHER INFORMATION: ER localization domain, KDEL tethered to scFv
      with myc ("myc KDEL")

<400> SEQUENCE: 32
gagcagaaac tgattagcga agaggacctg aaagatgaac tg                        42

<210> SEQ ID NO 33
<211> LENGTH: 78
<212> TYPE: DNA
<213> ORGANISM: Artificial Sequence
<220> FEATURE:
<223> OTHER INFORMATION: localization domain, "link.(20)AEKDEL"

<400> SEQUENCE: 33
ggtggtggcg gcagtggtgg cggtggctca ggcggtggtg gctccggtgg cggtggctct    60
gcagaaaaag atgagttg                                                   78

<210> SEQ ID NO 34
<211> LENGTH: 249
<212> TYPE: DNA
<213> ORGANISM: Artificial Sequence
<220> FEATURE:
<223> OTHER INFORMATION: localization domain, "mb DEKKMP"

<400> SEQUENCE: 34
accactacac ctgcaccaag gcctcccaca cccgctccca ctatcgcttc ccagccactg    60
tccctgaggc ccgaggcctg caggccagca gctggcggag ccgtgcatac tagggggctg   120
gacttcgctt gcgacatcta catctgggcc ccactggcag gacatgcgg agtcctgctg    180 ctgtccctgg tcatcacact ttacaaatac aaaagcagac gcagttttat tgatgaaaag   240
aaaatgcct                                                            249

<210> SEQ ID NO 35
<211> LENGTH: 126
<212> TYPE: DNA
<213> ORGANISM: Artificial Sequence
<220> FEATURE:
<223> OTHER INFORMATION: Nucleic acid sequence of intracellular
      signaling domain of 4-1BB
```

<400> SEQUENCE: 35

| aagcggggc gcaaaaaact gctgtatatc tttaagcagc ctttcatgag accagtgcag | 60 |
| acaacccagg aggaagatgg gtgctcatgc cggtttcccg aggaggagga aggcggctgc | 120 |
| gagctg | 126 |

<210> SEQ ID NO 36
<211> LENGTH: 336
<212> TYPE: DNA
<213> ORGANISM: Artificial Sequence
<220> FEATURE:
<223> OTHER INFORMATION: intracellular signaling domain of CD3zeta

<400> SEQUENCE: 36

| agggtgaagt ttcccgctc agcagatgct cctgcctacc agcagggcca gaaccagctg | 60 |
| tataatgagc tgaacctggg cagacgcgaa gagtatgatg tgctggacaa aaggcgggga | 120 |
| agagaccccg aaatgggagg gaagccaagg cggaaaaacc cccaggaggg cctgtacaat | 180 |
| gagctgcaga aggacaaaat ggcagaggct tacagtgaga ttgggatgaa gggagagaga | 240 |
| cggagggga aagggcacga tggcctgtac cagggcctga gcacagcaac caaagatact | 300 |
| tatgacgcac tgcacatgca ggcactgcca cccaga | 336 |

<210> SEQ ID NO 37
<211> LENGTH: 204
<212> TYPE: DNA
<213> ORGANISM: Artificial Sequence
<220> FEATURE:
<223> OTHER INFORMATION: Hinge and transmembrane domain of CD8alpha

<400> SEQUENCE: 37

| accactacac ctgcaccaag gcctcccaca cccgctccca ctatcgcttc ccagccactg | 60 |
| tccctgaggc ccgaggcctg caggccagca gctggcggag ccgtgcatac tagggggctg | 120 |
| gacttcgctt gcgacatcta catctgggcc ccactggcag ggacatgcgg agtcctgctg | 180 |
| ctgtccctgg tcatcacact gtac | 204 |

<210> SEQ ID NO 38
<211> LENGTH: 15
<212> TYPE: DNA
<213> ORGANISM: Artificial Sequence
<220> FEATURE:
<223> OTHER INFORMATION: synthetic oligonucleotide primer

<400> SEQUENCE: 38

| atggccgggc ctccg | 15 |

<210> SEQ ID NO 39
<211> LENGTH: 18
<212> TYPE: DNA
<213> ORGANISM: Artificial Sequence
<220> FEATURE:
<223> OTHER INFORMATION: synthetic oligonucleotide primer

<400> SEQUENCE: 39

| tcactggtac tggttggg | 18 |

<210> SEQ ID NO 40
<211> LENGTH: 10
<212> TYPE: PRT
<213> ORGANISM: Artificial Sequence
<220> FEATURE:
<223> OTHER INFORMATION: Localizing domain -continued

```
<400> SEQUENCE: 40

Glu Gln Lys Leu Ile Ser Glu Glu Asp Leu
1               5                   10
```

BLOCKADE OF CD7 EXPRESSION AND CHIMERIC ANTIGEN RECEPTORS FOR IMMUNOTHERAPY OF T-CELL MALIGNANCIES

CROSS-REFERENCE TO RELATED APPLICATIONS

The present application claims the benefit of U.S. Provisional Application No. 62/425,398, filed on Nov. 22, 2016, U.S. Provisional Application No. 62/543,696, filed Aug. 10, 2017, which are expressly incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Nov. 21, 2017, is named 119419-5002-US01 ST25.txt and is 20,928 bytes in size.

BACKGROUND OF THE INVENTION

Chimeric antigen receptors (CARs) can redirect immune cells to specifically recognize and kill tumor cells. CARs are artificial multi-molecular proteins constituted by a single-chain variable region (scFv) of an antibody linked to a signaling molecule via a transmembrane domain. When the scFv ligates its cognate antigen, signal transduction is triggered, resulting in tumor cell killing by CAR-expressing cytotoxic T lymphocytes (Eshhar Z, Waks T, et al. PNAS USA. 90(2):720-724, 1993; Geiger T L, et al. J Immunol. 162(10):5931-5939, 1999; Brentjens R J, et al. Nat Med. 9(3):279-286, 2003; Cooper L J, et al. Blood 101(4):1637-1644, 2003; Imai C, et al. Leukemia. 18:676-684, 2004). Clinical trials with CAR-expressing autologous T lymphocytes have shown positive responses in patients with B-cell refractory leukemia and lymphoma (see, e.g., Till B G, et al. Blood 119(17):3940-3950, 2012; Maude S L, et al. N Engl J Med. 371(16):1507-1517, 2014).

The development of CAR technology to target T cell malignancies has lagged far behind the progress made for their B-cell counterparts. Novel therapies for T-cell malignancies are needed but progress to date has been slow. In particular, effective immunotherapeutic options are lacking and treatment of T-cell acute lymphocytic leukemia (T-ALL) relies on intensive chemotherapy and hematopoietic stem cell transplant. Despite the morbidity and mortality of these approaches, results are far from satisfactory.

In sum, there is a significant unmet need for new therapeutic options for patients with T-cell malignancies.

SUMMARY OF THE INVENTION

In one aspect, the present invention provides an engineered immune cell comprising: (i) a nucleic acid comprising a nucleotide sequence encoding a target-binding molecule linked to a localizing domain, wherein said target-binding molecule is a first antibody that specifically binds to CD7; and (ii) a nucleic acid comprising a nucleotide sequence encoding a chimeric antigen receptor (CAR), wherein said CAR comprises a 4-1BB intracellular signaling domain, a CD3ζ intracellular signaling domain, and a second antibody that specifically binds to CD7.

In some embodiments, the first antibody that specifically binds to CD7 is a first single chain variable fragment (scFv).

In certain embodiments, the second antibody that specifically binds to CD7 is a second single chain variable fragment (scFv).

In some embodiments, the first single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the first single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In certain embodiments, the first single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the localizing domain comprising an amino acid sequence selected from the group consisting of an endoplasmic reticulum (ER) retention sequence, a Golgi retention sequence, a proteasome localizing sequence, and a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some embodiments, the localizing domain comprises an endoplasmic reticulum (ER) retention sequence comprising an amino acid sequence of SEQ ID NO:8 or SEQ ID NO:9. In other embodiments, the localizing domain comprises transmembrane domain sequence derived from CD8a hinge and transmembrane domain sequence comprising an amino acid sequence of SEQ ID NO:13. In some embodiments, proteasome localization of the target-binding molecule (e.g., scFv) is achieved by linking the scFv sequence to a tripartite motif containing 21 (TRIM21) targeting domain sequence and coexpressing a nucleic acid sequence encoding the human TRIM21 E3 ubiquitin ligase protein.

In some embodiments, the 4-1BB intracellular signaling domain comprises an amino acid sequence of SEQ ID NO:3 and wherein the CD3ζ intracellular signaling domain comprises an amino acid sequence of SEQ ID NO:4.

In some embodiments, the hinge and transmembrane domain comprises an amino acid sequence of SEQ ID NO:10.

In some embodiments, the second single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the second single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In yet other embodiments, the second single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the engineered cell is an engineered T cell, an engineered natural killer (NK) cell, an engineered NK/T cell, an engineered monocyte, an engineered macrophage, or an engineered dendritic cell.

In another aspect, the present invention provides an engineered immune cell comprising: (i) a target-binding molecule linked to a localizing domain, wherein said target-binding molecule is a first antibody that specifically binds to CD7; and (ii) a chimeric antigen receptor (CAR), wherein said CAR comprises a 4-1BB intracellular signaling domain, a CD3 intracellular signaling domain, and a second antibody that specifically binds to CD7.

In some embodiments, the first antibody that specifically binds to CD7 is a first single chain variable fragment (scFv). In certain embodiments, the second antibody that specifically binds to CD7 is a second single chain variable fragment (scFv).

In some embodiments, the first single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the first single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In certain embodiments, the first single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the localizing domain comprising an amino acid sequence selected from the group consisting of an endoplasmic reticulum (ER) retention sequence, a Golgi retention sequence, a proteasome localizing sequence, and a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some embodiments, the localizing domain comprises an endoplasmic reticulum (ER) retention sequence comprising an amino acid sequence of SEQ ID NO:8 or SEQ ID NO:9. In other embodiments, the localizing domain comprises transmembrane domain sequence derived from CD8a hinge and transmembrane domain sequence comprising an amino acid sequence of SEQ ID NO:13.

In some embodiments, the 4-1BB intracellular signaling domain comprises an amino acid sequence of SEQ ID NO:3 and wherein the CD3ζ intracellular signaling domain comprises an amino acid sequence of SEQ ID NO:4.

In some embodiments, the hinge and transmembrane domain comprises an amino acid sequence of SEQ ID NO:10.

In some embodiments, the second single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the second single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In yet other embodiments, the second single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the engineered cell is an engineered T cell, an engineered natural killer (NK) cell, an engineered NK/T cell, an engineered monocyte, an engineered macrophage, or an engineered dendritic cell.

In some embodiments, provided herein is a pharmaceutical composition comprising the engineered immune cell described herein and a pharmaceutically acceptable carrier.

In another aspect, the present invention provides methods of producing the engineered immune cell described herein. The method can comprise: (i) introducing into an immune cell (a) a first nucleic acid comprising a nucleotide sequence encoding a target-binding molecule linked to a localizing domain, wherein said target-binding molecule is a first antibody that specifically binds to CD7; and (b) a second nucleic acid comprises a nucleotide sequence encoding a CAR, wherein said CAR comprises a 4-1BB intracellular signaling domain, a CD3ζ intracellular signaling domain, and a second antibody that specifically binds to CD7; and (ii) isolating the engineered immune cell comprising said target-binding molecule linked to said localizing domain and said CAR, thereby producing said engineered immune cell.

In yet another aspect, the present invention provides methods of treating cancer in a subject (e.g., patient) in need thereof, comprising administering a therapeutic amount of an engineered immune cell to said patient, thereby treating cancer in the subject in need thereof. In some embodiments, engineered immune cell comprises: (i) a nucleic acid comprising a nucleotide sequence encoding a target-binding molecule linked to a localizing domain, wherein said target-binding molecule is a first antibody that specifically binds to CD7; and (ii) a nucleic acid comprising a nucleotide sequence encoding a chimeric antigen receptor (CAR), wherein said CAR comprises a 4-1BB intracellular signaling domain, a CD3ζ intracellular signaling domain, and a second antibody that specifically binds to CD7.

In some embodiments, the first antibody that specifically binds to CD7 is a first single chain variable fragment (scFv). In certain embodiments, the second antibody that specifically binds to CD7 is a second single chain variable fragment (scFv).

In some embodiments, the first single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the first single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In certain embodiments, the first single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the localizing domain comprising an amino acid sequence selected from the group consisting of an endoplasmic reticulum (ER) retention sequence, a Golgi retention sequence, a proteasome localizing sequence, and a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some embodiments, the localizing domain comprises an endoplasmic reticulum (ER) retention sequence comprising an amino acid sequence of SEQ ID NO:8 or SEQ ID NO:9. In other embodiments, the localizing domain comprises transmembrane domain sequence derived from CD8a hinge and transmembrane domain sequence comprising an amino acid sequence of SEQ ID NO:13.

In some embodiments, the 4-1BB intracellular signaling domain comprises an amino acid sequence of SEQ ID NO:3 and wherein the CD3ζ intracellular signaling domain comprises an amino acid sequence of SEQ ID NO:4.

In some embodiments, the hinge and transmembrane domain comprises an amino acid sequence of SEQ ID NO:10.

In some embodiments, the second single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the second single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In yet other embodiments, the second single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the engineered cell is an engineered T cell, an engineered natural killer (NK) cell, an engineered NK/T cell, an engineered monocyte, an engineered macrophage, or an engineered dendritic cell.

In some embodiments, the engineered immune cell is administered into said subject (e.g., patient) by intravenous infusion, intra-arterial infusion, intraperitoneal infusion, direct injection into tumor and/or perfusion of tumor bed after surgery, implantation at a tumor site in an artificial scaffold, or intrathecal administration.

In some embodiments, the cancer is a T cell malignancy. In one embodiment, the T cell malignancy is early T cell progenitor acute lymphoblastic leukemia (ETP-ALL).

The present disclosure provides engineered immune cells and methods of use thereof for treating T cell hematologic malignancies. One skilled in the art recognizes that self-killing or fratricide of CAR T-cells and killing of normal T cells can arise when CAR-T effector cells are used to treat T cell leukemias. As such, there is a need for engineered immune cells and therapeutic methods that minimize or eliminate T cell fratricide.

The engineered immune cells and treatment methods described herein utilize novel fratricide-resistant CAR-T cells, such as engineered anti-CD7 PEBL and anti-CD7 CAR-T cells. The engineered immune cells can elicit potent and durable therapeutic effects in patients with T-cell malignancies including relapsed T-cell malignancies. Such cells can result in efficient targeting and killing of malignant T cells without significant effector T cell fratricide.

BRIEF DESCRIPTION OF THE DRAWINGS

FIG. 1A-FIG. 1D illustrate CD7 expression in T-ALL. Percentage of ALL cells expressing CD7 at diagnosis, relapse and during chemotherapy (MRD); the number of bone marrow samples studied at each stage is shown (FIG. 1A). CD7 mean fluorescence intensity (MFI) in T-ALL cells and residual normal T-cells from the same samples (n=19; P<0.0001 by paired t test) (FIG. 1B). CD7 MFI in T-ALL cells at diagnosis or relapse ("Da") and in follow-up bone marrow samples with MRD (n=18) (FIG. 1C). Flow cytometric contour plots illustrate CD7 expression in T-ALL cells (CD3-negative) and normal T cells (CD3-positive) at diagnosis, MRD, and relapse in one representative patient (FIG. 1D).

FIG. 2A-FIG. 2E show the design, expression and signaling of the anti-CD7 CAR. Schema of the anti-CD7-41BB-CD3ζ construct (FIG. 2A). Flow cytometric analysis of Jurkat cells transduced with either GFP alone ("Mock") or GFP plus anti-CD7 CAR. Dot plots illustrate GFP fluorescence, and CAR expression after staining with biotin-conjugated goat anti-mouse F(ab')2 antibody and streptavidin-APC (Jackson ImmunoResearch) (FIG. 2B). Western blot analysis of CAR expression in Jurkat cells (FIG. 2C). Cell lysates of mck- and CAR-transduced Jurkat cells were separated on a 10% polyacrylamide gel under reducing or non-reducing conditions. The blotted membrane was probed with mouse anti-human CD3ζ antibody (8D3; BD Biosciences) and goat anti-mouse IgG conjugated to horseradish peroxidase (R&D Systems). Antibody binding was revealed with Clarity Western ECL Substrate (Bio-Rad). Anti-CD7 CAR induces expression of activation markers upon ligation. Bars show mean (±SD) of CD25 and CD69 MFI in CAR- and mock-transduced Jurkat cells after 24 hours with or without CD7+ MOLT-4 cells. P values by t test are shown for significant differences (*=0.016; ***<0.001) (FIG. 2D). FIG. 2E provides representative flow cytometric histograms of the experiments shown in FIG. 2D.

FIG. 3A-FIG. 3I illustrate expression of anti-CD7 CAR in human peripheral blood T-cells results in fratricide which is prevented by CD7 downregulation. Percentage of viable T cells recovered 24 hours after electroporation with or without anti-CD7 CAR mRNA (n=7) (FIG. 3A). Viable cells were counted by flow cytometry. Percentage of viable T cells recovered 24 hours after CAR transduction with a retroviral vector as compared to cells from the same donors transduced with GFP alone ("Mock") (n=10) (FIG. 3B). Percent of viable CAR- or mock-transduced T cells recovered during the week following transduction (FIG. 3C). Shown are follow-up results for 5 of the 10 experiments shown in FIG. 3B. Percentage of CD107a in T cells after electroporation with or without anti-CD7 CAR mRNA (FIG. 3D). Mean (±SD) of triplicate measurements are shown. Schematic representation of anti-CD7 Protein Expression Blocker (PEBL) constructs (FIG. 3E). Representative flow cytometric histograms illustrate CD7 expression in T-lymphocytes after retroviral transduction of 3 anti-CD7 PEBLs, or mock-transduced GFP alone ("Mock") (FIG. 3F). T-cells were stained with anti-CD7-PE (M-T701; BD Biosciences). Percentage of CD7 expression in T cells retrovirally transduced with the anti-CD7 PEBL-1, or mock-transduced (n=5) (FIG. 3G). Flow cytometric dot plots illustrate downregulation of CD7 expression in T cells by PEBL transduction, together with expression of anti-CD7-41BB-CD3ζ CAR 12 hours after electroporation with or without CAR mRNA (FIG. 3H). Cells were stained with biotin-conjugated goat anti-mouse F(ab')2 antibody and streptavidin-APC (Jackson ImmunoResearch). Percentage of viable T cells transduced with anti-CD7 PEBL recovered 24 hours after electroporation of anti-CD7 CAR mRNA as compared to cells electroporated with the anti-CD7 CAR mRNA but transduced with a vector without anti-CD7 PEBL (n=6) (FIG. 3I). Number of viable cells was measured by flow cytometry. , P<0.01; *, P<0.001.

FIG. 4A-FIG. 4F show that CD7 downregulation by PEBL did not alter T-cell phenotype, proliferation and functionality. Percentage of CD4 and CD8 cells 7-14 days after retroviral transduction with either anti-CD7 PEBL or GFP alone ("Mock") (FIG. 4A). Each symbol corresponds to a different T cell donor. Growth rate of PEBL- and mock-transduced T cells (from 3 donors) maintained with 200 IU/mL IL-2 for 14 days (FIG. 4B). Symbols represent mean (±SD) of triplicate measurements. PEBL- and mock-transduced T cells were electroporated with either anti-CD19-41BB-CD3ζ CAR mRNA or no mRNA (FIG. 4C). Flow cytometric dot plots illustrate GFP and CAR expression 12 hours after electroporation. CAR was detected with biotin-conjugated goat anti-mouse F(ab')2 antibody and streptavidin-APC (Jackson ImmunoResearch). Cytotoxicity of PEBL- or mock-transduced T cells, electroporated with or without anti-CD19 CAR mRNA, against CD19+ ALL cells (OP-1) (FIG. 4D). Bars show mean (±SD) of 4-hour cytotoxicity at a 1:1 E:T. FIG. 4E shows CD107a expression in T cells from experiments identical to those described in FIG. 4D. FIG. 4F shows IFNγ production in PEBL- or mock-transduced T cells, electroporated with or without anti-CD19 CAR mRNA, and co-cultured with OP-1 for 6 hours at E:T 1:1. Bars represent mean (±SD) of triplicate experiments. *, P<0.001; **, P<0.0001.

FIG. 5A-FIG. 5F show T cells with downregulated CD7 by PEBL acquire powerful cytotoxicity against CD7+ leukemic cells after expression of anti-CD7 CAR. Cytotoxicity of anti-CD7 PEBL-transduced T-cells electroporated with or without anti-CD7 CAR mRNA against CD7+ cell lines (FIG. 5A). Shown are data for 4-hour assays at 1:1 E:T. Symbols indicate the mean of 3 measurements each with T cells from 4 donors for MOLT-4, CCRF-CEM and Jurkat, and 5 donors for Loucy and KG1a (P<0.001 for each comparison). Cytotoxicity of anti-CD7 PEBL-transduced T-cells electroporated with or without anti-CD7 CAR mRNA against primary leukemic cells from patients with T-ALL (FIG. 5B). Shown are data for 4-hour assays at the indicated E:T. Symbols refer to mean (±SD) of 3 measurements. FIG. 5C shows overall specific cytotoxicity of T-cells transduced with either anti-CD7 PEBL or GFP alone ("Mock"), after electroporation with anti-CD7 CAR mRNA against the 5 CD7+ cell lines. T cells from 3 donors were tested, at 1:1 E:T, in 4-hour assays. Each symbol represents specific percent cytotoxicity against CD7+ cell line, after subtraction of the percent cytotoxicity obtained with the same T cells electroporated without mRNA. Horizontal bars indicate the median for each group. Anti-CD7 PEBL- or mock-transduced T-cells from 3 donors were electroporated with or without anti-CD7 CAR mRNA (FIG. 5D). Cytotoxicity against MOLT-4 was tested at 1:1 E:T in 4-hour assays. Shown is the mean fluorescence intensity (MFI) of anti-CD107a-PE (H4A3; BD Biosciences). Bars represent mean (±SD) of triplicate experiments. Anti-CD7 PEBL-transduced T-cells were retrovirally transduced with either anti-CD7 CAR or mock-transduced, and tested against primary leukemic cells from patients with T-ALL (FIG. 5E). Each symbol represent mean (±SD) of triplicate experiments. Mock- or PEBL-transduced T-cells, sequentially transduced with or without anti-CD7 CAR, were cultured alone or in presence of Streck-treated MOLT-4 cells, added weekly and 120 IU/mL IL-2 (FIG. 5F). Symbols indicate mean (±SD) percentage of cell recovery relative to number of input cells in triplicate cultures. , P<0.01, *, P<0.001; ****, P<0.0001.

FIG. 6C shows leukemia cell growth in mice shown in FIG. 6A and FIG. 6B expressed as photons per second. Each symbol corresponds to bioluminescence measurements in each mouse, normalised to the average of ventral plus dorsal signals in all mice before CAR-T cell infusion. Kaplan-Meier curves show overall survival of mice in the different groups (8 in each group) (FIG. 6D). Mice were euthanized when the total bioluminescence signal reached $1\times10^{10}$ photons per second. P values calculated by log-rank test.

FIG. 7A-FIG. 7E show PEBL-CAR-T cell activity against ETP-ALL in a patient-derived xenograft (PDX) model. Primary ETP-ALL cells, previously propagated in NOD-SCID-IL2RGnull mice, were infused intravenously (i.v.) in 10 NOD-SCID-IL2RGnull mice at $2\times10^6$ cells per mouse (FIG. 7A). Five mice ("Controls") were left untreated. The remaining 5 mice received a single i.v. infusion of PEBL-CAR T cells ($2\times10^7$ in PEBL-CAR#1, $2\times10^6$ in the remaining 4 mice) at the indicated time point (grey arrow), as well as 20,000 IU IL-2 i.p. every two days; IL-2 was also administered to 2 of the 5 control mice. Black symbols (left y axes) indicate the number of ETP-ALL cells/mL counted in peripheral blood. Grey symbols (right y axes) show numbers of PEBL-CAR T cells. Mice were euthanized when the percentage of ETP-ALL cells among blood mononucleated cells reached ≥80%. Percentage of ETP-ALL (denominator, total human plus mouse CD45+ cells) in various organs of the 5 untreated mice (FIG. 7B). Blood smears of treated (PEBL-CAR#1) and untreated ETP-ALL 7 days after infusion of T cells; smudge cells were prominent in blood after PEBL-CAR T cells (FIG. 7C). Flow cytometric dot plots show the presence of CD7+ CD3− ETP-ALL cells in the tissues of an untreated control mouse with ETP-ALL and of CD7− CD3+ PEBL-CAR T cells in the PEBL-CAR#1 mouse treated with PEBL-CAR-T cells (FIG. 7D). No ETP-ALL (<0.01%) was detected in the treated mouse. Events shown were normalized to the events acquired for the corresponding plots shown in the control mouse. Spleen of treated (PEBL-CAR#1) and untreated mice (FIG. 7E).

FIG. 8A-FIG. 8C show specificity and function of the anti-CD7-41BB-CD3ζ CAR. OP-1 (CD7−) and MOLT-4 (CD7+) were incubated with supernatant collected from Jurkat cells transduced with anti-CD7 scFv, or transduced with a vector containing GFP only ("Control") (FIG. 8A). After washing, cells were incubated with biotin-conjugated goat anti-mouse F(ab')2 antibody followed by streptavidin-APC (Jackson ImmunoResearch). Flow cytometric histograms illustrate binding of the anti-CD7 scFv to MOLT-4 but not OP-1. Jurkat cells were transduced with anti-CD7-41BB-CD3ζ CAR, anti-CD19-41BB-CD3ζ CAR, or a vector containing GFP alone (FIG. 8B). These cells were co-cultured at 1:1 E:T with the CD7+ MOLT-4 or CCRF-CEM cells, or with the CD7− cells OP-1. Target cells were labelled with calcein red-orange AM (Invitrogen). After 30 minutes incubation, the percentage of cell doublets was measured by flow cytometry. Bars illustrate mean (±SD) of triplicate measurements. FIG. 8C shows that CAR-mediated cell aggregation is inhibited by pre-incubating target cells with a soluble form of the anti-CD7 scFv. *** P<0.001.

FIG. 9A provides representative flow cytometric dot plots of T lymphocytes activated for 7 days with Dynabeads Human T-Activator CD3/CD28 (ThermoFisher Scientific) and IL-2, and transduced with the anti-CD7 CAR. Flow cytometric dot plots illustrate GFP fluorescence and CAR expression, the latter revealed by staining with biotin-conjugated goat anti-mouse F(ab')2 antibody followed by streptavidin-APC (Jackson ImmunoResearch). FIG. 9B shows Western blot analysis of CAR expression. Cell lysates of mock- and CAR-transduced T cells were separated on a 10% polyacrylamide gel under reducing or non-reducing conditions. The blotted membrane was probed with a mouse anti-human CD3ζ antibody (8D3; BD Biosciences) followed by goat anti-mouse IgG conjugated to horseradish peroxidase (R&D Systems). Antibody binding was revealed with Clarity Western ECL Substrate (Bio-Rad).

FIG. 10B shows RT-PCR analysis of CD7 mRNA expression. cDNA derived from total mRNA extracted from Jurkat cells transduced with PEBL1-3, GFP alone ("mock"), or untransduced ("WT") was used as template. CD7 cDNA (723 bp) was amplified with the following primers: Forward, ATGGCCGGGC-CTCCG (SEQ ID NO:38), Reverse, TCACTGGTACTGGT-TGGG (SEQ ID NO:39). Electrophoresis was performed on a 1% agarose gel with SYBR Safe Gel Stain (Thermo-Fisher). No template control is also shown. A 87 bp (676-762th nucleotide) region of glyceraldehyde 3-phosphate dehydrogenase (GAPDH) was amplified in parallel as a control.

FIG. 12 shows that CD7-negative T-cells expressing anti-CD7-41BB-CD3ζ CAR exerted anti-tumour cytotoxicity against CD7+ cell lines. Shown are results of 4-hour cytotoxicity assays performed with T cells transduced with anti-CD7 PEBL and then transduced with either CD7-41BB-CD3ζ or GFP only ("Mock"). Symbols represent mean (±SD) of triplicate experiments at the indicated E:T ratios. P<0.001 for all comparisons.

FIG. 13A-FIG. 13E provide functional comparisons of anti-CD7-41BB-CD3ζ and anti-CD19-41BB-CD3ζ CARs. FIG. 13A shows expression of anti-CD19 and anti-CD7 CARs (in an mCherry-containing vector) in peripheral blood T cells previously transduced with anti-CD7 PEBL. Flow cytometry dot plots illustrate mCherry expression and staining of T cells with biotin-conjugated goat anti-mouse F(ab')2 antibody followed by streptavidin conjugated to allophycocyanin (Jackson ImmunoResearch). Results with T cell transduced with a vector containing mCherry alone ("Mock") are also shown. Expression of CD19 in CCRF-CEM and Jurkat cells transduced with a vector containing CD19 and GFP (FIG. 13B). CD19 was detected with anti-CD19 APC (Miltenyi Biotech). Four-hour cytotoxicity assays targeting CD19+ CCRF-CEM or CD19+ Jurkat cells with anti-CD19 or anti-CD7 PEBL-CAR-T cells at different E:T ratios (FIG. 13C). Symbols indicate mean (±SD) of triplicate measurements. P<0.001 for data with either CAR versus mock-transduced T cells at all E:T ratios. Long-term cytotoxicity of anti-CD19 or anti-CD7 PEBL-CAR-T cells at different E:T ratios as measured by live cell image analysis with IncuCyte Zoom System (Essen BioScience) (FIG. 13D). Symbols indicate mean (±SD) of 3 measurements of CD19+ CCRF-CEM (top) or CD19+ Jurkat cells (bottom) in wells containing CAR-T cells, mock-transduced T cells, or no T cells. Measurements were performed at 4-hour intervals. Proliferative capacity of anti-CD19 and anti-CD7 PEBL-CAR-T cells with and without co-culture with CD19+ Jurkat cells (FIG. 13E). Anti-CD7 PEBL-transduced T-cells, sequentially transduced with anti-CD19 or anti-CD7 CARs or mCherry alone, were cultured alone or in presence of irradiated CD19+ Jurkat cells, added weekly and 120 IU/mL IL-2. Symbols indicate mean (±SD) percentage of cell recovery relative to number of input cells in triplicate cultures.

FIG. 15A and FIG. 15B illustrate PEBL-transduced T cells expressing anti-CD7-41BB-CD3ζ CAR exerted anti-tumor activity in mouse models and remained active against cells collected at relapse. FIG. 15A shows percentage of CCRF-CEM cells among white blood cells in blood from NOD-SCID-IL2RGnull mice infused i.v. with CCRF-CEM cells labelled with luciferase and then treated intravenously with either PEBL-CAR-transduced T-cells, mock-transduced T-cells, or RPMI-1640 instead of cells ("Control"), as described for FIG. 6C. For "Control" and "Mock", blood was obtained from euthanized mice that had reached bioluminescence threshold of $10^{10}$ photons/second 17-23 days after leukemia cells infusion. For PEBL-CAR mice, blood was obtained via cheek prick on day 24 after CCRF-CEM infusion. CCRF-CEM cells collected at relapse from the spleen and liver of mice treated with PEBL-CAR were cultured for 2 days (FIG. 15B). They were then used as targets in 4-hour cytotoxicity assay at E:T 1:1 using PEBL-CAR- or mock-transduced T-cells originally used for infusion. Comparison was also made with the same batch of CCRF-CEM-expressing luciferase cells used to generate the xenograft. Percentage cytotoxicity was determined from plate measurements of bioluminescence signal after addition of BrightGlo luciferase assay system (Promega). Bars show mean (±SD) of triplicate measurements; each white and grey bar corresponds to cells from one mouse.

DETAILED DESCRIPTION OF THE INVENTION

A description of example embodiments of the invention follows.

The present invention is based, in part, on the design of a chimeric antigen receptor (CAR) that is directed against CD7, a 40 kDa type I transmembrane glycoprotein which is the primary marker for T cell malignancies, and which is highly expressed in all cases of T cell ALL, including early T-cell progenitor acute lymphoblastic leukemia (ETP-ALL). As described herein, the anti-CD7 CAR induces T cells to exert specific cytotoxicity against T cell malignancies. Further, T cell cytotoxicity was shown to be markedly increased when anti-CD7 CAR was used in combination with downregulation of CD7 expression on the effector T cells. As demonstrated herein, downregulation (e.g., elimination, reduction, and/or relocalization) of CD7 prevented the fratricidal effect exerted by the corresponding anti-CD7 CAR, allowing greater T cell recovery after CAR expression as compared to cells that retained the target antigen (e.g., CD7), and a more effective cytotoxicity against T leukemia/lymphoma cells.

Figure 17:
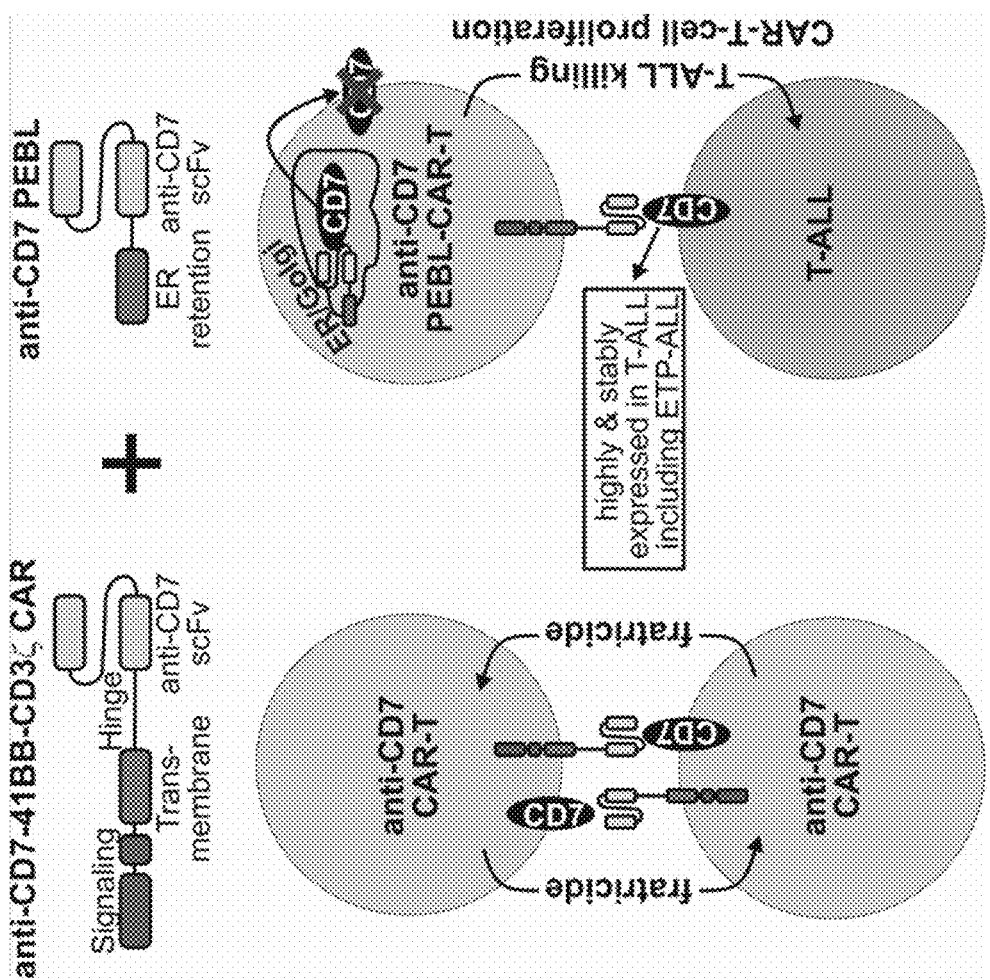
FIG. 17 provides a scheme of an exemplary embodiment of the present invention.

Accordingly, in one aspect, the present invention relates to an engineered immune cell comprising a nucleic acid that comprises a nucleotide sequence encoding a chimeric antigen receptor (CAR), wherein the CAR comprises intracellular signaling domains of 4-1BB and CD3ζ, and an antibody that specifically binds Cluster of Differentiation 7 (CD7). The CAR of the present invention is sometimes referred to herein as "anti-CD7-41BB-CD3ζ". An exemplary embodiment is depicted in FIG. 17

As used herein, an "engineered" immune cell includes an immune cell that has been genetically modified as compared to a naturally-occurring immune cell. For example, an engineered T cell produced according to the present methods carries a nucleic acid comprising a nucleotide sequence that does not naturally occur in a T cell from which it was derived.

In certain embodiments, the engineered immune cell is an engineered T cell, an engineered natural killer (NK) cell, an engineered NK/T cell, an engineered monocyte, an engineered macrophage, or an engineered dendritic cell. In certain embodiments, the engineered immune cell is an engineered T cell. As used herein, the term "nucleic acid" refers to a polymer comprising multiple nucleotide monomers (e.g., ribonucleotide monomers or deoxyribonucleotide monomers). "Nucleic acid" includes, for example, genomic DNA, cDNA, RNA, and DNA-RNA hybrid molecules. Nucleic acid molecules can be naturally occurring, recombinant, or synthetic. In addition, nucleic acid molecules can be single-stranded, double-stranded or triple-stranded. In certain embodiments, nucleic acid molecules can be modified. In the case of a double-stranded polymer, "nucleic acid" can refer to either or both strands of the molecule.

The term "nucleotide sequence," in reference to a nucleic acid, refers to a contiguous series of nucleotides that are joined by covalent linkages, such as phosphorus linkages (e.g., phosphodiester, alkyl and aryl-phosphonate, phosphorothioate, phosphotriester bonds), and/or non-phosphorus linkages (e.g., peptide and/or sulfamate bonds). In certain embodiments, the nucleotide sequence encoding, e.g., a target-binding molecule linked to a localizing domain is a heterologous sequence (e.g., a gene that is of a different species or cell type origin).

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As will be appreciated by those of skill in the art, in some aspects, the nucleic acid further comprises a plasmid sequence. The plasmid sequence can include, for example, one or more sequences of a promoter sequence, a selection marker sequence, or a locus-targeting sequence.

As used herein, "antibody" means an intact antibody or antigen-binding fragment of an antibody, including an intact antibody or antigen-binding fragment that has been modified or engineered, or that is a human antibody. Examples of antibodies that have been modified or engineered are chimeric antibodies, humanized antibodies, multiparatopic antibodies (e.g., biparatopic antibodies), and multispecific antibodies (e.g., bispecific antibodies). Examples of antigen-binding fragments include Fab, Fab', F(ab')2, Fv, single chain antibodies (e.g., scFv), minibodies and diabodies.

The term "specifically (or selectively) binds" or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

In certain embodiments, the antibody that binds CD7 is a single-chain variable fragment antibody ("scFv antibody"). scFv refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun (1994) *The Pharmacology Of Monoclonal Antibodies*, vol. 113, Rosenburg and Moore eds. Springer-Verlag, New York, pp. 269-315. See also, PCT Publication No. WO 88/01649 and U.S. Pat. Nos. 4,946,778 and 5,260,203. As would be appreciated by those of skill in the art, various suitable linkers can be designed and tested for optimal function, as provided in the art, and as disclosed herein.

In certain embodiments, the anti-CD7 scFv comprises a variable heavy chain (heavy chain variable region or VH) and a variable light chain (light chain variable region or VL) having an amino acid sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 1 and 2, respectively. The heavy chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH sequence of SEQ ID NO:1. The light chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VL sequence of SEQ ID NO:2. In some instances, the heavy chain variable region comprise at least one (e.g., 1, 2, 3, 4, 5, 6, 7, 8, 9, 10, or more) amino acid substitution in the sequence set forth in SEQ ID NO:1. In certain instances, the heavy chain variable region comprise 10 or fewer amino acid (e.g., 0, 1, 2, 3, 4, 5, 6, 7, 8, 9, or 10) substitutions in the sequence set forth in SEQ ID NO:1. In some instances, the light chain variable region comprise at least one (e.g., 1, 2, 3, 4, 5, 6, 7, 8, 9, 10, or more) amino acid substitution in the sequence set forth in SEQ ID NO:2. In certain instances, the light chain variable region comprise 10 or fewer amino acid (e.g., 0, 1, 2, 3, 4, 5, 6, 7, 8, 9, or 10) substitutions in the sequence set forth in SEQ ID NO:2. In some embodiments, a nucleic acid sequence encoding a VH comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:23. In other embodiments, a nucleic acid sequence encoding a VL comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:24.

In certain embodiments, the anti-CD7 scFv comprises a variable heavy chain (heavy chain variable region or VH) and a variable light chain (light chain variable region or VL) having a sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 14 and 15, respectively. The heavy chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH sequence of SEQ ID NO:14. The light chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VL sequence of SEQ ID NO:15.

In some instances, the heavy chain variable region comprise at least one (e.g., 1, 2, 3, 4, 5, 6, 7, 8, 9, 10, or more) amino acid substitution in the sequence set forth in SEQ ID NO:14. In certain instances, the heavy chain variable region comprise 10 or fewer amino acid (e.g., 0, 1, 2, 3, 4, 5, 6, 7, 8, 9, 10) substitutions in the sequence set forth in SEQ ID NO:14. In some cases, the light chain variable region comprise at least one (e.g., 1, 2, 3, 4, 5, 6, 7, 8, 9, or more) amino acid substitution in the sequence set forth in SEQ ID NO:15. In certain cases, the heavy chain variable region comprise 10 or fewer amino acid (e.g., 0, 1, 2, 3, 4, 5, 6, 7, 8, 9, 10) substitutions in the sequence set forth in SEQ ID NO:15.

In some embodiments, a nucleic acid sequence encoding a VH comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:25. In other embodiments, a nucleic acid sequence encoding a VL comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:26.

In certain embodiments, the anti-CD7 scFv comprises a variable heavy chain (heavy chain variable region or VH) and a variable light chain (light chain variable region or VL) having a sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 16 and 17, respectively. The heavy chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH sequence of SEQ ID NO:16. The light chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VL sequence of SEQ ID NO:17.

In some instances, the heavy chain variable region comprise at least one (e.g., 1, 2, 3, 4, 5, 6, 7, 8, 9, 10, or more) amino acid substitution in the sequence set forth in SEQ ID NO:16. In certain instances, the heavy chain variable region comprise 13 or fewer amino acid (e.g., 0, 1, 2, 3, 4, 5, 6, 7, 8, 9, 10, 11, 12, or 13) substitutions in the sequence set forth in SEQ ID NO:16. In some cases, the light chain variable region comprise at least one (e.g., 1, 2, 3, 4, 5, 6, 7, 8, 9, 10, or more) amino acid substitution in the sequence set forth in SEQ ID NO:17. In certain cases, the heavy chain variable region comprise 5 or fewer amino acid (e.g., 0, 1, 2, 3, 4, 5, 6, 7, 8, 9, 10, or 11) substitutions in the sequence set forth in SEQ ID NO:17. In some embodiments, a nucleic acid sequence encoding a VH comprises at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:27. In other embodiments, a nucleic acid sequence encoding a VL comprises at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:28.

In some embodiments, the scFv of the present invention comprises a variable heavy chain sequence having at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to a variable heavy chain sequence of an anti-CD7 antibody. In some embodiments, the scFv of the present invention comprises a variable light chain sequence having at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to a variable light chain sequence of an anti-CD7 antibody. For instance, the anti-CD7 antibody can be any such recognized by one skilled in the art.

TABLE 1

Amino acid sequences of VH regions and VL regions of anti-CD7 scFvs

| | Component | Amino Acid Sequence |
|---|---|---|
| TH69 | VH | EVQLVESGGGLVKPGGSLKLSCAASGLTFSSYAMSWVRQTPEKRLEWVA SISSGGFTYYPDSVKGRFTISRDNARNILYLQMSSLRSEDTAMYYCARD EVRGYLDVWGAGTTVTVSS (SEQ ID NO: 1) |
| | VL | AAYKDIQMTQTTSSLSASLGDRVTISCSASQGISNYLNWYQQKPDGTVK LLIYYTSSLHSGVPSRFSGSGSGTDYSLTISNLEPEDIATYYCQQYSKL PYTFGGGTKLEIKR (SEQ ID NO: 2) |
| 3a1f | VH | QVQLQESGAELVKPGASVKLSCKASGYTFTSYWMHWVKQRPGQGLEWIG KINPSNGRTNYNEKFKSKATLTVDKSSSTAYMQLSSLTSEDSAVYYCAR GGVYYDLYYYALDYWGQGTTVTVSS (SEQ ID NO: 14) |
| | VL | DIELTQSPATLSVTPGDSVSLSCRASQSISNNLHWYQQKSHESPRLLIK SASQSISGIPSRFSGSGSGTDFTLSINSVETEDFGMYFCQQSNSWPYTF GGGTKLEIKR (SEQ ID NO: 15) |
| T3-3A1 | VH | DVQLVESGGGLVQPGGSRKLSCAASGFTFSSFGMHWVRQAPEKGLEWVA YISSGSSTLHYADTVKGRFTISRDNPKNTLFLQMTSLRSEDTAMYYCAR WGNYPHYAMDYWGQGTSVTVSS (SEQ ID NO: 16) |
| | VL | DIVMTQSPASLAVSLGQRATISCRASKSVSASGYSYMHWYQQKPGQPPK LLIYLASNLESGVPARFSGSGSGTDFTLNIHPVEEEDAVTYYCQHSREL PYTFGGGTKLEIK (SEQ ID NO: 17) |

TABLE 2

Nucleic acid sequences of VH regions and VL regions of anti-CD7 scFvs

| | Component | Nucleic Acid Sequence |
|---|---|---|
| TH69 | VH | GAGGTGCAGCTGGTCGAATCTGGAGGAGGACTGGTGAAGCCAGGAGGATC<br>TCTGAAACTGAGTTGTGCCGCTTCAGGCCTGACCTTCTCAAGCTACGCCA<br>TGAGCTGGGTGCGACAGACACCTGAGAAGCGGCTGGAATGGGTCGCTAGC<br>ATCTCCTCTGGCGGGTTCACATACTATCCAGACTCCGTGAAAGGCAGATT<br>TACTATCTCTCGGGATAACGCAAGAAATATTCTGTACCTGCAGATGAGTT<br>CACTGAGGAGCGAGGACACCGCAATGTACTATTGTGCCAGGGACGAAGTG<br>CGCGGCTATCTGGATGTCTGGGGAGCTGGCACTACCGTCACCGTCTCCAG<br>C (SEQ ID NO: 23) |
| | VL | GCCGCATACAAGGATATTCAGATGACTCAGACCACAAGCTCCCTGAGCGC<br>CTCCCTGGGAGACCGAGTGACAATCTCTTGCAGTGCATCACAGGGAATTA<br>GCAACTACCTGAATTGGTATCAGCAGAAGCCAGATGGCACTGTGAAACTG<br>CTGATCTACTATACCTCTAGTCTGCACAGTGGGGTCCCCTCACGATTCAG<br>CGGATCCGGCTCTGGGACAGACTACAGCCTGACTATCTCCAACCTGGAGC<br>CCGAAGATATTGCCACCTACTATTGCCAGCAGTACTCCAAGCTGCCTTAT<br>ACCTTTGGCGGGGGAACAAAGCTGGAGATTAAAAGG (SEQ ID<br>NO: 24) |
| 3alf | VH | CAGGTCCAGCTGCAGGAGTCAGGAGCTGAGCTGGTGAAGCCAGGGGCAAG<br>CGTCAAACTGTCCTGCAAGGCCTCTGGATATACATTCACTAGCTACTGGA<br>TGCACTGGGTGAAACAGAGACCCGGACAGGGCCTGGAGTGGATCGGAAAG<br>ATTAACCCTAGCAATGGCAGGACCAACTACAACGAAAAGTTTAAATCCAA<br>GGCAACCCTGACAGTGGACAAGAGCTCCTCTACAGCCTACATGCAGCTGA<br>GTTCACTGACTTCAGAGGATAGCGCAGTGTACTATTGCGCCAGAGGCGGG<br>GTCTACTATGACCTGTACTATTACGCCCTGGATTATTGGGGCAGGGAAC<br>CACAGTGACTGTCAGCTCC (SEQ ID NO: 25) |
| | VL | GACATCGAGCTGACCCAGAGTCCTGCTACACTGAGCGTGACTCCAGGCGA<br>TTCTGTCAGTCTGTCATGTCGGGCAAGCCAGTCCATCTCTAACAATCTGC<br>ACTGGTACCAGCAGAAATCCCATGAATCTCCACGACTGCTGATTAAGAGT<br>GCCTCACAGAGCATCTCCGGCATTCCCTCCCGGTTCTCTGGCAGTGGGTC<br>AGGAACTGACTTTACCCTGAGTATTAACTCAGTGGAGACAGAAGATTTCG<br>GCATGTATTTTTGCCAGCAGAGCAATTCCTGGCCCTACACTTTCGGAGGC<br>GGGACCAAACTGGAGATCAAGCGG (SEQ ID NO: 26) |
| T3-3A1 | VH | GATGTGCAGCTGGTGGAGTCTGGGGGAGGCTTAGTGCAGCCTGGAGGGTC<br>CCGGAAACTCTCCTGTGCAGCCTCTGGATTCACTTTCAGTAGCTTTGGAA<br>TGCACTGGGTTCGTCAGGCTCCAGAGAAGGGGCTGGAGTGGGTCGCATAC<br>ATTAGTAGTGGCAGTAGTACCCTCCACTATGCAGACACAGTGAAGGGCCG<br>ATTCACCATCTCCAGAGACAATCCAAGAACACCCTGTTCCTGCAAATGA<br>CCAGTCTAAGGTCTGAGGACACGGCCATGTATTACTGTGCAAGATGGGGT<br>AACTACCCTCACTATGCTATGGACTACTGGGGTCAAGGAACCTCAGTCAC<br>CGTCTCCTCA (SEQ ID NO: 27) |
| | VL | GACATTGTGATGACCCAGTCTCCTGCTTCCTTAGCTGTATCTCTGGGGCA<br>GAGGGCCACCATCTCATGCAGGGCCAGCAAAAGTGTCAGTGCATCTGGCT<br>ATAGTTATATGCACTGGTACCAACAGAAACCAGGACAGCCACCCAAACTC<br>CTCATCTATCTTGCATCCAACCTAGAATCTGGGGTCCCTGCCAGGTTCAG<br>TGGCAGTGGGTCTGGGACAGACTTCACCCTCAACATCCATCCTGTGGAGG<br>AGGAGGATGCTGTAACCTATTACTGTCAGCACAGTAGGGAGCTTCCGTAC<br>ACGTTCGGAGGGGGGACCAAGCTGGAAATAAAA (SEQ ID NO: 28) |

The term "sequence identity" means that two nucleotide sequences or two amino acid sequences, when optimally aligned, such as by the programs GAP or BESTFIT using default gap weights, share at least, e.g., 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

As those skilled in the art would appreciate, in certain embodiments, any of the sequences of the various components disclosed herein (e.g., scFv, intracellular signaling domain, hinge, linker, localizing sequences, and combinations thereof) can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the specific corresponding sequences disclosed herein. For example, in certain embodiments, the intracellular signaling domain 4-1BB can have at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to SEQ ID NO:3, as long as it possesses the desired function. In certain embodiments, the intracellular signaling domain of 4-1BB comprises the sequence set forth in SEQ ID NO:3 (KRGRKKLLY-IFKQPFMRPVQTTQEEDGCSCRFPEEEEGGCEL).

As another example, in certain embodiments, the intracellular signaling domain 4-1BB can be replaced by another intracellular signaling domain from a co-stimulatory molecule such as CD28, OX40, ICOS, CD27, GITR, HVEM, TIM1, LFA1, or CD2. In some embodiments, the intracellular signaling domain of the CAR can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the intracellular signaling domain of CD28, OX40, ICOS, CD27, GITR, HVEM, TIM1, LFA1, or CD2.

As another example, in certain instances, the intracellular signaling domain of 4-1BB can also include another intracellular signaling domain (or a portion thereof) from a co-stimulatory molecule such as CD28, OX40, ICOS, CD27, GITR, HVEM, TIM1, LFA1, or CD2. In some embodiments, the additional intracellular signaling domain can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the intracellular signaling domain of CD28, OX40, ICOS, CD27, GITR, HVEM, TIM1, LFA1, or CD2. In other embodiments, the additional intracellular signaling domain comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to one or more intracellular signaling domain fragment(s) of CD28, OX40, ICOS, CD27, GITR, HVEM, TIM1, LFA1, or CD2.

As another example, in certain embodiments, the intracellular signaling domain CD3 can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to SEQ ID NO:4, as long as it possesses the desired function. In certain embodiments, the intracellular signaling domain of CD3ζ comprises the sequence set forth in SEQ ID NO:4 (RVKF-SRSADAPAYQQGQNQLYNELNLGRREEYDVLD-KRRGRDPEMGGKPRRKNPQE GLYNELQKDKMAE-AYSEIGMKGERRRGKGHDGLYQGLSTATKDTYDAL HMQALPPR).

In some instances, the intracellular signaling domain comprises an immunoreceptor tyrosine-based activation motif (ITAM) or a portion thereof, as long as it possess the desired function. The intracellular signaling domain of the CAR can include a sequence having at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to an ITAM. In certain embodiments, the intracellular signaling domain can have at least 95% sequence identity, at least 96% sequence identity, at least 97% sequence identity, at least 98% sequence identity, at least 99% sequence identity, or 100% sequence identity to FcεRIγ, CD4, CD7, CD8, CD28, OX40 or H2-Kb, as long as it possesses the desired function.

In certain embodiments, the anti-CD7 CAR further comprises a hinge and transmembrane sequence. Hinge and transmembrane sequences suitable for use in the present invention are known in the art, and provided in, e.g., publication WO2016/126213, incorporated by reference in its entirety. In certain embodiments, the hinge sequence comprises the sequence set forth in SEQ ID NO:5 (TTTPA-PRPPTPAPTIASQPLSLRPEACRPAAGGAVHTRGLD-FACD). In certain embodiments, the transmembrane sequence comprises the sequence set forth in SEQ ID NO:6 (IYIWAPLAGTCGVLLLSLVITLYC). In some embodiments, the hinge and transmembrane domain of the anti-CD7 CAR can be include a signaling domain (e.g., transmembrane domain) from CD8β, 4-1BB, CD28, CD34, CD4, FcεRIγ, CD16, OX40, CD3, CD3ε, CD3γ, CD3δ, TCRα, CD32, CD64, VEGFR2, FAS, FGFR2B, or another transmembrane protein.

In certain embodiments, the anti-CD7 CAR further comprises a CD8a signal peptide (MALPVTALLLPLALLL-HAARP; SEQ ID NO:7). A schematic of the anti-CD7 CAR comprising the embodiments described herein is shown in FIG. 17.

In certain aspects of the present invention, the chimeric antigen receptor (CAR) can bind to a molecule that is expressed on the surface of a cell including, but not limited to members of the CD1 family of glycoproteins, CD2, CD3, CD4, CD5, CD7, CD8, CD25, CD28, CD30, CD38, CD45, CD45RA, CD45RO, CD52, CD56, CD57, CD99, CD127, and CD137.

As described herein, T cell cytotoxicity was shown to be markedly increased when anti-CD7 CAR was used in combination with downregulation of CD7 expression on the effector T cells. As demonstrated herein, downregulation (e.g., elimination, reduction, and/or relocalization) of CD7 prevented the fratricidal effect exerted by the corresponding anti-CD7 CAR, allowing greater T cell recovery after CAR expression as compared to cells that retained the target antigen (e.g., CD7), and a more effective cytotoxicity against T leukemia/lymphoma cells. As those of skill in the art would appreciate, downregulation of CD7 expression on the effector T cells can be achieved according to a variety of known methods including, for example, "intrabodies" against CD7 (as described in WO2016/126213), RNAi against CD7, or gene editing methods such as, e.g., meganucleases, TALEN, CRISPR/Cas9, and zinc finger nucleases.

In certain embodiments, the engineered immune cell further comprises a nucleic acid that comprises a nucleotide sequence encoding a target-binding molecule linked to a localizing domain. The "target-binding molecule linked to a localizing domain" is sometimes referred to herein as a protein expression blocker (PEBL) or in some cases, an "intrabody", as described in WO2016/126213, the teachings of which are incorporated by reference in their entirety. Exemplary embodiments of a PEBL are shown in FIG. 3E and FIG. 17.

As used herein, "linked" in the context of the protein expression blocker refers to a gene encoding a target-binding molecule directly in frame (e.g., without a linker) adjacent to one or more genes encoding one or more localizing domains. Alternatively, the gene encoding a target-binding molecule may be connected to one or more gene encoding one or more localizing domains through a linker sequence, e.g., as described in WO2016/126213. As would be appreciated by those of skill in the art, such linker sequences as well as variants of such linker sequences are known in the art. Methods of designing constructs that incorporate linker sequences as well as methods of assessing functionality are readily available to those of skill in the art.

In certain embodiments, the target-binding molecule is an antibody that binds CD7. In certain embodiments, the antibody is a scFv. In certain embodiments, the scFv comprises a VH sequence set forth in SEQ ID NO:1 and a VL sequence set forth in SEQ ID NO:2. In certain embodiments, the scFv comprises a VH sequence set forth in SEQ ID NO:14 and a VL sequence set forth in SEQ ID NO:15. In certain embodiments, the scFv comprises a VH sequence set forth in SEQ ID NO:16 and a VL sequence set forth in SEQ ID NO:17. As described herein, in certain embodiments, the scFv comprises a VH and a VL having sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 1 and 2, respectively; SEQ ID NO:14 and SEQ ID NO:15, respectively; or SEQ ID NO:16 and SEQ ID NO:17, respectively.

In some embodiments, the nucleic acid sequence of SEQ ID NO:23 encoding an immunoglobulin heavy chain variable region of an anti-CD7 scFv and the nucleic acid sequence of SEQ ID NO:24 encoding an immunoglobulin light chain variable region of an anti-CD7 scFv is used to produce an anti-CD7 protein expression blocker. In other embodiments, the nucleic acid sequence of SEQ ID NO:25 encoding an immunoglobulin heavy chain variable region of an anti-CD7 scFv and the nucleic acid sequence of SEQ ID NO:26 encoding an immunoglobulin light chain variable region of an anti-CD7 scFv is used to produce an anti-CD7 protein expression blocker. In certain embodiments, the nucleic acid sequence of SEQ ID NO:27 encoding an immunoglobulin heavy chain variable region of an anti-CD7 scFv and the nucleic acid sequence of SEQ ID NO:28 encoding an immunoglobulin light chain variable region of an anti-CD7 scFv is used to produce an anti-CD7 protein expression blocker.

In certain embodiments, the antibody that binds CD7 in the context of the CAR, as described herein, can be different from the antibody that binds CD7 in the context of the target-binding molecule (the PEBL). Merely to illustrate, the antibody that binds CD7 in the context of the CAR can comprise a VH sequence set forth in SEQ ID NO:1 and a VL sequence set forth in SEQ ID NO:2, whereas the antibody that binds CD7 in the context of the PEBL can comprise a VH sequence set forth in SEQ ID NO:14 and a VL sequence set forth in SEQ ID NO:15. In certain embodiments, the antibody that binds CD7 in the context of the CAR, as described herein, can be the same as the antibody that binds CD7 in the context of the target-binding molecule (the PEBL).

In certain embodiments, the localizing domain of the PEBL comprises an endoplasmic reticulum (ER) or Golgi retention sequence; a proteosome localizing sequence; a transmembrane domain sequence derived from CD8α, CD8β, 4-1BB, CD28, CD34, CD4, FcεRIγ, CD16, OX40, CD3, CD3ε, CD3γ, CD3δ, TCRα, CD32, CD64, VEGFR2, FAS, or FGFR2B. In certain embodiments, the localizing domain comprises endoplasmic reticulum (ER) retention peptides EQKLISEEDLKDEL (SEQ ID NO:8), (GGGGS)$_4$ AEKDEL (SEQ ID NO:9), or CD8a hinge and transmembrane domain (TTTPAPRPPTPAPTIASQPLSLRPEACR-PAAGGAVHTRGLDFACDIYIWAPLAGTCGVLL LSLVITLY) (SEQ ID NO:10) followed by KYKSRRS-FIDEKKMP (SEQ ID NO:11), as described herein. The localizing domain can direct the PEBL to a specific cellular compartment, such as the Golgi or endoplasmic reticulum, the proteasome, or the cell membrane, depending on the application. The ER or Golgi retention sequence comprises the amino acid sequence KDEL (SEQ ID NO:18); KKXX where X is any amino acid (SEQ ID NO:19); KXD/E (such as KXD or KXE) where X is any amino acid (SEQ ID NO:20); or YQRL (SEQ ID NO:21). The proteasome localizing sequence can comprise a PEST (SEQ ID NO:22) motif.

In some embodiments, proteasome localization is achieved by linking the scFv sequence to a tripartite motif containing 21 (TRIM21) targeting domain sequence and coexpressing the sequence encoding the human TRIM21 E3 ubiquitin ligase protein. TRIM21 binds with high affinity to the Fc domains of antibodies and can recruit the ubiquitin-proteosome complex to degrade molecules (e.g., proteins and peptides) bound to the antibodies. The TRIM21 targeting domain sequence encodes amino acid sequences selected from the group of human immunoglobulin G (IgG) constant regions (Fc) genes such as IgG1, IgG2, or IgG4 and is used to form a fusion protein comprising scFv and Fc domains. In this embodiment, the exogenously expressed TRIM21 protein binds the scFv-Fc fusion protein bound to the target protein (e.g., CD7) and directs the complex to the proteasome for degradation.

Details of the amino acid sequence of the human TRIM21 E3 ligase protein can be found, for example, in NCBI Protein database under NCBI Ref. Seq. No. NP 003132.2. Details of the nucleib acid sequence encoding the human TRIM21 E3 ligase protein can be found, for example, in NCBI Protein database under NCBI Ref. Seq. No. NM_003141.3.

In certain embodiments, the protein expression blocker is any one or more of the anti-CD7 PEBL as disclosed in WO2016/126213, the disclosure is herein incorporated by reference in its entirety for all purposes. Accordingly, the engineered immune cells described herein can comprise an PEBL (a target-binding molecule linked to a localizing domain) that binds to CD7, as described in WO2016/126213. The sequences of the components of anti-CD7 intrabodies as described in FIG. 2, and Tables 1 and 2 of WO2016/126213. Exemplary embodiments of an anti-CD7 PEBL are depicted in FIG. 3E and FIG. 17.

TABLE 3

Amino acid sequence information for select components of anti-CD7 PEBLs

| Component | Sequence |
|---|---|
| CD8α signal peptide | MALPVTALLLPLALLLHAARP (SEQ ID NO:7) |
| VH-VL linker | GGGGSGGGGSGGGGSGGGGS (SEQ ID NO: 12) |
| CD8α hinge and transmembrane domain | TTTPAPRPPTPAPTIASQPLSLRPEACRPAAGGAVHTRGLDFACD IYIWAPLAGTCGVLLLSLVITLY (SEQ ID NO: 10) |
| Localization domain KDEL tethered to scFv with myc ("myc KDEL") | EQKLISEEDLKDEL (SEQ ID NO: 8) |
| Localization domain "link.(20)AEKDEL" | (GGGGS)$_4$AEKDEL (SEQ ID NO: 9) |
| Localization domain "mb DEKKMP" | TTTPAPRPPTPAPTIASQPLSLRPEACRPAAGGAVHTRGLDFACD IYIWAPLAGTCGVLLLSLVITLYKYKSRRSFIDEKKMP (SEQ ID NO: 13) |
| Anti-CD7 scFv VH domain (TH69) | EVQLVESGGGLVKPGGSLKLSCAASGLTFSSYAMSWVRQTPEKRL EWVASISSGGFTYYPDSVKGRFTISRDNARNILYLQMSSLRSEDT AMYYCARDEVRGYLDVWGAGTTVTVSS (SEQ ID NO: 1) |
| Anti-CD7 scFv VL domain (TH69) | AAYKDIQMTQTTSSLSASLGDRVTISCSASQGISNYLNWYQQKPD GTVKLLIYYTSSLHSGVPSRFSGSGSGTDYSLTISNLEPEDIATY YCQQYSKLPYTFGGGTKLEIKR (SEQ ID NO: 2) |

In some embodiments, the anti-CD7 protein expression blocker comprises an amino acid sequence of SEQ ID NO:1, an amino acid sequence of SEQ ID NO:2, and a VH-VL linker. The VH-VL linker can be a (GGGGS)$_n$ linker where n can range from 1 to 6, e.g., 1, 2, 3, 4, 5, or 6. In one embodiment, the anti-CD7 protein expression blocker comprises an amino acid sequence of SEQ ID NO:1, an amino acid sequence of SEQ ID NO:2, and an amino acid sequence of SEQ ID NO:12. In some embodiments, the anti-CD7 protein expression blocker comprises an amino acid sequence having at least 90% sequence identity or at least 95% sequence identity to SEQ ID NO:1, the amino acid sequence of SEQ ID NO:2, and the amino acid sequence of SEQ ID NO:12. In certain embodiments, the anti-CD7 protein expression blocker comprises an amino acid sequence of SEQ ID NO:1, an amino acid sequence having at least 90% sequence identity or at least 95% sequence identity to SEQ ID NO: 2, and an amino acid sequence of SEQ ID NO:12. In other embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, and an amino acid sequence of SEQ ID NO:12. In some instance, the anti-CD7 protein expression blocker also comprises a localization domain selected from any one sequence set forth in SEQ ID NO:8, SEQ ID NO:9, or SEQ ID NO:13. In some cases, the anti-CD7 protein expression blocker also comprises a CD8a signal peptide such as but not limited to the CD8a signal peptide set forth in SEQ ID NO:7. In other cases, the anti-CD7 protein expression blocker also comprises a CD8a hinge and transmembrane domain such as but not limited to the CD8a hinge and transmembrane domain set forth in SEQ ID NO:10.

In some embodiments, the anti-CD7 protein expression blocker comprises an amino acid sequence of SEQ ID NO:14, an amino acid sequence of SEQ ID NO:15, and a VH-VL linker. The VH-VL linker can be a (GGGGS)$_n$ linker where n can range from 1 to 6, e.g., 1, 2, 3, 4, 5, or 6. In one embodiment, the anti-CD7 protein expression blocker comprises an amino acid sequence of SEQ ID NO:14, an amino acid sequence of SEQ ID NO:15, and an amino acid sequence of SEQ ID NO:12. In some embodiments, the anti-CD7 protein expression blocker comprises an amino acid sequence having at least 95% sequence identity to SEQ ID NO:14, the amino acid sequence of SEQ ID NO:15, and the amino acid sequence of SEQ ID NO:12. In certain embodiments, the anti-CD7 protein expression blocker comprises an amino acid sequence of SEQ ID NO:14, an amino acid sequence having at least 95% sequence identity to SEQ ID NO:15, and an amino acid sequence of SEQ ID NO:12. In other embodiments, the anti-CD7 protein expression blocker comprises an amino acid sequence having at least 90% sequence identity or at least 95% sequence identity to SEQ ID NO:14, an amino acid sequence having at least 90% sequence identity or at least 95% sequence identity to SEQ ID NO:5, and an amino acid sequence of SEQ ID NO:12. In some instance, the anti-CD7 protein expression blocker also comprises a localization domain selected from any one sequence set forth in SEQ ID NO:8, SEQ ID NO:9, or SEQ ID NO:13. In some cases, the anti-CD7 protein expression blocker also comprises a CD8a signal peptide such as but not limited to the CD8a signal peptide set forth in SEQ ID NO:7. In other cases, the anti-CD7 protein expression blocker also comprises a CD8a hinge and transmembrane domain such as but not limited to the CD8a hinge and transmembrane domain set forth in SEQ ID NO:10.

In some embodiments, the anti-CD7 protein expression blocker comprises an amino acid sequence of SEQ ID NO:16, an amino acid sequence of SEQ ID NO:17, and a VH-VL linker. The VH-VL linker can be a (GGGGS)$_n$ linker where n can range from 1 to 5, e.g., 1, 2, 3, 4, 5, or 6 (SEQ ID NO:29). In one embodiment, the anti-CD7 protein expression blocker comprises an amino acid sequence of SEQ ID NO:16, an amino acid sequence of SEQ ID NO:17, and an amino acid sequence of SEQ ID NO:12. In some embodiments, the anti-CD7 protein expression blocker comprises an amino acid sequence having at least 90% sequence identity or at least 95% sequence identity to SEQ ID NO:16, the amino acid sequence of SEQ ID NO:17, and the amino acid sequence of SEQ ID NO:12. In certain embodiments, the anti-CD7 protein expression blocker comprises an amino acid sequence of SEQ ID NO:16, an amino acid sequence having at least 90% sequence identity or at least 95% sequence identity to SEQ ID NO:17, and an amino acid sequence of SEQ ID NO:12. In other embodiments, the anti-CD7 protein expression blocker comprises an amino acid sequence having at least 90% sequence identity or at least 95% sequence identity to SEQ ID NO:16, an amino acid sequence having at least 90% sequence identity or at least 95% sequence identity to SEQ ID NO:17, and an amino acid sequence of SEQ ID NO:12. In some instance, the anti-CD7 protein expression blocker also comprises a localization domain selected from any one sequence set forth in SEQ ID NO:8, SEQ ID NO:9, or SEQ ID NO:13. In some cases, the anti-CD7 protein expression blocker also comprises a CD8a signal peptide such as but not limited to the CD8a signal peptide set forth in SEQ ID NO:7. In other cases, the anti-CD7 protein expression blocker also comprises a CD8a hinge and transmembrane domain such as but not limited to the CD8a hinge and transmembrane domain set forth in SEQ ID NO:10.

In some embodiments, the nucleic acid sequence encoding an anti-CD7 PEBL comprises one or more nucleic acid sequences set forth in Table 4. In some embodiments, the VH domain of the anti-CD7 scFv of the PEBL comprises the nucleotide sequence of SEQ ID NO:23 and the VL domain of the anti-CD7 scFv of the PEBL comprises the nucleotide sequence of SEQ ID NO:24. In certain embodiments, the VH domain of the anti-CD7 scFv of the PEBL comprises the nucleotide sequence having at least 90% sequence identity (e.g., 90%, 91%, 92%, 93%, 94%, 95%, 96%, 97%, 98%, 99%, or more sequence identity) to SEQ ID NO:23 and the VL domain of the anti-CD7 scFv of the PEBL comprises the nucleotide sequence having at least 90% sequence identity (e.g., 90%, 91%, 92%, 93%, 94%, 95%, 96%, 97%, 98%, 99%, or more sequence identity) to SEQ ID NO:24.

In some embodiments, the nucleic acid sequence encoding the localization domain of the anti-CD7 protein expression blocker comprises a sequence selected from SEQ ID NO:32, SEQ ID NO:33, or SEQ ID NO:34, or a codon optimized variant thereof.

In certain aspects of the present invention, the protein expression blocker can bind to a molecule that is expressed on the surface of a cell including, but not limited to members of the CD1 family of glycoproteins, CD2, CD3, CD4, CD5, CD7, CD8, CD25, CD28, CD30, CD38, CD45, CD45RA, CD45RO, CD52, CD56, CD57, CD99, CD127, and CD137.

In some aspects of the present invention, expression of a member of the CD1 family of glycoproteins, CD2, CD3, CD4, CD5, CD7, CD8, CD25, CD28, CD30, CD38, CD45, CD45RA, CD45RO, CD52, CD56, CD57, CD99, CD127, or CD137 can be downregulated using a gene editing method, such as, but not limited to, a gene editing technology that employs meganucleases, TALEN, CRISPR/Cas9, or zinc finger nucleases. For example, in some embodiments, CD7 expression is knocked out using genome editing by Cas9/CRISPR. In other embodiments, CD5 expression is knocked out using genome editing by Cas9/CRISPR.

As noted above, downregulation of CD7 expression on the effector T cells can be achieved according to a variety of other known methods including, for example, gene editing methods with meganucleases, TALEN, CRISPR/Cas9, and zinc finger nucleases. Thus, in certain embodiments, the engineered immune cell further comprises a modified CD7 gene, which modification renders the CD7 gene or protein non-functional. By way of example, the engineered immune cell of the present invention further comprises a modified (e.g., non-functional) CD7 gene (modified using, e.g., meganucleases, TALEN, CRISPR/Cas9, or zinc finger nucleases) that prevents or reduces expression of CD7, and/or otherwise impairs (e.g., structurally) the CD7 protein from being

TABLE 4

Nucleic acid sequence information for select components of an anti-CD7 PEBL based on TH69

| Component | Sequence |
| --- | --- |
| CD8α signal peptide | ATGGCTCTGCCTGTGACCGCACTGCTGCTGCCCCTGGCTCTGC TGCTGCACGCCGCAAGACCT (SEQ ID NO: 30) |
| Anti-CD7 scFv VL (1H69) | GCCGCATACAAGGATATTCAGATGACTCAGACCACAAGCTCCC TGAGCGCCTCCCTGGGAGACCGAGTGACAATCTCTTGCAGTGC ATCACAGGGAATTAGCAACTACCTGAATTGGTATCAGCAGAAG CCAGATGGCACTGTGAAACTGCTGATCTACTATACCTCTAGTC TGCACAGTGGGGTCCCCTCACGATTCAGCGGATCCGGCTCTGG GACAGACTACAGCCTGACTATCTCCAACCTGGAGCCCGAAGAT ATTGCCACCTACTATTGCCAGCAGTACTCCAAGCTGCCTTATA CCTTTGGCGGGGGAACAAAGCTGGAGATTAAAAGG (SEQ ID NO: 24) |
| Anti-CD7 scFv VH (TH69) | GAGGTGCAGCTGGTCGAATCTGGAGGAGGACTGGTGAAGCCAG GAGGATCTCTGAAACTGAGTTGTGCCGCTTCAGGCCTGACCTT CTCAAGCTACGCCATGAGCTGGGTGCGACAGACACCTGAGAAG CGGCTGGAATGGGTCGCTAGCATCTCCTCTGGCGGGTTCACAT ACTATCCAGACTCCGTGAAAGGCAGATTTACTATCTCTCGGGA TAACGCAAGAAATATTCTGTACCTGCAGATGAGTTCACTGAGG AGCGAGGACACCGCAATGTACTATTGTGCCAGGGACGAAGTGC GCGGCTATCTGGATGTCTGGGGAGCTGGCACTACCGTCACCGT CTCCAGC (SEQ ID NO: 25) |
| VH-VL Linker | GGAGGAGGAGGAAGCGGAGGAGGAGGATCCGGAGGCGGGGGAT CTGGAGGAGGAGGAAGT (SEQ ID NO: 31) |
| ER localization domain KDEL tethered to scFv with myc ("myc KDEL") | GAGCAGAAACTGATTAGCGAAGAGGACCTGAAAGATGAACTG (SEQ ID NO: 32) | recognized by an anti-CD7 CAR. Methods of modifying gene expression using such methods are readily available and well-known in the art.

Methods of inactivating a target gene in an immune cell using CRISPR/Cas6 technology are described, for example, in US Patent Publication Nos. 2016/0272999, 2017/0204372, and 2017/0119820.

The CRISPR/Cas system is a system for inducing targeted genetic alterations (genome modifications). Target recognition by the Cas9 protein requires a "seed" sequence within the guide RNA (gRNA) and a conserved multinucleotide containing protospacer adjacent motif (PAM) sequence upstream of the gRNA-binding region. The CRISPR/Cas system can thereby be engineered to cleave substantially any DNA sequence by redesigning the gRNA in cell lines, primary cells, and engineered cells. The CRISPR/Cas system can simultaneously target multiple genomic loci by co-expressing a single Cas9 protein with two or more gRNAs, making this system uniquely suited for multiple gene editing or synergistic activation of target genes. Examples of a CRISPR/Cas system used to inhibit gene expression are described in U.S. Publication No. 2014/0068797 and U.S. Pat. Nos. 8,697,359 and 8,771,945. The system induces permanent gene disruption that utilizes the RNA-guided Cas9 endonuclease to introduce DNA double stranded breaks which trigger error-prone repair pathways to result in frame shift mutations. In some cases, other endonucleases may also be used, including but not limited to, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, T7, Fok1, other nucleases known in the art, homologs thereof, or modified versions thereof.

CRISPR/Cas gene disruption occurs when a gRNA sequence specific for a target gene and a Cas endonuclease are introduced into a cell and form a complex that enables the Cas endonuclease to introduce a double strand break at the target gene. In some instances, the CRISPR system comprises one or more expression vectors comprising a nucleic acid sequence encoding the Cas endonuclease and a guide nucleic acid sequence specific for the target gene. The guide nucleic acid sequence is specific for a gene and targets that gene for Cas endonuclease-induced double strand breaks. The sequence of the guide nucleic acid sequence may be within a loci of the gene. In some embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40, 45, 50, or more nucleotides in length. The guide nucleic acid sequence includes a RNA sequence, a DNA sequence, a combination thereof (a RNA-DNA combination sequence), or a sequence with synthetic nucleotides, such as a peptide nucleic acid (PNA) or Locked Nucleic Acid (LNA). The guide nucleic acid sequence can be a single molecule or a double molecule. In one embodiment, the guide nucleic acid sequence comprises a single guide RNA.

In some embodiments, the engineered immune cell of the present invention can be modified via the CRISPR/Cas system to inactivate the human CD7 gene. Details of the genomic structure and sequence of the human CD7 gene can be found, for example, in NCBI Gene database under GeneID No. 924.

Commercially available kits, gRNA vectors and donor vectors, for knockout of specific target genes are available, for example, from Origene (Rockville, Md.), GenScript (Atlanta, Ga.), Applied Biological Materials (ABM; Richmond, British Colombia), BioCat (Heidelberg, Germany) or others. For example, commercially available kits or kit components for knockout of CD7 via CRISPR include, for example, those available as catalog numbers KN201231, KN201231G1, KN201231G2, and KN201231D, each available from OriGene, and those available as catalog numbers sc-4072847, sc-4072847-KO-2, sc-4072847-HDR-2, sc-4072847-NIC, sc-4072847HDR-2, and sc-4072847-NIC-2, each available from Santa Cruz Biotechnology.

In some embodiments, the chimeric antigen receptor described herein can be introduced into the human CD7 gene locus using the CRISPR/Cas system.

In certain embodiments, provided is an engineered immune cell comprising: i) a nucleic acid that comprises a nucleotide sequence encoding a chimeric antigen receptor (CAR), wherein the CAR comprises intracellular signaling domains of 4-1BB and CD3ζ, and an antibody that specifically binds Cluster of Differentiation 7 (CD7); and ii) a nucleic acid that comprises a nucleotide sequence encoding a target-binding molecule linked to a localizing domain, wherein the target-binding molecule is an antibody that binds CD7, and the localizing domain comprises an endoplasmic reticulum retention sequence. In certain embodiments, the antibody that binds CD7 in the context of the CAR, as well as in the context of the target-binding molecule comprises: a VH sequence set forth in SEQ ID NO: 1 and a VL sequence set forth in SEQ ID NO: 2; a VH sequence set forth in SEQ ID NO: 14 and a VL sequence set forth in SEQ ID NO: 15; or a VH sequence set forth in SEQ ID NO: 16 and a VL sequence set forth in SEQ ID NO: 17. As described herein, in certain embodiments, the antibody comprises a VH and a VL having sequence that each comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 1 and 2, respectively; SEQ ID NO: 14 and SEQ ID NO: 15, respectively; or SEQ ID NO: 16 and SEQ ID NO: 17, respectively. In certain embodiments, the antibody that binds CD7 in the context of the CAR can be different from the antibody that binds CD7 in the context of the target-binding molecule (the protein expression blocker or PEBL), as described herein. In certain embodiments, the intracellular signaling domain of 4-1BB comprises the sequence set forth in SEQ ID NO: 3. In certain embodiments, the intracellular signaling domain of CD3ζ comprises the sequence set forth in SEQ ID NO: 4.

In another aspect, also provided is a nucleic acid comprising a nucleotide sequence encoding a CAR, wherein the CAR comprises intracellular signaling domains of 4-1BB and CD3ζ, and an antibody that binds CD7, as described herein.

In certain embodiments, the antibody is a scFv. In certain embodiments, the scFv comprises a VH sequence set forth in SEQ ID NO: 1 and a variable light chain VL sequence set forth in SEQ ID NO: 2. In certain embodiments, the scFv comprises a VH sequence set forth in SEQ ID NO: 14 and a variable light chain VL sequence set forth in SEQ ID NO: 15. In certain embodiments, the scFv comprises a VH sequence set forth in SEQ ID NO: 16 and a variable light chain VL sequence set forth in SEQ ID NO: 17. As described herein, in certain embodiments, the scFv comprises a VH and a VL having sequence that each comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 1 and 2, respectively; SEQ ID NO: 14 and SEQ ID NO: 15, respectively; or SEQ ID NO: 16 and SEQ ID NO: 17, respectively. In certain embodiments, the CAR further comprises a hinge and transmembrane sequence.

In certain embodiments, an isolated nucleic acid of the present invention comprises a nucleotide sequence that encodes a CAR according to Table 5. In some embodiments, the nucleic acid comprises a nucleotide sequence that encodes a component of the CAR according to Table 5.

TABLE 5

Amino acid sequence information for select components of an anti-CD7 CAR

| Component | Amino Acid Sequence |
|---|---|
| Anti-CD7 VH (TH69) | EVQLVESGGGLVKPGGSLKLSCAASGLTFSSYAMSWVRQTPEKRLEWVASIS SGGFTYYPDSVKGRFTISRDNARNILYLQMSSLRSEDTAMYYCARDEVRGYL DVWGAGTTVTVSS (SEQ ID NO: 1) |
| Anti-CD7 VL (TH69) | AAYKDIQMTQTTSSLSASLGDRVTISCSASQGISNYLNWYQQKPDGTVKLLI YYTSSLHSGVPSRFSGSGSGTDYSLTISNLEPEDIATYYCQQYSKLPYTFGG GTKLEIKR (SEQ ID NO: 2) |
| Intracellular signaling domain of 4-1BB | KRGRKKLLYIFKQPFMRPVQTTQEEDGCSCRFPEEEEGGCEL (SEQ ID NO: 3) |
| Intracellular signaling domain CD3 | RVKFSRSADAPAYQQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPR (SEQ ID NO: 4) |
| Hinge and transmembrane domain of CD8α | TTTPAPRPPTPAPTIASQPLSLRPEACRPAAGGAVHTRGLDFACDIYIWAPL AGTCGVLLLSLVITLY (SEQ ID NO: 10) |

In some embodiments, the anti-CD7 CAR comprises an amino acid sequence of SEQ ID NO:1, an amino acid sequence of SEQ ID NO:2, a 4-1BB intracellular signaling domain, a CD3ζ intracellular signaling domain, and a CD8 hinge and transmembrane domain. In some embodiments, the anti-CD7 CAR also includes a VH-VL linker such as but not limited to a (GGGGS)$_n$ linker where n can range from 1 to 6, e.g., 1, 2, 3, 4, 5, or 6.

In one embodiment, the anti-CD7 protein expression blocker comprises an amino acid sequence of SEQ ID NO:1, an amino acid sequence of SEQ ID NO:2, an amino acid sequence of SEQ ID NO:3, an amino acid sequence of SEQ ID NO:4, and an amino acid sequence of SEQ ID NO:10. In some embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, an amino acid sequence of SEQ ID NO:3, an amino acid sequence of SEQ ID NO:4, and an amino acid sequence of SEQ ID NO:10. In some embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, an amino acid sequence having at least 90% sequence identity or at least 95% sequence identity to SEQ ID NO:3, an amino acid sequence of SEQ ID NO:4, and an amino acid sequence of SEQ ID NO:10. In some embodiments, the anti-CD7 protein expression blocker comprises an amino acid sequence having at least 90% sequence identity to SEQ ID NO:1, an amino acid sequence having at least 90% sequence identity or at least 95% sequence identity to SEQ ID NO:2, an amino acid sequence of SEQ ID NO:3, an amino acid sequence having at least 90% sequence identity or at least 95% sequence identity to SEQ ID NO:4, and an amino acid sequence of SEQ ID NO:10. In some embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, an amino acid sequence of SEQ ID NO:3, an amino acid sequence of SEQ ID NO:4, and an amino acid sequence having at least 90% sequence identity or at least 95% sequence identity to SEQ ID NO:10. In some embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, an amino acid sequence having at least 90% sequence identity or at least 95% sequence identity to SEQ ID NO:3, an amino acid sequence having at least 90% sequence identity or at least 95% sequence identity to SEQ ID NO:4, and an amino acid sequence having at least 90% sequence identity or at least 95% sequence identity to SEQ ID NO:10.

In certain embodiments, an isolated nucleic acid of the present invention comprises one or more nucleotide sequences of Table 6. In some embodiments, the nucleic acid comprises a nucleotide sequence of a component of the CAR as set forth in Table 6.

TABLE 6

Amino acid sequence information for select components of an anti-CD7 CAR

| Component | Nucleic Acid Sequence |
|---|---|
| Anti-CD7 VH (TH69) | GAGGTGCAGCTGGTCGAATCTGGAGGAGGACTGGTGAAGCCAGGAGGATCTC TGAAACTGAGTTGTGCCGCTTCAGGCCTGACCTTCTCAAGCTACGCCATGAG CTGGGTGCGACAGACACCTGAGAAGCGGCTGGAATGGGTCGCTAGCATCTCC TCTGGCGGGTTCACATACTATCCAGACTCCGTGAAAGGCAGATTTACTATCT CTCGGGATAACGCAAGAAATATTCTGTACCTGCAGATGAGTTCACTGAGGAG CGAGGACACCGCAATGTACTATTGTGCCAGGGACGAAGTGCGCGGCTATCTG GATGTCTGGGGAGCTGGCACTACCGTCACCGTCTCCAGC (SEQ ID NO: 23) |
| Anti-CD7 VL (TH69) | GCCGCATACAAGGATATTCAGATGACTCAGACCACAAGCTCCCTGAGCGCCT CCCTGGGAGACCGAGTGACAATCTCTTGCAGTGCATCACAGGGAATTAGCAA CTACCTGAATTGGTATCAGCAGAAGCCAGATGGCACTGTGAAACTGCTGATC TACTATACCTCTAGTCTGCACAGTGGGGTCCCCTCACGATTCAGCGGATCCG GCTCTGGGACAGACTACAGCCTGACTATCTCCAACCTGGAGCCCGAAGATAT TGCCACCTACTATTGCCAGCAGTACTCCAAGCTGCCTTATACCTTTGGCGGG GGAACAAAGCTGGAGATTAAAAGG (SEQ ID NO: 24) |
| Intracellular signaling domain of 4-1BB | AAGCGGGGCGCAAAAAACTGCTGTATATCTTTAAGCAGCCTTTCATGAGAC CAGTGCAGACAACCCAGGAGGAAGATGGGTGCTCATGCCGGTTTCCCGAGGA GGAGGAAGGCGGCTGCGAGCTG (SEQ ID NO: 35) |
| Intracellular signaling domain of CD3 | AGGGTGAAGTTTTCCCGCTCAGCAGATGCTCCTGCCTACCAGCAGGGCCAGA ACCAGCTGTATAATGAGCTGAACCTGGGCAGACGCGAAGAGTATGATGTGCT GGACAAAAGGCGGGGAAGAGACCCCGAAATGGGAGGGAAGCCAAGGCGGAAA AACCCCCAGGAGGGCCTGTACAATGAGCTGCAGAAGGACAAAATGGCAGAGG CTTACAGTGAGATTGGGATGAAGGGAGAGAGACGGAGGGGAAAAGGGCACGA TGGCCTGTACCAGGGGCTGAGCACAGCAACCAAAGATACTTATGACGCACTG CACATGCAGGCACTGCCACCCAGA (SEQ ID NO: 36) |
| Hinge and transmembrane domain of CD8α | ACCACTACACCTGCACCAAGGCCTCCCACACCCGCTCCCACTATCGCTTCCC AGCCACTGTCCCTGAGGCCCGAGGCCTGCAGGCCAGCAGCTGGCGGAGCCGT GCATACTAGGGGGCTGGACTTCGCTTGCGACATCTACATCTGGGCCCCACTG GCAGGGACATGCGGAGTCCTGCTGCTGTCCCTGGTCATCACACTGTAC (SEQ ID NO: 37) |

In certain embodiments, a nucleic acid further comprises a nucleotide sequence that encodes a target-binding molecule linked to a localizing domain, as described herein. In certain embodiments, the target-binding molecule is an antibody that binds CD7. In certain embodiments, the antibody is a scFv. In some embodiments, the scFv comprises a VH sequence having at least 90% sequence identity (e.g., 90%, 91%, 92%, 93%, 94%, 95%, 96%, 97%, 98%, 99%, or more sequence identity) to the sequence of SEQ ID NO: 1 and a VL sequence having at least 90% sequence identity (e.g., 90%, 91%, 92%, 93%, 94%, 95%, 96%, 97%, 98%, 99%, or more sequence identity) to the sequence of SEQ ID NO: 2. In certain embodiments, the scFv comprises a VH sequence set forth in SEQ ID NO: 1 and a VL sequence set forth in SEQ ID NO: 2. In some embodiments, the VH domain of the anti-CD7 scFv comprises the nucleotide sequence of SEQ ID NO:23 and the VL domain of the anti-CD7 scFv comprises the nucleotide sequence of SEQ ID NO:24.

In other aspects, also provided is a method of treating cancer in a subject in need thereof, comprising administering a therapeutic amount of an engineered immune cell having any of the embodiments described herein to the subject, thereby treating cancer in a subject in need thereof.

In certain embodiments, the method comprises administering a therapeutic amount of an engineered immune cell comprising a nucleic acid that comprises a nucleotide sequence encoding a CAR, wherein the CAR comprises intracellular signaling domains of 4-1BB and CD3ζ, and an antibody that binds CD7, as described herein.

In certain embodiments, the method comprises administering a therapeutic amount of an engineered immune cell that further comprises a nucleic acid having a nucleotide sequence encoding a target-binding molecule linked to a localizing domain, as described herein (e.g., an anti-CD7 protein expression blocker).

In certain embodiments, the cancer is a T cell malignancy, e.g., T cell leukemia or T cell lymphoma, such a T-cell acute lymphoblastic leukemia, T-cell prolymphocytic leukemia, T-cell large granular lymphocytic leukemia, enteropathy-associated T-cell lymphoma, hepatosplenic T-cell lymphoma, subcutaneous panniculitis-like T-cell lymphoma, mycosis fungoides, Sézary syndrome, primary cutaneous gamma-delta T-cell lymphoma, peripheral T-cell lymphoma not otherwise specified, angioimmunoblastic T-cell lymphoma, anaplastic large cell lymphoma. In certain embodiments, the T cell malignancy is early T-cell progenitor acute lymphoblastic leukemia (ETP-ALL).

As used herein, the terms "treat," "treating," or "treatment," refer to counteracting a medical condition (e.g., a condition related to a T cell malignancy) to the extent that the medical condition is improved according to a clinically-acceptable standard.

As used herein, "subject" refers to a mammal (e.g., human, non-human primate, cow, sheep, goat, horse, dog, cat, rabbit, guinea pig, rat, mouse). In certain embodiments, the subject is a human. A "subject in need thereof" refers to a subject (e.g., patient) who has, or is at risk for developing, a disease or condition that can be treated (e.g., improved, ameliorated, prevented) by inducing T cells to exert specific cytotoxicity against malignant T cells.

As defined herein, a "therapeutic amount" refers to an amount that, when administered to a subject, is sufficient to achieve a desired therapeutic effect (treats a condition related to a T cell malignancy) in the subject under the conditions of administration. An effective amount of the agent to be administered can be determined by a clinician of ordinary skill using the guidance provided herein and other methods known in the art, and is dependent on several factors including, for example, the particular agent chosen, the subject's age, sensitivity, tolerance to drugs and overall well-being.

In some embodiments, the engineered immune cell is autologous to the subject in need of treatment, e.g., cancer treatment. In other embodiments, the engineered immune cell is allogenic to the subject in need of treatment.

In certain embodiments, the engineered immune cell is administered into the subject by intravenous infusion, intra-arterial infusion, direct injection into tumor and/or perfusion of tumor bed after surgery, implantation at a tumor site in an artificial scaffold, intrathecal administration, and intraocular administration.

In certain embodiments, the engineered immune cell is administered by infusion into the subject. Methods of infusing immune cells (e.g., allogeneic or autologous immune cells) are known in the art. A sufficient number of cells are administered to the recipient in order to ameliorate the symptoms of the disease. Typically, dosages of $10^7$ to $10^{10}$ cells are infused in a single setting, e.g., dosages of $10^9$ cells. Infusions are administered either as a single $10^9$ cell dose or divided into several $10^9$ cell dosages. The frequency of infusions can be daily, every 2 to 30 days or even longer intervals if desired or indicated. The quantity of infusions is generally at least 1 infusion per subject and preferably at least 3 infusions, as tolerated, or until the disease symptoms have been ameliorated. The cells can be infused intravenously at a rate of 50-250 ml/hr. Other suitable modes of administration include intra-arterial infusion, intraperitoneal infusion, direct injection into tumor and/or perfusion of tumor bed after surgery, implantation at the tumor site in an artificial scaffold, intrathecal administration. Methods of adapting the present invention to such modes of delivery are readily available to one skilled in the art.

In certain embodiments, the method of treating cancer according to the present invention is combined with at least one other known cancer therapy, e.g., radiotherapy, chemotherapy, or other immunotherapy.

In other aspects, also provided is use of an engineered immune cell having any of the embodiments described herein for treating cancer, comprising administering a therapeutic amount of the engineered immune cell to a subject in need thereof. In certain embodiments, the cancer is a T cell malignancy. In certain embodiments, the T cell malignancy is early T-cell progenitor acute lymphoblastic leukemia (ETP-ALL).

In certain embodiments, the engineered immune cell is administered into the subject by intravenous infusion, intra-arterial infusion, intraperitoneal infusion, direct injection into tumor and/or perfusion of tumor bed after surgery, implantation at a tumor site in an artificial scaffold, and intrathecal administration.

In another aspect, also provided is a method for producing the engineered immune cell having any of the embodiments described herein, the method comprising introducing into an immune cell a nucleic acid that comprises a nucleotide sequence encoding a CAR, wherein the CAR comprises intracellular signaling domains of 4-1BB and CD3ζ, and an antibody that binds CD7.

In certain embodiments, the method further comprises introducing into the immune cell a nucleic acid that comprises a nucleotide sequence encoding a target-binding molecule linked to a localizing domain (e.g., anti-CD7 protein expression blocker or anti-CD7 PEBL). In certain embodiments, the nucleotide sequence encoding CAR and the nucleotide sequence encoding the anti-CD7 PEBL are introduced on a single plasmid.

In various aspects, also provided is a kit for producing an engineered immune cell described herein. The present kit can be used to produce, e.g., allogeneic or autologous T cells having anti-CD7 CAR-mediated cytotoxic activity. In some embodiments, the kit is useful for producing allogeneic effector T cells having anti-CD7 CAR-mediated cytotoxic activity. In certain embodiments, the kit is useful for producing autologous effector T cells having anti-CD7 CAR-mediated cytotoxic activity.

Accordingly, provided herein is a kit comprising a nucleic acid comprising a nucleotide sequence encoding a CAR, wherein the CAR comprises intracellular signaling domains of 4-1BB and CD3ζ, and an antibody that binds CD7. The nucleotide sequence encoding the anti-CD7 CAR can be designed according to any of the embodiments described herein. In certain embodiments, the nucleotide sequence encodes the anti-CD7 CAR according to the schematic in FIG. 1A ("anti-CD7-41BB-CD3ζ construct").

In certain embodiments, the kit further comprises a nucleic acid having a nucleotide sequence that encodes a target-binding molecule linked to a localizing domain, as described herein (e.g., anti-CD7 PEBL molecules described herein). The nucleotide sequence encoding the target-binding molecule linked to a localizing domain can be designed according to any of the embodiments described herein.

In certain embodiments, the nucleotide sequence encoding the anti-CD7 CAR and/or the nucleotide sequence encoding the anti-CD7 PEBL further comprise sequences (e.g., plasmid or vector sequences) that allow, e.g., cloning and/or expression. For example, the nucleotide sequence can be provided as part of a plasmid for ease of cloning into other plasmids and/or vectors (expression vectors or viral expression vectors) for, e.g., transfection, transduction, or electroporation into a cell (e.g., an immune cell). In certain embodiments, the nucleotide sequence encoding the anti-CD7 CAR and the nucleotide sequence encoding the anti-CD7 PEBL are provided on a single plasmid or vector (e.g., a single construct comprising an anti-CD7 CAR and an anti-CD7 PEBL). In certain embodiments, the nucleotide sequences are provided on separate plasmids or vectors (expression vectors or viral expression vectors).

Typically, the kits are compartmentalized for ease of use and can include one or more containers with reagents. In certain embodiments, all of the kit components are packaged together. Alternatively, one or more individual components of the kit can be provided in a separate package from the other kits components. The kits can also include instructions for using the kit components.

In some embodiments, provided herein is an engineered immune cell comprising a nucleic acid that comprises a nucleotide sequence encoding a chimeric antigen receptor (CAR), wherein the CAR comprises intracellular signaling domains of 4-1BB and CD3ζ, and an antibody that binds Cluster of Differentiation 7 (CD7). In certain embodiments, the antibody is a single chain variable fragment (scFv). In some instances, the scFv comprises a heavy chain variable domain (VH) sequence set forth in SEQ ID NO: 1 and a light chain variable domain (VL) sequence set forth in SEQ ID NO: 2.

In some embodiments, the CAR further comprises a hinge and transmembrane sequence, such as but not limited to a hinge and transmembrane domain comprising the amino acid sequence of SEQ ID NO:10.

In some embodiments, the engineered immune cell is an engineered T cell, an engineered natural killer (NK) cell, an engineered NK/T cell, an engineered monocyte, an engineered macrophage, or an engineered dendritic cell.

In some embodiments, the engineered immune cell further comprising a nucleic acid that comprises a nucleotide sequence encoding a target-binding molecule linked to a localizing domain. In certain embodiments, the target-binding molecule is an antibody that binds CD7. In certain embodiments, the antibody is an scFv. In some embodiments, the scFv comprises a VH sequence set forth in SEQ ID NO: 1 and a VL sequence set forth in SEQ ID NO: 2. In some embodiments, the localizing domain comprises an endoplasmic reticulum (ER) or Golgi retention sequence; a proteosome localizing sequence; a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B.

In some embodiments, provided herein is an engineered immune cell comprising: (i) a nucleic acid that comprises a nucleotide sequence encoding a chimeric antigen receptor (CAR), wherein the CAR comprises intracellular signaling domains of 4-1BB and CD3ζ, and an antibody that binds Cluster of Differentiation 7 (CD7); and (ii) a nucleic acid that comprises a nucleotide sequence encoding a target-binding molecule linked to a localizing domain, wherein the target-binding molecule is an antibody that binds CD7, and the localizing domain comprises an endoplasmic reticulum retention sequence, and wherein the antibody that binds CD7 comprises a variable heavy chain (VH) sequence set forth in SEQ ID NO: 1 and a variable light chain (VL) sequence set forth in SEQ ID NO: 2. In some embodiments, the intracellular signaling domain of 4-1BB comprises the sequence set forth in SEQ ID NO: 3 and the intracellular signaling domain of CD3ζ comprises the sequence set forth in SEQ ID NO: 4.

In some embodiments, provided herein is an method of treating cancer in a subject in need thereof, comprising administering a therapeutic amount of the engineered immune cell described herein to the subject, thereby treating cancer in a subject in need thereof. In some embodiments, the cancer is a T cell malignancy. In certain embodiments, the T cell malignancy is early T-cell progenitor acute lymphoblastic leukemia (ETP-ALL). In certain embodiments, the engineered immune cell is administered into the subject by intravenous infusion, intra-arterial infusion, intraperitoneal infusion, direct injection into tumor and/or perfusion of tumor bed after surgery, implantation at a tumor site in an artificial scaffold, intrathecal administration.

In some embodiments, provided herein is a nucleic acid comprising a nucleotide sequence encoding a chimeric antigen receptor (CAR), wherein the CAR comprises intracellular signaling domains of 4-1BB and CD3ζ, and an antibody that binds Cluster of Differentiation 7 (CD7).

In other embodiments, provided herein is the of the engineered immune cell described herein for treating cancer comprising administering a therapeutic amount of the engineered immune cell to a subject in need thereof. In some embodiments, the cancer is a T cell malignancy. In certain embodiments, the T cell malignancy is early T-cell progenitor acute lymphoblastic leukemia (ETP-ALL). In certain embodiments, the engineered immune cell is administered into the subject by intravenous infusion, intra-arterial infusion, intraperitoneal infusion, direct injection into tumor and/or perfusion of tumor bed after surgery, implantation at a tumor site in an artificial scaffold, intrathecal administration.

In some embodiments, provided herein is a method for producing the engineered immune cell described herein. The method can include: introducing into an immune cell a nucleic acid that comprises a nucleotide sequence encoding a CAR, wherein the CAR comprises intracellular signaling domains of 4-1BB and CD3ζ, and an antibody that binds CD7, thereby producing an engineered immune cell. The method can further comprise introducing into the immune cell a nucleic acid that comprises a nucleotide sequence encoding a target-binding molecule linked to a localizing domain.

The present invention provides a chimeric antigen receptor (CAR) directed against CD7. As demonstrated herein, the expression of the anti-CD7 CAR in immune cells such as effector T cells, induces the T cell to exert specific cytotoxicity against T cell malignancies. This cytotoxic effect was shown to be enhanced when expression of CD7 on the effector T cells was downregulated using an antibody-based molecule (a protein expression blocker or PEBL) that targeted the CD7 for downregulation. Thus, the present invention provides an immunotherapeutic method for treating cancers, e.g., T-cell malignancies.

In some aspects, the present invention provides an engineered immune cell comprising a nucleic acid that comprises a nucleotide sequence encoding a chimeric antigen receptor (CAR), wherein the CAR comprises intracellular signaling domains of 4-1BB and CD3ζ, and an antibody that binds Cluster of Differentiation 7 (CD7). In some embodiments, the engineered immune cell outlined herein also includes a nucleic acid that comprises a nucleotide sequence encoding a target-binding molecule linked to a localizing domain (e.g., a protein expression blocker or PEBL). Outlined herein is also a method and kit for producing such an engineered immune cell.

In some aspects, the present invention provides an engineered immune cell (e.g., T cell, natural killer (NK) cell, NK/T cell, monocyte, macrophage, or dendritic cell) comprising (i) a nucleic acid that comprises a nucleotide sequence encoding a chimeric antigen receptor (CAR), wherein the CAR comprises intracellular signaling domains of 4-1BB and CD3ζ, and an antibody that specifically binds CD7; and (ii) a nucleic acid that comprises a nucleotide sequence encoding a target-binding molecule linked to a localizing domain, wherein the target-binding molecule is an antibody that binds CD7, and the localizing domain comprises an endoplasmic reticulum retention sequence, and wherein the antibody that binds CD7 comprises a variable heavy chain (VH) sequence set forth in SEQ ID NO: 1 and a variable light chain (VL) sequence set forth in SEQ ID NO: 2.

In other aspects, the present invention provides a method of treating cancer (e.g., a T cell malignancy) in a subject in need thereof. The method includes administering a therapeutic amount of any of the engineered immune cells described herein to the subject, thereby treating cancer in a subject in need thereof. The disclosure also sets forth the use of any of the engineered immune cells outlined herein for treating cancer.

In other aspects, the present invention provides a nucleic acid comprising a nucleotide sequence encoding a chimeric antigen receptor (CAR), wherein the CAR comprises intracellular signaling domains of 4-1BB and CD3, and an antibody that specifically binds CD7.

EXAMPLES

Example 1: Blockade of CD7 Expression in T Cells for Effective Chimeric Antigen-Receptor Targeting of T-Cell Malignancies This example illustrates blockade of CD7 expression with a novel method, combined with a second-generation CAR, resulted in highly potent anti-CD7 CAR-T cells. This practical strategy provides a new treatment option for patients with high-risk T-cell malignancies, including ETP-ALL.

Abstract

Effective immunotherapies for T-cell malignancies are lacking. A novel approach based on chimeric antigen receptor (CAR)-redirected T lymphocytes was devised. CD7 was selected as a target because of its consistent expression in T-cell acute lymphoblastic leukemia (T-ALL), including the most aggressive subtype, early T-cell precursor (ETP)-ALL. In 49 diagnostic T-ALL samples (including 14 ETP-ALL), median CD7 expression was >99%; CD7 expression remained high at relapse (n=14), and during chemotherapy (n=54). CD7 was targeted with a second-generation CAR (anti-CD7-41BB-CD3ζ) but CAR expression in T lymphocytes caused fratricide, owing to CD7 present in the T cells themselves. To downregulate CD7 and control fratricide, a new method (Protein Expression Blocker, PEBL), based on an anti-CD7 single chain variable fragment coupled with an intracellular retention domain was applied. Transduction of anti-CD7 PEBL resulted in virtually instantaneous abrogation of surface CD7 expression in all transduced T cells; 2.0%±1.7% were CD7+ versus 98.1%±1.5% of mock-transduced T cells (n=5; P<0.0001). PEBL expression did not impair T-cell proliferation, IFNγ and TNFα secretion, or cytotoxicity, and eliminated CAR-mediated fratricide. PEBL-CAR-T cells were highly cytotoxic against CD7+ leukemic cells in vitro, and were consistently more potent than CD7+ T cells spared by fratricide. They also showed strong anti-leukemic activity in cell line- and patient-derived T-ALL xenografts. The strategy described here fits well with existing clinical-grade cell manufacturing processes, and can be rapidly implemented for the treatment of patients with high-risk T-cell malignancies.

Introduction

T lymphocytes can be induced to specifically recognize and kill tumor cells through the expression of chimeric antigen receptors (CARs).[1-5] Central to the effective application of this technology is the identification of a suitable target for the CAR. This must be highly expressed by tumor cells and should be absent in normal cells, or be expressed only by normal cells whose temporary absence is clinically manageable.[6] Thus, leukemias and lymphomas of B-cell origin can be targeted with CARs directed against CD19,[5,7] or CD22,[8] which are normally expressed only by B lymphoid cells.[9,10] Infusion of autologous T cells expressing anti-CD19 CARs in patients with B-cell refractory leukemia and lymphoma resulted in major clinical responses.[11-18] These exciting results have provided indisputable evidence of the power of this technology, and suggest the possibility of wider applications in oncology.

The development of CAR-T cell therapies for T-cell malignancies has lagged far behind that of their B-cell counterparts. The need for effective therapies in this area is particularly urgent because of the poor prognosis associated with some T-cell leukemia and lymphoma subtypes. For example, children and adolescents with early T-cell progenitor acute lymphoblastic leukemia (ETP-ALL) have the poorest response to initial therapy among all patients with ALL.[19-21] Intensive chemotherapy and/or allogeneic hematopoietic stem cell transplant often do not prevent treatment-refractory relapse; for these patients, and those with other high-risk features, such as adult age, there is a dearth of treatment options.[19,22-25]

A major obstacle to the development of effective CAR-T cells for T-cell malignancies is that the surface marker profile of malignant T cells (which generally lack CD19 or CD22 expression) largely overlaps that of activated T lymphocytes.[19,26] CAR directed against such targets are likely to lead to the self-elimination of the CAR-T cells.[27,28] Described herein is the development and application of a practical technology for CAR-T cell therapy of ETP-ALL and other T-ALL cell subtypes. First, a CAR directed against CD7 was made. As one recognizes, CD7 is a 40 kDa type I transmembrane glycoprotein that is a primary marker for T-cell malignancies,[29-32] and is highly expressed in all cases of T-cell ALL, including ETP-ALL.[19] Second, a method to rapidly and effectively downregulate CD7 expression in T cells was developed. The method was selected as it averts the fratricide effect of CAR-T cell therapy, does not involve gene editing, and can be immediately translated into clinical applications.

Materials and Methods

Cells and Culture Conditions

The leukemia cell lines Jurkat, CCRF-CEM, Loucy, MOLT4 and KG1a were from the American Type Culture Collection (ATCC; Rockville, Md.). The B-lineage ALL cell line OP-1 was developed in our laboratory.[33] The CCRF-CEM cells were transduced with a murine stem cell virus (MSCV)-internal ribosome entry site (IRES)-green fluorescent protein (GFP) retroviral vector (from the Vector Development and Production Shared Resource of St. Jude Children's Research Hospital, Memphis, Tenn.) containing the firefly luciferase gene. The same vector was used to transduce CCRF-CEM and Jurkat cells with the CD19 gene, which was cloned from the cDNA of the RS4; 11 B-cell line (ATCC). Cell lines were maintained in RPMI-1640 (ThermoFisher Scientific, Waltham, Mass.) supplemented with 10% fetal bovine serum (FBS) and 1% penicillin-streptomycin.

Peripheral blood samples were obtained from discarded anonymized by-products of platelet donations from healthy adult donors at the National University Hospital Blood Bank, Singapore. Bone marrow aspirates from patients with ALL were obtained for diagnostic immunophenotyping, and monitoring of treatment response,[19,26] banked surplus material was used in some experiments, with approval from the Institutional Review Board, National University of Singapore. Mononucleated cells were separated by centrifugation on a Lymphoprep density step (Axis-Shield, Oslo, Norway) and washed twice in RPMI-1640. T cells were enriched with Dynabeads Human T-Activator CD3/CD28 (ThermoFisher) and cultured in RPMI-1640, 10% FBS, 1% penicillin-streptomycin, and interleukin-2 (IL-2; 120 IU/mL; Proleukin, Novartis, Basel, Switzerland).

Gene Cloning and Retroviral Transduction

The single chain variable fragment (scFv) of the anti-CD7 monoclonal antibody TH69[34] was joined to the CD8α signal peptide, CD8α hinge and transmembrane domain, and the intracellular domains of 4-1BB and CD3ζ of an anti-CD19-41BB-CD3ζ CAR previously developed in our laboratory.[5] The same scFv was also joined to the CD8α signal peptide and sequences encoding endoplasmic reticulum (ER)/Golgi retention peptides EQKLISEEDLKDEL (SEQ ID NO:8), (GGGGS)$_4$AEKDEL (SEQ ID NO:9), or CD8α hinge and transmembrane domain followed by localizing sequence (SEQ ID NO:13). These were subcloned into the MSCV vector, with or without GFP or mCherry.

Preparation of retroviral supernatant and transduction were performed as previously described.[5,35] Briefly, pMSCV retroviral vector-conditioned medium was added to RetroNectin (Takara, Otsu, Japan)-coated polypropylene tubes; after centrifugation and removal of the supernatant, T cells were added to the tubes and left at 37° C. for 12 hours; fresh viral supernatant was added on two other successive days. T lymphocytes were maintained in RPMI-1640 with FBS, antibiotics and 200 IU/mL IL-2.

For transient CAR expression, anti-CD7 and anti-CD19 CAR constructs were subcloned into EcoRI and XhoI sites of the pVAXI vector (ThermoFisher Scientific), and transcribed into mRNA using T7 mScript (CellScript, Madison, Wis.).[36] For mRNA electroporation, cells were suspended in electroporation buffer (Amaxa Cell Line Nucleofector Kit V; Lonza, Basel, Switzerland) containing 200 μg of CAR mRNA, and electroporated with an Amaxa Nucleofector 2b (Lonza) using program X-001.[36,37] Cells electroporated without mRNA were used as control.

Detection of CAR, PEBL and Surface Markers

CARs were detected with a biotin-conjugated goat anti-mouse F(ab')2 antibody (Jackson ImmunoResearch, West Grove, Pa.) followed by allophycocyanin (APC)-conjugated streptavidin (Jackson ImmunoResearch). Phycoerythrin (PE)- or APC-conjugated anti-CD7 (M-T701), CD4 (RPA-T4), CD8 (RPA-T8), CD3 (SK7), and non-reactive isotype-matched antibodies were from BD Biosciences (San Jose, Calif.); CD19 (LT19) was from Miltenyi Biotech. Cell staining was analyzed using Accuri C6, Fortessa or LSRII flow cytometers (BD Biosciences), with Diva (BD Biosciences) or FlowJo software (FlowJo, Ashland, Oreg.).

Western blotting was performed as previously described.[35] Briefly, cell lysates were extracted using CelLytic M cell lysis reagent (Sigma-Aldrich, Saint Louis, Mo.) prior to protein quantification with Pierce BCA protein assay kit (ThermoFisher). Cell lysates were diluted with 4× Laemmli sample buffer (Bio-rad, Hercules, Calif.) and separated on 10% polyacrylamide gel by electrophoresis under reducing or non-reducing conditions. Blotted membranes were probed with mouse anti-human CD3ζ antibody (8D3; BD Biosciences), goat anti-mouse IgG horseradish peroxidase-conjugated (R&D Systems, Minneapolis, Minn.), and Clarity Western ECL substrate (Bio-Rad). Staining was visualised using ChemiDoc Touch Imager (Bio-Rad).

Cell Aggregation Assay, Cytotoxicity Assays and Cytokine Production

To measure cell-cell aggregation, Jurkat cells were co-cultured with the CD7+ or CD7− cells labeled with calcein red-orange AM (ThermoFisher) for 30 minutes; cell doublets were counted by flow cytometry. In some experiments, target cells were pre-incubated for 10 minutes before co-culture with a soluble anti-CD7 scFv, obtained from the supernatant of Jurkat or 293T cells transduced with a construct consisting of the scFv without transmembrane or signaling sequences.

To test cytotoxicity, target cells were labeled with calcein red-orange AM and placed into a 96-well round bottom plate (Corning Costar, Corning, N.Y.). T cells were added at different effector:target (E:T) ratios with target cells and cultured for 4 hours at 37° C. and 5% CO2. Viable target cells were counted by flow cytometry.[38] To measure exocytosis of lytic granules, anti-human CD107a-PE (H4A3; BD Biosciences) was added to the co-cultures. After 1 hour, monensin (BD GolgiStop) was added, and the cultures were continued for another 3 hours before flow cytometric analysis.

To assess cell proliferation, T-cells were cultured alone or in presence of MOLT-4 cells at 1:1 E:T in RPMI-1640 with FBS and 120 IU/mL IL-2 at 37° C. and 5% CO2. Target cells, irradiated or treated with Streck cell preservative (Streck Laboratories, Omaha, Nebr.) to inhibit proliferation, were added to the cultures every 7 days. Viable GFP+ or mCherry+ T-cells were enumerated by flow cytometry. For IFNγ and TNFα production, target and effector cells at 1:1 E:T were plated as above. After 1 hour, brefeldin A (BD GolgiPlug) was added to the cultures, which continued for another 5 hours. Subsequently, intracellular staining with anti-IFNγ-PE (clone 25723.11; BD Biosciences) or anti-TNFα-PE (6401.1111; BD Biosciences) was done prior to flow cytometric analysis.

Xenograft Models

CCRF-CEM cells transduced with luciferase were injected intravenously (i.v.) in NOD.Cg-Prkdc$^{scid}$IL2rg$^{tm1Wjl}$/SzJ (NOD/scid IL2RGnull) mice (Jackson Laboratory, Bar Harbor, Me.) at 1×10$^6$ cells per mouse. Three and/or seven days later, mice received T cells with downregulated CD7 and anti-CD7 CAR expression at 2×10$^7$ T cells per mouse. Other mice received T cells transduced with GFP alone, or RPMI-1640 with 10% FBS instead of T cells. All mice received 20,000 IU of IL-2 intraperitoneally (i.p.) every 2 days. Tumor load was determined using the Xenogen IVIS-200 System (Caliper Life Sciences, Waltham, Mass.) after injecting aqueous D-luciferin potassium salt (Perkin Elmer, Waltham, Mass.) i.p. (2 mg per mouse). Luminescence was analyzed with the Living Image 3.0 software. Mice were euthanized when luminescence reached 1×10$^{10}$ photons per second, or earlier if physical signs warranting euthanasia appeared.

For the patient-derived xenograft (PDX) model, primary ETP-ALL cells were injected i.v. in NOD/scid IL2RGnull and propagated for 7-8 subsequent generations. ETP-ALL cells were then re-injected in NOD/scid IL2RGnull which were either treated with PEBL-CAR-T cells or left untreated. Peripheral blood and tissues were monitored for the presence of ALL cells by flow cytometry.[19,26] After red blood cells lysis with a lysing buffer (Sigma-Aldrich), cells were stained with anti-mouse CD45-PE-Cyanine 7 (30-F11, Biolegend), as well as anti-human CD45-APC-H7 (2D1), CD7-PE (M-T701), CD3 APC (SK7), CD34-peridinin chlorophyll protein (8G12) (all from BD Biosciences), and CD33-Brilliant Violet 421 (WM53, Biolegend). Cells were analyzed with a Fortessa flow cytometer, using Diva and FlowJo software.

Results

Validation of CD7 as a Target for CAR-T Cell Therapy in Leukemia

In leukemic cells from diagnostic bone marrow samples obtained from 49 patients with T-ALL (including 14 with ETP-ALL), median percent CD7 expression was >99% (range, 79%->99%). In only 3 cases (6.1%), CD7 was lower than 99%: 98% in two, and 79% in one (FIG. 1A). High CD7 expression was also observed in samples collected from 14 patients with relapse T-ALL (FIG. 1A). Mean fluorescence intensity (MFI) of CD7 in leukemic cells at diagnosis or relapse consistently exceeded that measured in residual normal T cells in the same samples. Median (range) MFI was 20,617 (4,105-66,674) in T-ALL cells versus 3,032 (1,301-9,582) in the normal T cells (n=19; P<0.0001) (FIG. 1B).

To determine whether chemotherapy affected CD7 expression, bone marrow samples collected during therapy that contained minimal residual disease (MRD) were examined. In all 54 samples (from 21 patients), >99% of residual leukemic cells were CD7+(FIG. 1A). In 18 patients, CD7 levels were monitored during the course of the disease. As shown in FIG. 1C and FIG. 1D, CD7 remained high during therapy. These results validate CD7 as a target for CAR-T cell therapy in T-ALL.

Design and Expression of an Anti-CD7 CAR

To target CD7, an anti-CD7 CAR composed of the scFv of the anti-CD7 antibody TH69 joined to the signaling domains of 4-1BB (CD137) and CD3ζ via the hinge and transmembrane domain of CD8α (FIG. 2A) was designed. Retroviral transduction of this construct in Jurkat cells resulted in high expression of anti-CD7 CAR (FIG. 2B), which appeared as monomer, dimer and oligomer by western blotting (FIG. 2C).

To confirm that the TH69 scFv could bind CD7, it was produced in soluble form and was tested on CD7+ MOLT-4 and CD7− OP-1 cells; MOLT-4 cells were labelled while OP-1 were not (FIG. 8A). Further, staining with an anti-CD7 monoclonal antibody was significantly reduced when MOLT-4 cells were pre-incubated with the anti-CD7 scFv supernatant; CD7 MFI (±SD) went from 31,730±1,144 to 5,987±241 (n=3). Jurkat cells expressing anti-CD7 CAR formed aggregates with CD7+ MOLT-4 cells, whereas those transduced with GFP only, or with an anti-CD19 CAR, did not; conversely, the anti-CD19 CAR induced cell aggregation with CD19+ OP-1 cells while the anti-CD7 CAR did not (FIG. 8B). Pre-incubation of MOLT-4 or CCRF-CEM with the soluble anti-CD7 scFv prevented the formation of aggregates (FIG. 8C).

To determine whether the anti-CD7 CAR was functional, levels of the activation markers CD25 and CD69 were measured in Jurkat cells after 24-hour co-culture with MOLT4. There was a clear upregulation of both activation markers in cells expressing the anti-CD7 CAR (FIGS. 2D and 2E). In sum, the anti-CD7-41BB-CD3ζ CAR can bind to its cognate antigen, and transduces activation signals upon ligation.

Expression of Anti-CD7 CAR in T Cells Causes Fratricide

Figure 9B:
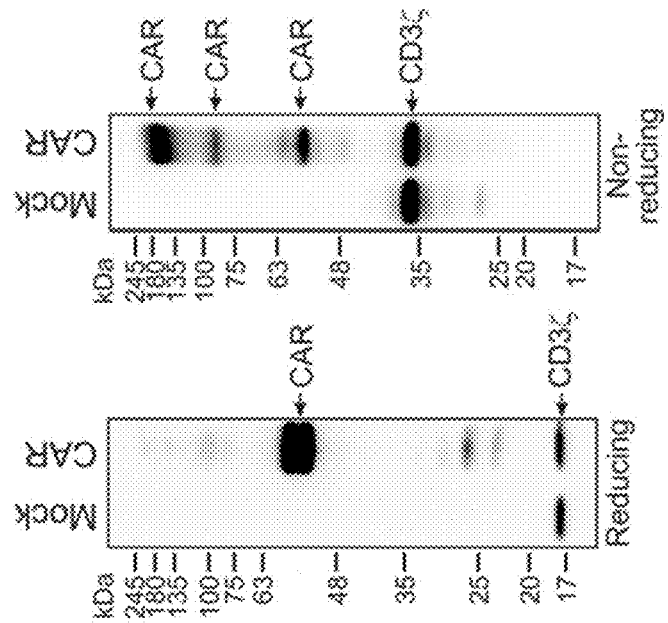
FIG. 9A and FIG. 9B show expression of anti-CD7-41BB-CD3ζ CAR in human peripheral blood T lymphocytes.
Figure 9A:
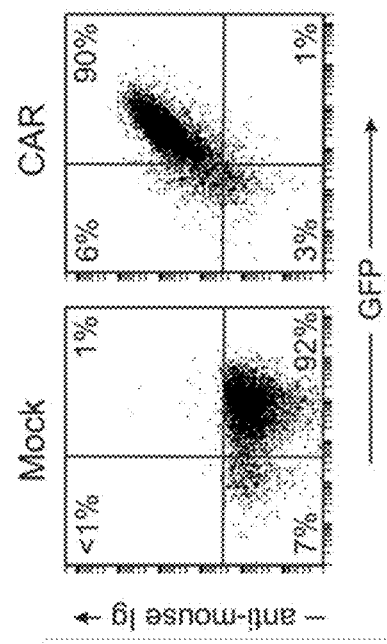

To determine the effects of anti-CD7-41BB-CD3ζ CAR in peripheral blood T lymphocytes, two different methods were used to express it: retroviral transduction (FIG. 9A) and mRNA electroporation. However, it markedly reduced T-cell viability. Mean (±SD) T-cell recovery 24 hours after mRNA electroporation was 39.8%±13.0 (n=7) of the recovery after electroporation without mRNA (FIG. 3A); if the CAR was introduced by viral transduction, cell recovery was 25.1%±16.2% (n=10) of that of mock-transduced T cells (FIG. 3B); overall, CAR expression reduced cell recovery to 31.1%±16.3% (n=17) after 24 hours. Prolonging cell culture further increased the difference in numbers between CAR- and mock-transduced cells overall (FIG. 3C). CAR expression, in the absence of target cells, induced exocytosis of lytic granules revealed by CD107a expression (FIG. 3D), suggesting that impaired cell recovery was caused by fratricide.

Figure 3I:
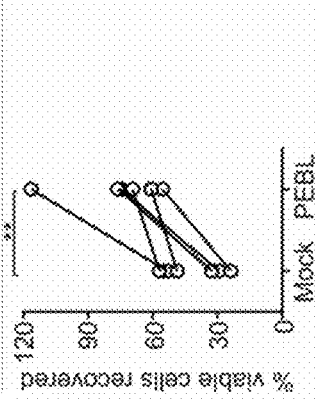
Figure 3H:
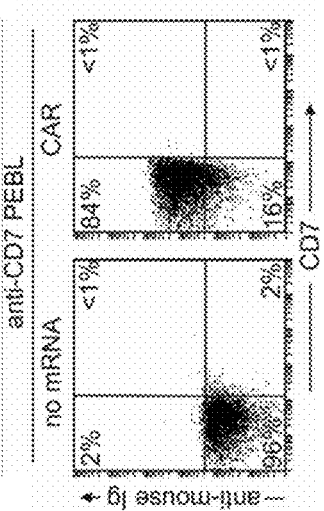
Figure 3G:
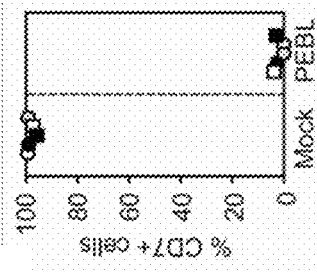
Figure 10A:
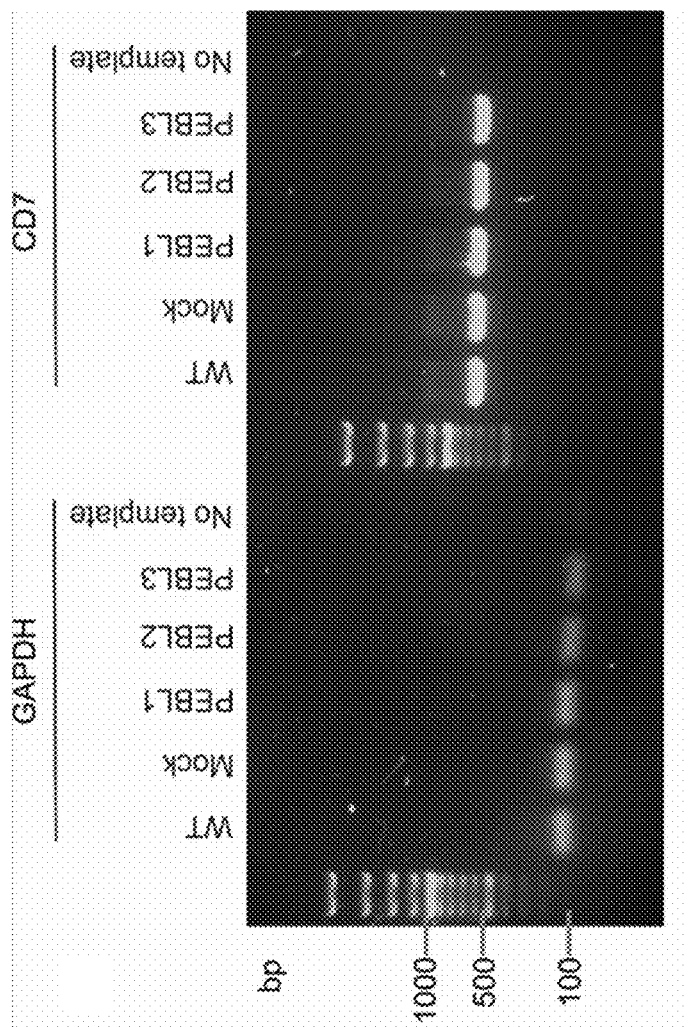
FIG. 10A and FIG. 10B illustrate downregulation of CD7 protein expression with anti-CD7 PEBLs. Flow cytometric dot plot illustrate GFP expression (x axes), CD7 expression (y axes, top row), and intracellular anti-CD7 PEBL-1 expression (y axes, bottom row) (FIG. 10A). T lymphocytes were retrovirally transduced with anti-CD7 PEBL-1 or a vector containing GFP alone ("Mock"). T-cells were stained with an anti-CD7 antibody (M-T701; BD Biosciences) conjugated to phycoerythrin. Intracellular expression of PEBL-1 was tested with a PE-conjugated anti-Myc antibody (9B11; Cell Signaling Technology) which binds to the sequence EQKLISEEDL (SEQ ID NO:40) incorporated in the ER-binding motif. Prior to antibody labelling, cells were permeabilized with 8E reagent (a permeabilization reagent developed in our laboratory).
Figure 10B:
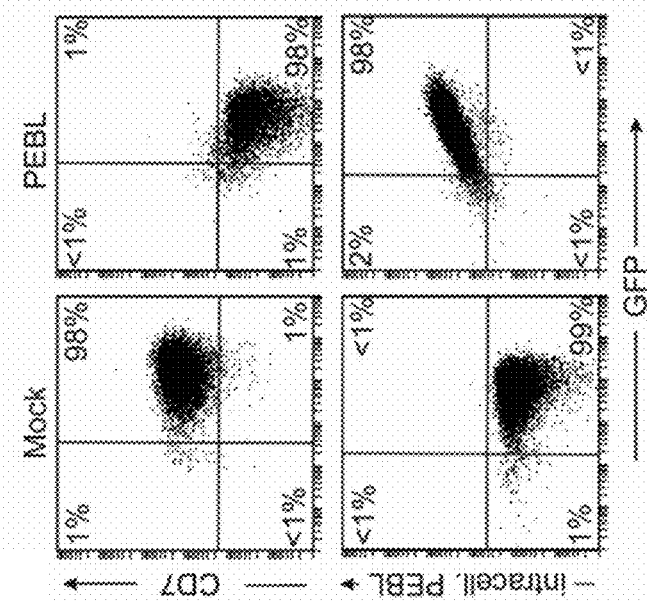

Downregulation of CD7 Prevents T Cell Fratricide and does not Affect T Cell Function If the poor T-cell recovery was caused by fratricide mediated by CAR binding to CD7 expressed by the T cells, then it should improve by downregulating CD7 prior to CAR expression. To test this prediction, a rapid and practical method recently developed based on the expression of the anti-CD7 scFv linked to amino acid sequences containing the ER retention domains KDEL or KKMP [anti-CD7 Protein Expression Blocker (PEBL)] was applied. (FIG. 3E). These fasten the constructs to the ER/Golgi, preventing secretion or membrane expression of the targeted protein.[39,40] 3 anti-CD7 PEBL constructs were tested and PEBL-1 was selected PEBL-1 for the next experiments (FIGS. 3E and 3F). CD7 surface expression was essentially abrogated in all T cells transduced with this construct while CD7 mRNA expression was retained (FIG. 3F, FIG. 10A and FIG. 10B); in 5 experiments, 98.1%±1.5% mock-transduced T cells were CD7+ versus 2.0%±1.7% for T cells transduced with the anti-CD7 PEBL (P<0.0001) (FIG. 3G). When the anti-CD7 CAR was expressed by electroporation in cells with downregulated CD7, it was clearly detectable by flow cytometry (FIG. 3H). By expressing the CAR in cells with CD7 knock-down, T cell viability markedly improved (FIG. 3I); in 6 paired experiments, viable cell recovery after CAR mRNA electroporation was consistently superior in T cells that had been previously transduced with the anti-CD7 PEBL (P=0.008).

After anti-CD7 PEBL transduction, the proportion of CD4 and CD8 cells was similar to that of mock-transduced cells (FIG. 4A). Absence of CD7 expression on the surface membrane did not affect T-cell survival in culture (FIG. 4B). To further probe the functional capacity of T cells transduced with anti-CD7 PEBL, the cells were engineered to express the anti-CD19-CAR (FIG. CA). Their capacity to exert cytotoxicity, release cytotoxic granules, and secrete IFNγ in the presence of CD19+ ALL cells was tested. As shown in FIGS. 4D, 4E, and 4F, PEBL transduction and lack of surface CD7 did not altered CAR-mediated cell function.

Anti-CD7-41BB-CD34 CAR Induces Powerful Cytotoxicity Against CD7+ Leukemic Cells CD7-negative T cells were prepared using anti-CD7 PEBL, and electroporated with the anti-CD7-41BB-CD3ζ CAR mRNA. Their anti-leukemic capacity was assessed in co-cultures with the CD7+ leukemia cell lines MOLT-4, CCRF-CEM, Jurkat, Loucy or KG1a. As shown in FIG. 5A, cytotoxicity was dramatically increased by the CAR expression. PEBL-CAR T cells were also highly effective against primary T-ALL cells obtained from patients (FIG. 5B).

Figures 5E, 5F:
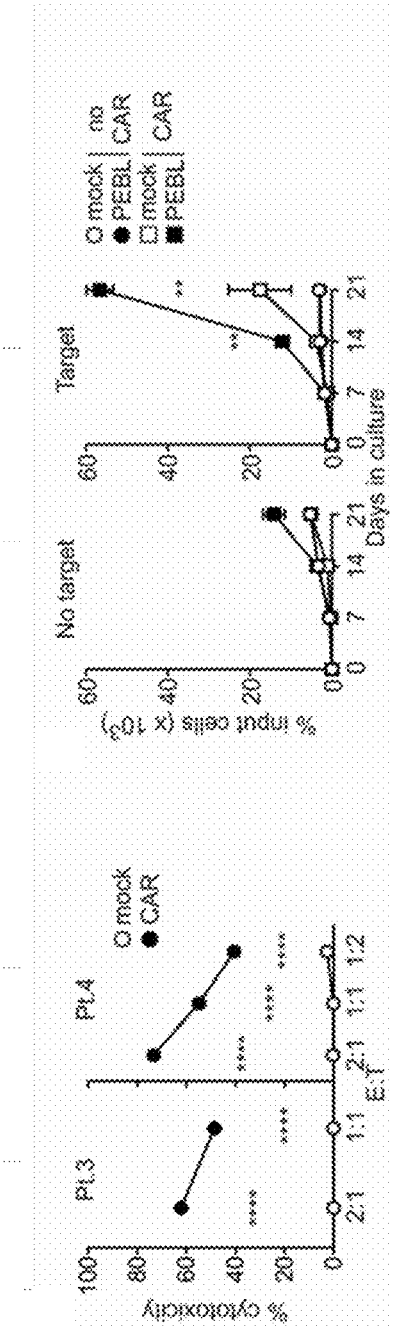
Figure 11A:
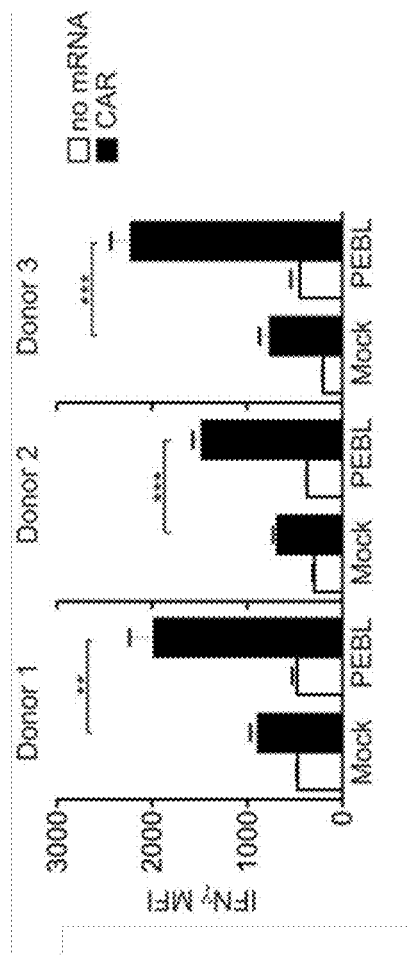
FIG. 11A and FIG. 11B show that anti-CD7 CAR signal elicited higher cytokine secretion in T cells with CD7 knock-down expression by anti-CD7 PEBL. T lymphocytes from 3 donors were transduced with anti-CD7 PEBL or GFP alone ("Mock") were electroporated with either anti-CD7-41BB-CD3ζ mRNA or no mRNA. Intracellular IFNγ (FIG. 11A) and TNFα (FIG. 11B) expression in T cells after 6 hours of co-culture with MOLT4 was measured. Bars represent mean (±SD) of triplicate MFI measurements. , P<0.01; *, P<0.001; ****, P<0.0001.
Figure 11B:
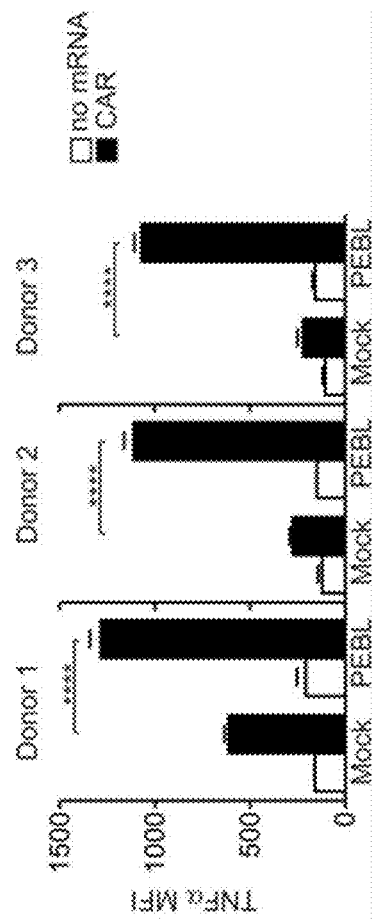
Figure 13E:
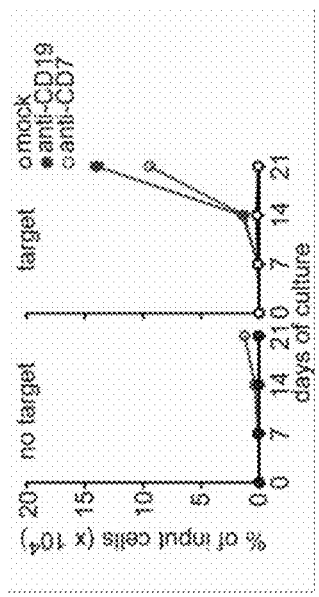
Figure 13D:
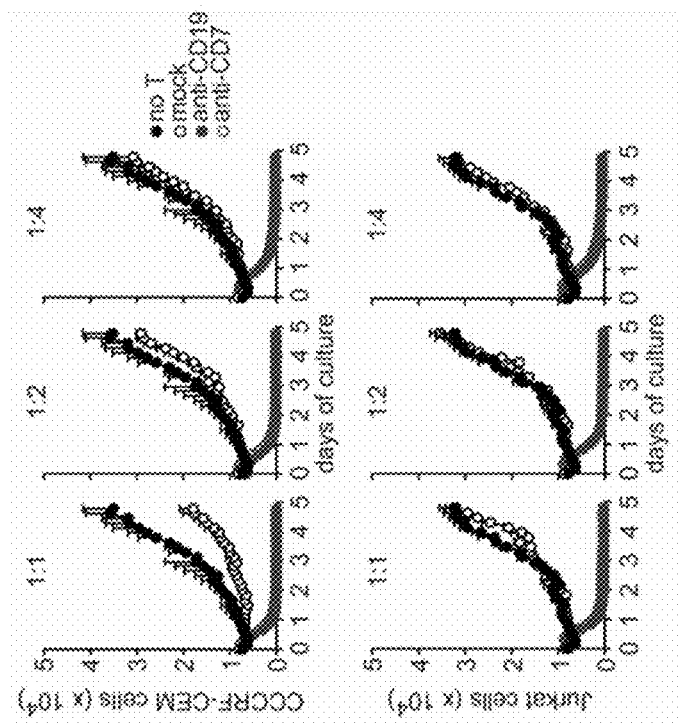

The cytotoxicity of PEBL-CAR T cells was compared to that of the residual T cells recovered after CAR electroporation in cells not transduced with PEBL. In 45 experiments with cells from 3 donors, cytotoxicity of the PEBL-CAR cells consistently surpassed that of non-PEBL T cells (FIG. 5C). The superior activity of the former cells was also observed when comparing the expressions of CD107a (FIG. 5D), IFNγ (FIG. 11A) and TNFα (FIG. 11B). Expression of PEBL and CAR by sequential retroviral transduction also produced powerful cytotoxicity against patient-derived T-ALL cells (FIG. 5E) and cell lines (FIG. 12). Proliferation of anti-CD7 PEBL-CAR-T cells in the presence of CD7+ target cells was much higher than that of CAR-T without CD7 downregulation by PEBL (P<0.01)(FIG. 5F). Finally, the cytotoxicity exerted by anti-CD7 PEBL-CAR T cells was compared to that of T cells expressing an anti-CD19-41BB-CD3ζ CAR[5] against the same target cells. To this end, CCRF-CEM and Jurkat cells were transduced with CD19, and also expressed either CAR in cells previously transduced with anti-CD7 PEBL (FIGS. 13A and 13B). Anti-CD7 and anti-CD19 CAR T cells had similar short- and long-term cytotoxicity (FIGS. 13C and 13D); long-term proliferative capacity in the presence of CD19+ CD7+ target cells was slightly lower for the anti-CD7 CAR-T cells (FIG. 13E), which might be explained by the lower expression of CD7 versus CD19 on target cells (FIG. 13B)

Anti-Leukemic Activity of Anti-CD7 PEBL-CAR T Cells in Murine Models of T-ALL

Figure 6A:
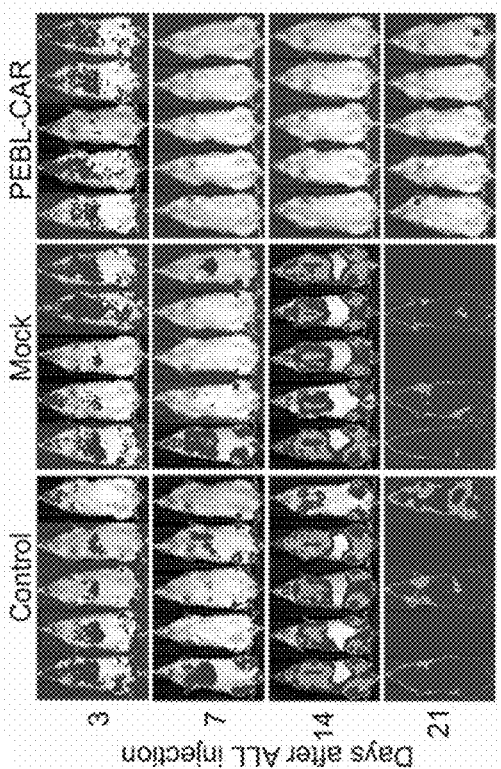
FIG. 6A-FIG. 6D show PEBL-transduced T-cells expressing anti-CD7-41BB-CD3ζ CAR exert antitumor activity in xenografts. NOD-SCID-IL2RG null mice were infused intravenously (i.v.) with $1\times10^6$ CCRF-CEM cells labelled with luciferase. $2\times10^7$ PEBL-CAR T cells were administered i.v. on day 7 (FIG. 6A), or on day 3 and day 7 (FIG. 6B) after leukemic cell infusion to 3 and 5 mice, respectively. The remaining mice received either mock-transduced T cells, or RPMI-1640 instead of cells ("Control"). All mice received 20,000 IU IL-2 once every two days intraperitoneally (i.p.). Shown is in vivo imaging of leukemia cell growth after D-luciferin i.p. injection. Ventral images of mice on day 3 in FIG. 6B are shown with enhanced sensitivity to demonstrate CCRF-CEM engraftment in all mice. The complete set of luminescence images is in FIG. 14.
Figure 6B:
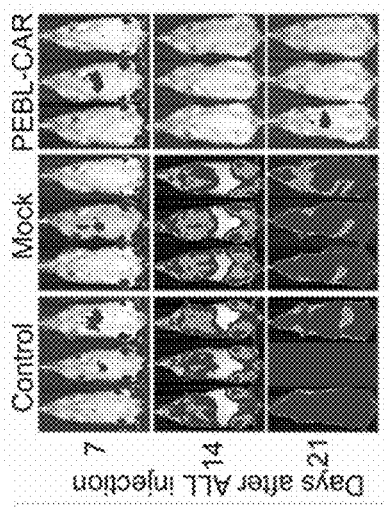
Figure 6C:
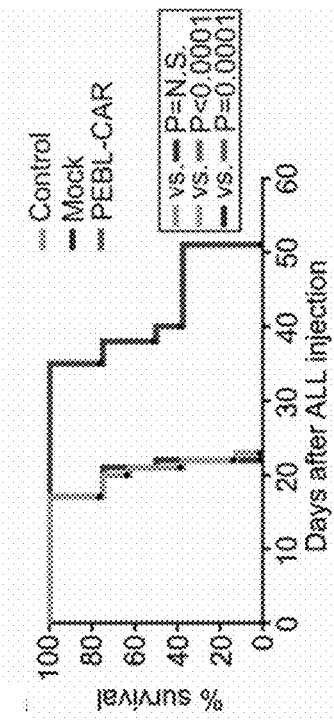
Figure 6D:
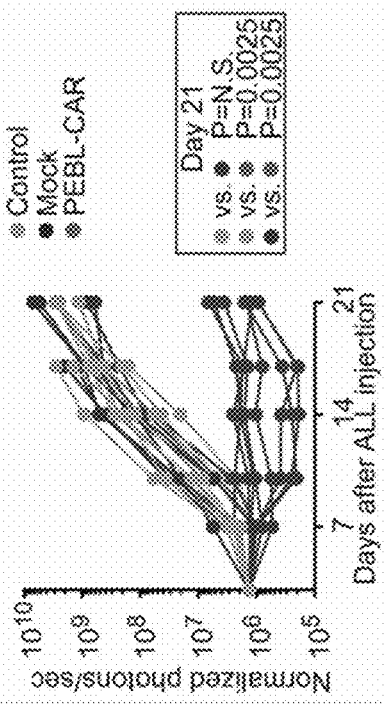
Figure 14B:
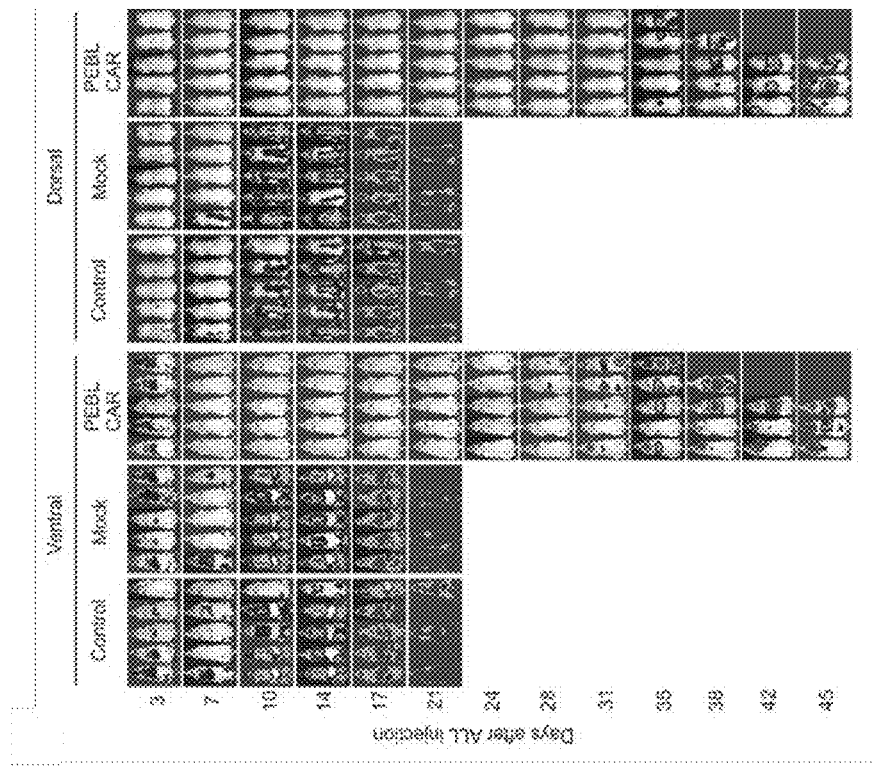
FIG. 14A-FIG. 14C illustrate PEBL-transduced T-cells expressing anti-CD7-41BB-CD3ζ CAR exerted antitumor activity in mouse models. NOD-SCID-IL2RGnull mice were infused intravenously with $1\times10^6$ CCRF-CEM cells labeled with luciferase. $2\times10^7$ PEBL-CAR T cells were administered intravenously on day 7 (FIG. 14A) or on day 3 and day 7 (FIG. 14B) after leukemic cell infusion to 3 and 5 mice, respectively. The remaining mice received either mock-transduced T cells, or RPMI-1640 instead of cells ("Control"). All mice received 20,000 IU IL-2 once every two days intraperitoneally (i.p.). In vivo imaging of leukemia cell growth was performed after D-luciferin i.p. injection. Ventral images of mice on day 3 in FIG. 14B are shown with enhanced sensitivity to demonstrate leukemia cell engraftment in all mice. Leukemia cell growth expressed as photons per second over time normalised to average of ventral plus dorsal signals in all mice before CAR-T cell infusion (FIG. 14C). Each symbol corresponds to bioluminescence measurements in each mouse.
Figure 14A:
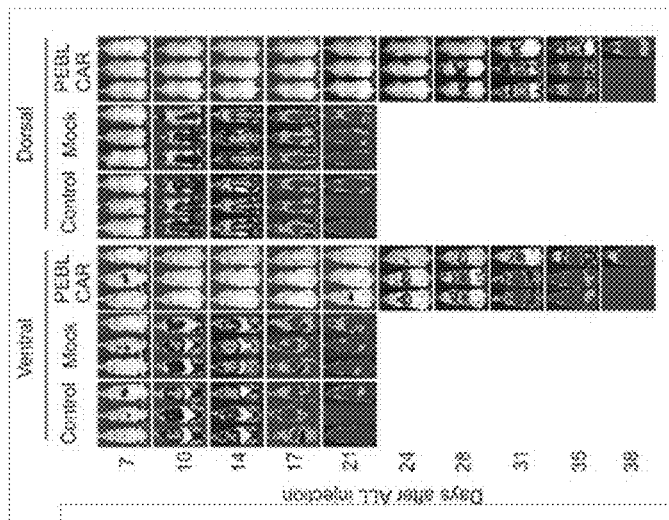
Figure 14C:
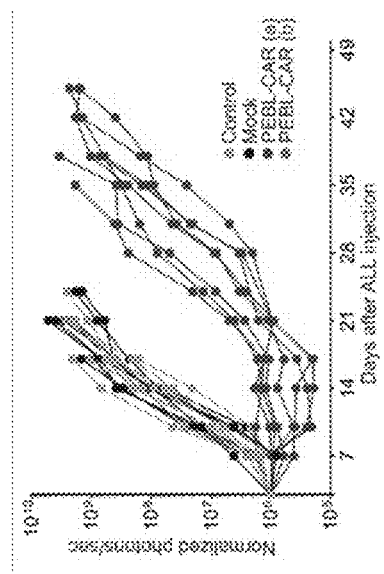

To further gauge the anti-tumor capacity of anti-CD7 PEBL-CAR T cells, NOD/scid IL2RGnull were engrafted with CCRF-CEM cells. T cells retrovirally transduced with anti-CD7 PEBL and anti-CD7 CAR produced considerable anti-leukemic effect, with a marked reduction in leukemia cell burden and a decrease in leukemia cell growth (FIGS. 6A-6C; FIGS. 14A and 14B). Three weeks after leukemic cell injection, median percent CCRF-CEM cells in peripheral blood by flow cytometry was 68% for control mice (n=5) and 67% for those who receive GFP-alone T cells (n=5), but they were undetectable in mice treated with anti-CD7 PEBL-CAR T cells (FIG. 15A). Relapse occurring after anti-CD7 PEBL-CAR T cell treatment was not due to CCRF-CEM cell subsets lacking CD7; leukemic cells continued to express high levels of CD7 and sensitivity to anti-CD7 CAR cytotoxicity remained high regardless of whether CCRF-CEM cells were derived from liver or spleen of relapsing mice or directly from the original cell culture (FIG. 15B).

Figure 16:
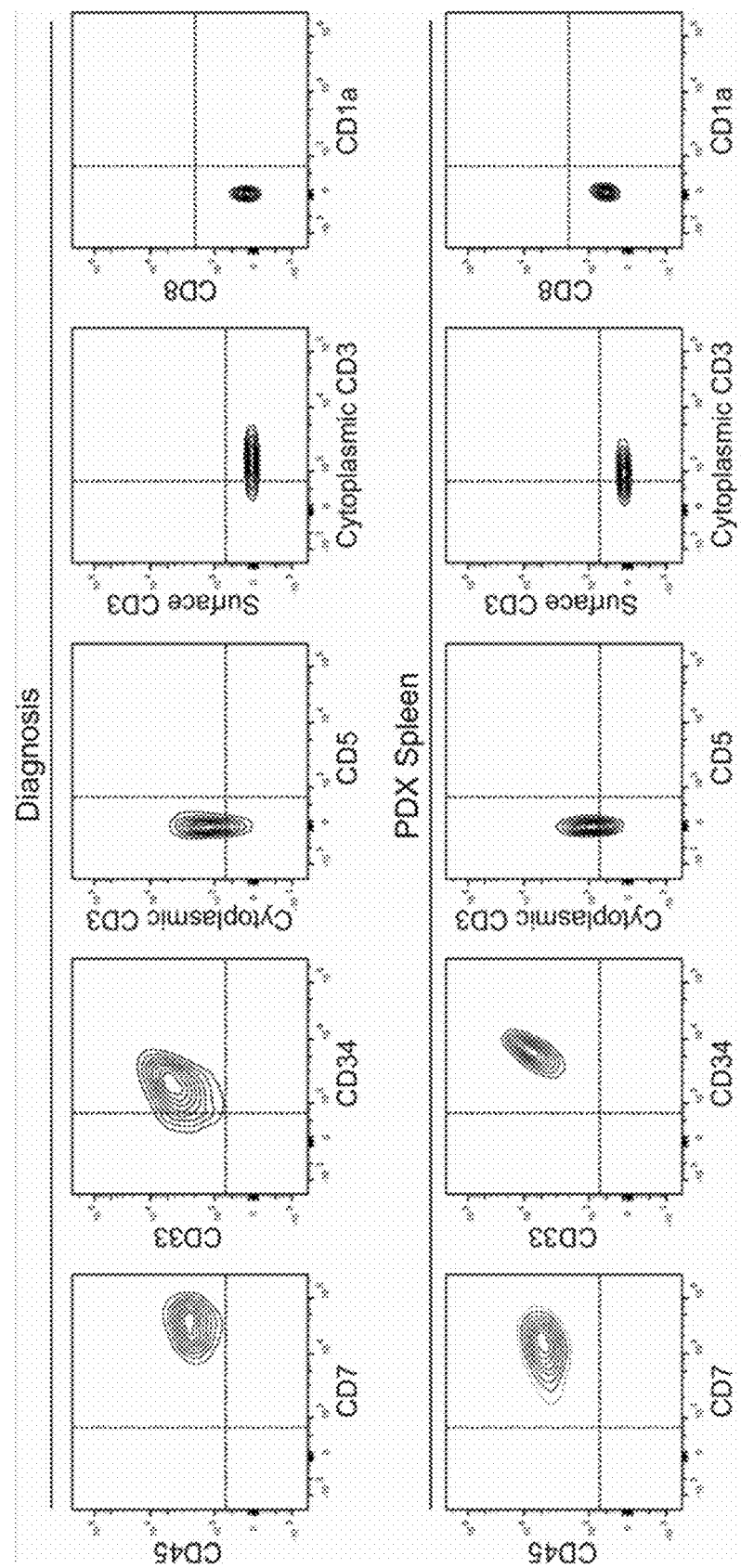
FIG. 16 provides immunophenotypic features of ETP-ALL at diagnosis and after propagation in NOD-SCID-IL2RGnull mice. Flow cytometric contour plots show the immunophenotype diagnostic bone marrow samples of the ETP-ALL used to develop the PDX model in this study and that of the ETP-ALL cells recovered from the spleen of one of the control mice shown in FIG. 7. The following antibodies were used: CD7-PE, CD45-APC-H7, CD34-PerCP, CD8-BV510, CD5-PE-Cy7, CD3-PerCP (for cytoplasmic staining), CD3-V450 (for surface staining), all from BD Biosciences; CD33-BV421 (Biolegend); CD1a-PE (Beckman Coulter). Quadrants were drawn based on staining with isotype-matched non-reactive antibodies conjugated to the same fluorochromes.

To test PEBL-CAR T cells against primary leukemic cells in vivo, a PDX model of ETP-ALL was used. The PDX model allows propagation of leukemic cells derived from a patient with ETP-ALL at diagnosis in NOD/scid IL2RGnull mice. Leukemic cells retained an immunophenotype matching that determined at diagnosis, with expression of CD7, CD34, CD33, and absence of surface CD3, CD1a, CD8 and CD5 (FIG. 16); the cells were unable to survive and expand ex vivo, and needed to be injected in mice for propagation. All mice had ETP-ALL in peripheral blood at the time of CAR-T treatment (FIG. 7A). As shown in FIG. 7B, ETP-ALL cells represented the majority of leukocytes in bone marrow, spleen liver and lung. After administration of PEBL-CAR T cells ($2 \times 10^7$ in one mouse, $2 \times 10^6$ in the remaining 4), leukemic cell numbers in peripheral blood decrease dramatically, while PEBL-CAR-T cells became detectable in all mice (FIG. 7A). In blood smears, smudge cells were prominent suggesting leukemia cell lysis (FIG. 7C). Leukemia progressed in all 5 control mice, which were euthanized after when ETP-ALL were >80% of peripheral blood mononucleated cells. The mouse treated with $2 \times 10^7$ PEBL-CAR-T cells, died of apparent graft-versus-host disease (GvHD) 23 days after PEBL-CAR-T cell infusion. No ETP-ALL could be detected in blood, bone marrow, liver, spleen, lung and brain, while PEBL-CAR T cells were detectable in all tissues (FIGS. 7D and 7E). The 4 mice treated with $2 \times 10^6$ PEBL-CAR T cells are alive, 25 (n=1) to 39 (n=3) days post-infusion, with no signs of GvHD.

Discussion

Durable remissions in patients with B-cell leukemia and lymphoma can be achieved with CAR-T cells but effective options are lacking for patients with T-cell malignancies. To bridge this gap, a CAR-T cell approach that could be rapidly translated into clinical intervention was developed and described herein. CD7, a widely expressed surface T-cell marker, which is highly stable even in T-ALL cells exposed to chemotherapy was targeted. A second-generation anti-CD7 CAR was designed. It was determined that suppression of CD7 surface expression in T cells was essential; without it, the CAR caused severe T-cell loss, and the full functional potential of CAR-T cells could not be achieved. Transduction of anti-CD7 PEBL resulted in virtually instantaneous abrogation of CD7 expression. Expression of anti-CD7 CAR in such cells produced powerful anti-leukemic activity in vitro, as well as in xenograft and PDX models of T-ALL. Thus, by using this strategy, large numbers of CAR-T cells were rapidly generated and were used to exert robust and specific cytotoxicity against T-cell malignancies, including one of the most aggressive forms, ETP-ALL.

The PEBL technology as described herein to downregulate endogenous CD7 is based on the use of a scFv directed against the targeted antigen coupled with an ER/Golgi-retention motif. In this way, any newly synthesized CD7 remains anchored in the ER and/or Golgi, and its surface expression is prevented. This method was remarkably effective in downregulating CD7 and suppressing CAR-mediated fratricide. Importantly, intracellular retention of CD7 did not alter T-cell function and allowed normal expansion, cytokine secretion, and cytotoxicity. This is consistent with results of studies with CD7-deficient mice which showed normal lymphocyte populations in lymphoid tissues.[41,42] An alternative approach to downregulate CD7 would be to apply gene editing methods, such as meganucleases, TALEN, or CRISPR/Cas9.[43] To this end, a recent study reported an anti-CD7 CAR which was expressed in T cells with CD7 gene deletion by CRISPR/Cas.[9,44] Besides differences in co-stimulatory molecules (the CAR described herein has 4-1BB instead of CD28) which may have clinical impact,[45,46] the high specificity and practical nature of the PEBL strategy make it particularly attractive for current clinical use. This method requires a simple transduction with the same viral vector carrying the CAR, either as two sequential transductions or a single transduction with a bicistronic vector carrying both constructs. It fits well with established clinical-grade cell manufacturing processes, and does not raise possible regulatory concerns associated with off-target activity.[47,48]

CD7 is a hallmark molecule for early T-cell differentiation; it is nearly universally expressed in T-ALL, and among normal cells, its expression is limited to T cells.[19,29-32] In a clinical study with an anti-CD7-ricin-A-chain immunotoxin in patients with T-cell lymphoma, the dose-limiting toxicity was vascular leak syndrome, a side-effect seen with other toxin-conjugates; no binding of anti-CD7 was found in endothelial cells of various tissues.[49] Nevertheless, transient expression of the CAR by mRNA electroporation might be considered in early studies assessing potential for acute toxicities of anti-CD7 PEBL-CAR T cells. A concern of anti-CD7 CAR therapy is the depletion of normal T cells by the infused cells, leading to immunodeficiency. One can envisage the initial application of this technology as a means to reduce MRD in patients with high-risk T-ALL, therefore maximizing the success of allogeneic hematopoietic stem cell transplantation.[50] In such instances, anti-CD7 CAR T cells would be eliminated by the transplant conditioning and the T-cell compartment reconstituted from donor stem cells. Outside the transplant setting, "suicide genes" could be activated once leukemia eradication has been achieved.[51] Ultimately, this may not be an issue, as the infused anti-CD7 T cells (which retain their endogenous CD3/TCR complex) might reconstitute a sufficiently wide T-cell repertoire. To this end, it should be noted that subsets of CD4 memory and CD8 effector T cells in human blood lymphocyte which do not express CD7 have been described,[52,53] and that T-ALL cells express CD7 at higher levels than normal T cells. Thus, CD7-dim subsets might help to repopulate the T-cell repertoire even after CD7-directed therapy.

The standard treatment of T-ALL mainly relies on intensive chemotherapy plus hematopoietic stem cell transplant for patients with high-risk disease. Results are far from satisfactory and have considerable morbidity and mortality.[54,55] The findings presented herein suggest the infusion of anti-CD7 PEBL-CAR T cells could significantly enhance, or perhaps replace, existing chemotherapy- and transplant-based strategies. Conceivably, CAR expression together with downregulation of the targeted antigen in T cells should also be applicable to other T cell markers, such as CD3, CD2, and CD5 whose expression is prevalent in T-cell lymphoproliferative neoplasms. Because a fraction of high-risk acute myeloid leukemia cases express CD7,[19,30,56] testing the potential of anti-CD7 CAR-T cells for this leukemia subtype is also warranted.

REFERENCES

1. Eshhar Z, Waks T, Gross G, Schindler D G. Specific activation and targeting of cytotoxic lymphocytes through chimeric single chains consisting of antibody-binding domains and the gamma or zeta subunits of the immunoglobulin and T-cell receptors. Proc Natl Acad Sci USA 1993; 90(2): 720-724.
2. Geiger T L, Leitenberg D, Flavell R A. The TCR zeta-chain immunoreceptor tyrosine-based activation motifs are sufficient for the activation and differentiation of primary T lymphocytes. J Immunol 1999; 162(10): 5931-5939.
3. Brentjens R J, Latouche J B, Santos E, et al. Eradication of systemic B-cell tumors by genetically targeted human T lymphocytes co-stimulated by CD80 and interleukin-15. Nat Med 2003; 9(3):279-286.
4. Cooper L J, Topp M S, Serrano L M, et al. T-cell clones can be rendered specific for CD19: toward the selective augmentation of the graft-versus-B-lineage leukemia effect. Blood 2003; 101(4):1637-1644.
5. Imai C, Mihara K, Andreansky M, Nicholson I C, Pui C H, Campana D. Chimeric receptors with 4-1BB signaling capacity provoke potent cytotoxicity against acute lymphoblastic leukemia. Leukemia 2004; 18:676-684.
6. Rosenberg S A, Restifo N P. Adoptive cell transfer as personalized immunotherapy for human cancer. Science 2015; 348(6230):62-68.
7. Brentjens R J, Santos E, Nikhamin Y, et al. Genetically targeted T cells eradicate systemic acute lymphoblastic leukemia xenografts. Clin Cancer Res 2007; 13(18 Pt 1):5426-5435.
8. Haso W, Lee D W, Shah N N, et al. Anti-CD22-chimeric antigen receptors targeting B-cell precursor acute lymphoblastic leukemia. Blood 2013; 121(7):1165-1174.
9. Nadler L M, Anderson K C, Marti G, et al. B4, a human B lymphocyte-associated antigen expressed on normal, mitogen-activated, and malignant B lymphocytes. J Immunol 1983; 131(1):244-250.
10. Campana D, Janossy G, Bofill M, et al. Human B cell development. I. Phenotypic differences of B lymphocytes in the bone marrow and peripheral lymphoid tissue. J Immunol 1985; 134(3):1524-1530.
11. Porter D L, Levine B L, Kalos M, Bagg A, June C H. Chimeric antigen receptor-modified T cells in chronic lymphoid leukemia. N Engl J Med 2011; 365(8):725-733.
12. Grupp S A, Kalos M, Barrett D, et al. Chimeric antigen receptor-modified T cells for acute lymphoid leukemia. N Engl J Med 2013; 368(16):1509-1518.
13. Till B G, Jensen M C, Wang J, et al. CD20-specific adoptive immunotherapy for lymphoma using a chimeric antigen receptor with both CD28 and 4-1BB domains: pilot clinical trial results. Blood 2012; 119(17):3940-3950.
14. Kochenderfer J N, Dudley M E, Feldman S A, et al. B-cell depletion and remissions of malignancy along with cytokine-associated toxicity in a clinical trial of anti-CD19 chimeric-antigen-receptor-transduced T cells. Blood 2012; 119(12):2709-2720.
15. Davila M L, Riviere I, Wang X, et al. Efficacy and Toxicity Management of 19-28z CAR T Cell Therapy in B Cell Acute Lymphoblastic Leukemia. Sci Transl Med 2014; 6(224): 224ra225.
16. Maude S L, Frey N, Shaw P A, et al. Chimeric antigen receptor T cells for sustained remissions in leukemia. N Engl J Med 2014; 371(16):1507-1517.
17. Lee D W, Kochenderfer J N, Stetler-Stevenson M, et al. T cells expressing CD19 chimeric antigen receptors for acute lymphoblastic leukaemia in children and young adults: a phase 1 dose-escalation trial. Lancet 2015; 385(9967):517-528.
18. Turtle C J, Hanafi L A, Berger C, et al. CD19 CAR-T cells of defined CD4+:CD8+ composition in adult B cell ALL patients. J Clin Invest 2016; 126(6):2123-2138.
19. Coustan-Smith E, Mullighan C G, Onciu M, et al. Early T-cell precursor leukaemia: a subtype of very high-risk acute lymphoblastic leukaemia. Lancet Oncol 2009; 10(2): 147-156.
20. Zhang J, Ding L, Holmfeldt L, et al. The genetic basis of early T-cell precursor acute lymphoblastic leukaemia. Nature 2012; 481(7380):157-163.
21. Inukai T, Kiyokawa N, Campana D, et al. Clinical significance of early T-cell precursor acute lymphoblastic leukaemia: results of the Tokyo Children's Cancer Study Group Study L99-15. Br J Haematol 2012; 156(3):358-365.
22. Neumann M, Heesch S, Gokbuget N, et al. Clinical and molecular characterization of early T-cell precursor leukemia: a high-risk subgroup in adult T-ALL with a high frequency of FLT3 mutations. Blood Cancer J 2012; 2(1):e55.
23. Jain N, Lamb A V, O'Brien S, et al. Early T-cell precursor acute lymphoblastic leukemia/lymphoma (ETP-ALL/LBL) in adolescents and adults: a high-risk subtype. Blood 2016; 127(15): 1863-1869.
24. Marks D I, Rowntree C. Management of adults with T-cell lymphoblastic leukemia. Blood 2017; 129(9):1134-1142.
25. Campana D, Pui C H. Minimal residual disease-guided therapy in childhood acute lymphoblastic leukemia. Blood 2017; 129(14):1913-1918.
26. Coustan-Smith E, Sancho J, Hancock M L, et al. Use of peripheral blood instead of bone marrow to monitor residual disease in children with acute lymphoblastic leukemia. Blood 2002; 100:2399-2402.
27. Mihara K, Yanagihara K, Takigahira M, et al. Activated T-cell-mediated immunotherapy with a chimeric receptor against CD38 in B-cell non-Hodgkin lymphoma. J Immunother 2009; 32(7):737-743.
28. Mamonkin M, Rouce R H, Tashiro H, Brenner M K. A T-cell-directed chimeric antigen receptor for the selective treatment of T-cell malignancies. Blood 2015; 126(8): 983-992.
29. Haynes B F, Eisenbarth G S, Fauci A S. Human lymphocyte antigens: production of a monoclonal antibody that defines functional thymus-derived lymphocyte subsets. Proc Natl Acad Sci USA 1979; 76(11):5829-5833.
30. Vodinelich L, Tax W, Bai Y, Pegram S, Capel P, Greaves M F. A monoclonal antibody (WT1) for detecting leukemias of T-cell precursors (T-ALL). Blood 1983; 62(5): 1108-1113.
31. Janossy G, Coustan-Smith E, Campana D. The reliability of cytoplasmic CD3 and CD22 antigen expression in the 31. immunodiagnosis of acute leukemia: a study of 500 cases. Leukemia 1989; 3(3):170-181.
32. Yeoh E J, Ross M E, Shurtleff S A, et al. Classification, subtype discovery, and prediction of outcome in pediatric acute lymphoblastic leukemia by gene expression profiling. Cancer Cell 2002; 1:133-143.
33. Manabe A, Coustan-Smith E, Kumagai M, et al. Interleukin-4 induces programmed cell death (apoptosis) in cases of high-risk acute lymphoblastic leukemia. Blood 1994; 83(7):1731-1737.
34. Peipp M, Kupers H, Saul D, et al. A recombinant CD7-specific single-chain immunotoxin is a potent inducer of apoptosis in acute leukemic T cells. Cancer Res 2002; 62(10):2848-2855.
35. Kudo K, Imai C, Lorenzini P, et al. T lymphocytes expressing a CD16 signaling receptor exert antibody-dependent cancer cell killing. Cancer Res 2014; 74(1):93-103.
36. Shimasaki N, Fujisaki H, Cho D, et al. A clinically adaptable method to enhance the cytotoxicity of natural killer cells against B-cell malignancies. Cytotherapy. 2012; 14(7):830-40.
37. Shimasaki N, Campana D. Natural killer cell reprogramming with chimeric immune receptors. Methods Mol Biol 2013; 969:203-220.
38. Chang Y H, Connolly J, Shimasaki N, Mimura K, Kono K, Campana D. A Chimeric Receptor with NKG2D Specificity Enhances Natural Killer Cell Activation and Killing of Tumor Cells. Cancer Res 2013; 73(6):1777-1786.
39. Munro S, Pelham H R. A C-terminal signal prevents secretion of luminal E R proteins. Cell 1987; 48(5):899-907.
40. Jackson M R, Nilsson T, Peterson P A. Identification of a consensus motif for retention of transmembrane proteins in the endoplasmic reticulum. EMBO J 1990; 9(10):3153-3162.
41. Bonilla F A, Kokron C M, Swinton P, Geha R S. Targeted gene disruption of murine CD7. Int Immunol 1997; 9(12):1875-1883.
42. Lee D M, Staats H F, Sundy J S, et al. Immunologic characterization of CD7-deficient mice. J Immunol 1998; 160(12):5749-5756.
43. Boettcher M, McManus M T. Choosing the right tool for the job: RNAi, TALEN, or CRISPR. Mol Cell 2015; 58(4):575-585.
44. Gomes-Silva D, Srinivasan M, Sharma S, et al. CD7-edited T cells expressing a CD7-specific CAR for the therapy of T-cell malignancies. Blood. 2017 May 24. pii: blood-2017-01-761320.
45. Campana D, Schwarz H, Imai C. 4-1BB chimeric antigen receptors. Cancer J 2014; 20(2):134-140.
46. Zhao Z, Condomines M, van der Stegen S J, et al. Structural Design of Engineered Costimulation Determines Tumor Rejection Kinetics and Persistence of CART Cells. Cancer Cell 2015; 28(4):415-428.
47. Tsai S Q, Joung J K. Defining and improving the genome-wide specificities of CRISPR-Cas9 nucleases. Nat Rev Genet 2016; 17(5):300-312.
48. Cameron P, Fuller C K, Donohoue P D, et al. Mapping the genomic landscape of CRISPR-Cas9 cleavage. Nat Methods 2017; 14(6):600-606.
49. Frankel A E, Laver J H, Willingham M C, Burns L J, Kersey J H, Vallera D A. Therapy of patients with T-cell lymphomas and leukemias using an anti-CD7 monoclonal antibody-ricin A chain immunotoxin. Leuk Lymphoma 1997; 26(3-4):287-298.
50. Leung W, Pui C H, Coustan-Smith E, et al. Detectable minimal residual disease before hematopoietic cell transplantation is prognostic but does not preclude cure for children with very-high-risk leukemia. Blood 2012; 120 (2):468-72.
51. Straathof K C, Spencer D M, Sutton R E, Rooney C M. Suicide genes as safety switches in T lymphocytes. Cytotherapy 2003; 5(3):227-230.
52. Reinhold U, Abken H, Kukel S, et al. CD7− T cells represent a subset of normal human blood lymphocytes. J Immunol 1993; 150(5):2081-2089.
53. Aandahl E M, Sandberg J K, Beckerman K P, Tasken K, Moretto W J, Nixon D F. CD7 is a differentiation marker that identifies multiple CD8 T cell effector subsets. J Immunol 2003; 170(5):2349-2355.
54. Raetz E A, Teachey D T. T-cell acute lymphoblastic leukemia. Hematology Am Soc Hematol Educ Program 2016; 2016(1):580-588.
55. Jabbour E, O'Brien S, Konopleva M, Kantarjian H. New insights into the pathophysiology and therapy of adult acute lymphoblastic leukemia. Cancer 2015; 121(15):2517-2528.
56. Kita K, Miwa H, Nakase K, et al. Clinical importance of CD7 expression in acute myelocytic leukemia. The Japan Cooperative Group of Leukemia/Lymphoma. Blood 1993; 81(9):2399-2405.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for treating T cell acute lymphoblastic leukemia (T-ALL) or early T-cell progenitor acute lymphoblastic leukemia (ETP-ALL) in a patient in need thereof, comprising administering a therapeutically effective amount of an engineered T cell having substantially suppressed surface expression of endogenous CD7 and expressing an anti-CD7 chimeric antigen receptor (CAR) to said patient, thereby treating T ALL or ETP-ALL in the patient in need thereof, wherein said engineered T cell comprises:
  i) a nucleic acid comprising a nucleotide sequence encoding a first single chain variable fragment (scFv) that specifically binds to CD7 linked to an intracellular localizing domain,
  wherein said first scFv comprises:
    a heavy chain variable domain having at least 90% sequence identity to the amino acid sequence of SEQ ID NO:1 and a light chain variable domain having at least 90% sequence identity to the amino acid sequence of SEQ ID NO:2,
    a heavy chain variable domain having at least 90% sequence identity to the amino acid sequence of SEQ ID NO:14 and a light chain variable domain having at least 90% sequence identity to the amino acid sequence of SEQ ID NO:15, or
    a heavy chain variable domain having at least 90% sequence identity to the amino acid sequence of SEQ ID NO:16 and a light chain variable domain having at least 90% sequence identity to the amino acid sequence of SEQ ID NO:17, and
  wherein said localizing domain comprises an endoplasmic reticulum (ER) retention sequence comprising an amino acid sequence of SEQ ID NO:8; and
  wherein said first scFv linked to said intracellular localizing domain intracellularly retains endogenous CD7 in said engineered immune cell; and
  ii) a nucleic acid comprising a nucleotide sequence encoding said anti-CD7 chimeric antigen receptor (CAR), wherein said CAR comprises a 4-1BB intracellular signaling domain, a CD3ζ intracellular signaling domain, and a second single chain variable fragment (scFv) that specifically binds to CD7.

2. The method of claim 1, wherein said 4-1BB intracellular signaling domain comprises an amino acid sequence of SEQ ID NO:3 and wherein said CD3t intracellular signaling domain comprises an amino acid sequence of SEQ ID NO:4.

3. The method of claim 1, wherein said CAR further comprises a hinge and transmembrane domain.

4. The method of claim 3, wherein said hinge and transmembrane domain comprises an amino acid sequence of SEQ ID NO:10.

5. The method of claim 1, wherein said second single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2; said second single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15; or said second single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

6. The method of claim 1, wherein said engineered cell is administered to said patient by intravenous infusion, intra-arterial infusion, intraperitoneal infusion, direct injection into tumor and/or perfusion of tumor bed after surgery, implantation at a tumor site in an artificial scaffold, or intrathecal administration.

* * * * *

UNITED STATES PATENT AND TRADEMARK OFFICE
CERTIFICATE OF CORRECTION

PATENT NO. : 10,550,183 B2  
APPLICATION NO. : 15/821170  
DATED : February 4, 2020  
INVENTOR(S) : Yi Tian Png et al.

Page 1 of 3

It is certified that error appears in the above-identified patent and that said Letters Patent is hereby corrected as shown below:

In the Specification

In Column 6, Line 4, please delete "("Da")" and insert --("D/R")--

In Column 6, Line 20, please delete "mck" and insert --mock--

In Column 10, Line 2, please delete "CD7" and insert --anti-CD7-- (first occurrence)

In Column 10, Line 13, please delete "streptavidin" and insert --streptavidin-APC--

In Column 14, Line 54, please delete "heavy" and insert --light--

In Column 22, Line 56, please delete "nucleib acid" and insert --nucleic acid--

In Column 23, Line 35, please delete "1, 2, 3, 4, 5, or 6." and insert --1, 2, 3, 4, 5, 6 of SEQ ID NO:29.--

In Column 24, Line 1, please delete "1, 2, 3, 4, 5, or 6." and insert --1, 2, 3, 4, 5, 6, of SEQ ID NO:29.--

In Column 24, Line 46, please delete "ID NO:5," and insert --ID NO:15,--

In Column 24, Line 60, please delete "1 to 5" and insert --1 to 6--

In Column 25, in Table 4 in the Component section, please delete "Anti-CD7 scFv VL (1H69)" and insert --Anti-CD7 scFv VL (TH69)--

In Column 26, Lines 20 and 21, please delete "Cas9/CRISPR" and insert --CRISPR/Cas9--

In Column 26, Line 22, please delete "Cas9/CRISPR" and insert --CRISPR/Cas9--

Signed and Sealed this  
Twenty-fifth Day of August, 2020

Andrei Iancu  
*Director of the United States Patent and Trademark Office*

CERTIFICATE OF CORRECTION (continued)
U.S. Pat. No. 10,550,183 B2

In Column 27, Line 5, please delete "CRISPR/Cas6" and insert --CRISPR/Cas9--

In Column 29, Line 50, please delete "1, 2, 3, 4, 5, or 6." and insert --1, 2, 3, 4, 5, 6 of SEQ ID NO:29.--

In Column 29, Line 51, please delete "anti-CD7 protein expression blocker" and insert --anti-CD7 CAR--

In Column 29, Line 56, please delete "anti-CD7 protein expression blocker" and insert --anti-CD7 CAR--

In Column 29, Line 64, please delete "anti-CD7 protein expression blocker" and insert --anti-CD7 CAR--

In Column 30, Line 50, please delete "anti-CD7 protein expression blocker" and insert --anti-CD7 CAR--

In Column 31, in Table 6, please delete "Amino acid" and insert --Nucleic acid--

In Column 34, Line 23, please delete "FIG. 1A" and insert --FIG. 2A--

In Column 39, Line 64, please delete "cytometry.38" and insert --cytometry.--

In Column 42, Line 6, please delete "was selected PEBL-1 for the next experiments" and insert --was selected for the next experiments--

In Column 42, Line 27, please delete "(FIG. CA)." and insert --(FIG. 4C).--

In Column 61, please delete the following:
"<400> SEQUENCE: 24
gaggtgcagc tggtcgaatc tggaggagga ctggtgaagc caggaggatc tctgaaactg agttgtgccg cttcaggcct gaccttctca agctacgcca tgagctgggt gcgacagaca cctgagaagc ggctggaatg ggtcgctagc atctcctctg gcgggttcac atactatcca gactccgtga aaggcagatt tactatctct cgggataacg caagaaatat tctgtacctg cagatgagtt cactgaggag cgaggacacc gcaatgtact attgtgccag ggacgaagtg cgcggctatc tggatgtctg gggagctggc actaccgtca ccgtctccag c"

CERTIFICATE OF CORRECTION (continued)
U.S. Pat. No. 10,550,183 B2

And insert the following correct version:
--<400> SEQUENCE: 24
gccgcataca aggatattca gatgactcag accacaagct ccctgagcgc ctccctggga gaccgagtga caatctcttg cagtgcatca cagggaatta gcaactacct gaattggtat cagcagaagc cagatggcac tgtgaaactg ctgatctact atacctctag tctgcacagt ggggtcccct cacgattcag cggatccggc tctgggacag actacagcct gactatctcc aacctggagc ccgaagatat tgccacctac tattgccagc agtactccaa gctgccttat acctttggcg ggggaacaaa gctggagatt aaaagg__

In the Claims

In Column 70, Claim 2, Line 16, please delete "CD3t" and insert --CD3zeta--